(12) United States Patent
Fukuda et al.

(10) Patent No.: US 8,946,440 B2
(45) Date of Patent: Feb. 3, 2015

(54) CYCLOPENTYLACRYLAMIDE DERIVATIVE

(75) Inventors: Yasumichi Fukuda, Tochigi (JP);
Yoshikazu Asahina, Tochigi (JP);
Masanori Takadoi, Tochigi (JP);
Masanori Yamamoto, Tokyo (JP)

(73) Assignees: Kyorin Pharmaceutical Co., Ltd.,
Tokyo (JP); Teijin Pharma Limited,
Tokyo (JP)

( * ) Notice: Subject to any disclaimer, the term of this patent is extended or adjusted under 35 U.S.C. 154(b) by 773 days.

(21) Appl. No.: 12/989,838

(22) PCT Filed: Apr. 27, 2009

(86) PCT No.: PCT/JP2009/001907
§ 371 (c)(1),
(2), (4) Date: Nov. 24, 2010

(87) PCT Pub. No.: WO2009/133687
PCT Pub. Date: Nov. 5, 2009

(65) Prior Publication Data
US 2011/0160211 A1    Jun. 30, 2011

(30) Foreign Application Priority Data

Apr. 28, 2008  (JP) .................................. 2008-116995
Jun. 24, 2008  (JP) .................................. 2008-164502

(51) Int. Cl.
| | | |
|---|---|---|
| *A61K 31/381* | (2006.01) |
| *C07D 277/34* | (2006.01) |
| *C07F 9/6509* | (2006.01) |
| *C07D 213/75* | (2006.01) |
| *C07D 231/38* | (2006.01) |
| *C07D 241/20* | (2006.01) |
| *C07D 261/14* | (2006.01) |
| *C07D 277/20* | (2006.01) |
| *C07D 277/44* | (2006.01) |
| *C07D 277/82* | (2006.01) |
| *C07D 285/08* | (2006.01) |
| *C07D 405/04* | (2006.01) |
| *C07D 405/06* | (2006.01) |
| *C07D 405/12* | (2006.01) |
| *C07D 417/04* | (2006.01) |

(Continued)

(52) U.S. Cl.
CPC ........ *C07F 9/650964* (2013.01); *C07D 213/75* (2013.01); *C07D 231/38* (2013.01); *C07D 241/20* (2013.01); *C07D 261/14* (2013.01); *C07D 277/20* (2013.01); *C07D 277/44* (2013.01); *C07D 277/82* (2013.01); *C07D 285/08* (2013.01); *C07D 405/04* (2013.01); *C07D 405/06* (2013.01); *C07D 405/12* (2013.01); *C07D 417/04* (2013.01); *C07D 417/12* (2013.01); *C07D 513/04* (2013.01); *C07F 9/5442* (2013.01); *C07F 9/6539* (2013.01)
USPC .......................................... 548/195; 514/371

(58) Field of Classification Search
USPC .......................................... 548/195; 514/371
See application file for complete search history.

(56) References Cited

U.S. PATENT DOCUMENTS

| 6,353,111 B1 | 3/2002 | Corbett et al. |
| 6,369,232 B1 | 4/2002 | Sidduri |

(Continued)

FOREIGN PATENT DOCUMENTS

| WO | 00/58293 | 10/2000 |
| WO | 01/44216 | 6/2001 |

(Continued)

OTHER PUBLICATIONS

International Search Report issued Jun. 23, 2009 in International (PCT) Application No. PCT/JP2009/001907.

(Continued)

*Primary Examiner* — Yong Chu
*Assistant Examiner* — Sonya Wright
(74) *Attorney, Agent, or Firm* — Wenderoth, Lind & Ponack, L.L.P.

(57) ABSTRACT

A compound having a hypoglycemic effect is provided. The compound and a pharmaceutically acceptable salt thereof are useful for the treatment or prevention of diabetes, obesity, and the like. The compound is represented by the general formula (1):

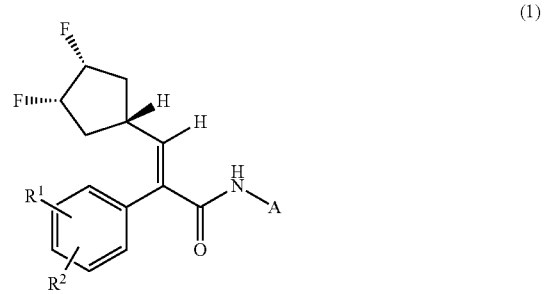

(wherein $R^1$ and $R^2$ are each independently a hydrogen atom, a halogen atom, an amino group, a hydroxyl group, a hydroxyamino group, a nitro group, a cyano group, a sulfamoyl group, a $C_1$ to $C_6$ alkyl group, a $C_1$ to $C_6$ alkoxy group, a $C_1$ to $C_6$ alkylsulfanyl group, a $C_1$ to $C_6$ alkylsulfinyl group, a $C_1$ to $C_6$ alkylsulfonyl group, or a $C_1$ to $C_6$ alkoxy-$C_1$ to $C_6$ alkylsulfonyl group, and A is a substituted or unsubstituted heteroaryl group).

23 Claims, No Drawings

(51) Int. Cl.
*C07D 417/12* (2006.01)
*C07D 513/04* (2006.01)
*C07F 9/54* (2006.01)
*C07F 9/6539* (2006.01)

(56) References Cited

U.S. PATENT DOCUMENTS

| | | | |
|---|---|---|---|
| 6,384,220 B2 | 5/2002 | Corbett et al. |
| 6,388,071 B2 | 5/2002 | Mahaney |
| 6,388,088 B1 | 5/2002 | Sidduri |
| 6,433,188 B1 | 8/2002 | Corbett et al. |
| 6,441,180 B1 | 8/2002 | Sidduri |
| 6,441,184 B1 | 8/2002 | Corbett et al. |
| 6,448,399 B1 | 9/2002 | Corbett et al. |
| 6,482,951 B2 | 11/2002 | Guertin |
| 6,486,184 B2 | 11/2002 | Kester et al. |
| 6,489,485 B2 | 12/2002 | Bizzarro et al. |
| 6,528,543 B1 | 3/2003 | Bizzarro et al. |
| 6,545,155 B2 | 4/2003 | Corbett et al. |
| 6,583,288 B2 | 6/2003 | Goodnow, Jr. et al. |
| 6,608,218 B2 | 8/2003 | Kester et al. |
| 6,784,298 B2 | 8/2004 | Goodnow, Jr. et al. |
| 6,911,545 B2 | 6/2005 | Corbett et al. |
| 7,105,671 B2 | 9/2006 | Corbett et al. |
| 7,259,166 B2 | 8/2007 | Corbett et al. |
| 7,262,196 B2 | 8/2007 | Fyfe et al. |
| 2001/0051731 A1 | 12/2001 | Bizzarro et al. |
| 2001/0053851 A1 | 12/2001 | Mahaney |
| 2001/0056191 A1 | 12/2001 | Goodnow, Jr. et al. |
| 2002/0002190 A1 | 1/2002 | Corbett et al. |
| 2002/0035266 A1 | 3/2002 | Sidduri |
| 2002/0035267 A1 | 3/2002 | Sidduri |
| 2002/0042512 A1 | 4/2002 | Kester et al. |
| 2002/0065275 A1 | 5/2002 | Sidduri |
| 2002/0082260 A1 | 6/2002 | Guertin |
| 2002/0103199 A1 | 8/2002 | Corbett et al. |
| 2002/0103241 A1 | 8/2002 | Corbett et al. |
| 2002/0107396 A1 | 8/2002 | Corbett et al. |
| 2002/0111372 A1 | 8/2002 | Corbett et al. |
| 2002/0198200 A1 | 12/2002 | Kester et al. |
| 2003/0060625 A1 | 3/2003 | Bizzarro et al. |
| 2003/0225283 A1 | 12/2003 | Corbett et al. |
| 2003/0225286 A1 | 12/2003 | Goodnow, Jr. et al. |
| 2003/0235551 A1 | 12/2003 | Pagilagan |
| 2004/0147748 A1 | 7/2004 | Chen et al. |
| 2004/0181067 A1 | 9/2004 | Fyfe et al. |
| 2004/0186290 A1 | 9/2004 | Fyfe et al. |
| 2005/0282851 A1 | 12/2005 | Bebernitz |
| 2006/0141599 A1 | 6/2006 | Corbett et al. |
| 2006/0178429 A1 | 8/2006 | Corbett et al. |
| 2007/0129554 A1 | 6/2007 | Harrington et al. |
| 2007/0265297 A1 | 11/2007 | Bebernitz et al. |
| 2008/0009465 A1 | 1/2008 | Ryono et al. |
| 2008/0015358 A1 | 1/2008 | Fyfe et al. |
| 2008/0021032 A1 | 1/2008 | Berthel et al. |
| 2008/0021052 A1 | 1/2008 | Chen et al. |
| 2008/0103167 A1 | 5/2008 | Bebernitz et al. |
| 2008/0139562 A1 | 6/2008 | Jeppesen et al. |
| 2008/0242869 A1 | 10/2008 | Fyfe |
| 2008/0293730 A1 | 11/2008 | Fyfe et al. |
| 2008/0293741 A1 | 11/2008 | Fyfe et al. |
| 2008/0312256 A1 | 12/2008 | Bebernitz et al. |
| 2008/0318948 A1 | 12/2008 | Bebernitz |
| 2009/0005391 A1 | 1/2009 | Fyfe et al. |
| 2009/0054444 A1 | 2/2009 | Fyfe et al. |
| 2009/0281142 A1* | 11/2009 | Hayakawa et al. ............ 514/314 |
| 2010/0016304 A1 | 1/2010 | Fukuda et al. |
| 2010/0099671 A1 | 4/2010 | Fukuda et al. |
| 2010/0286171 A1* | 11/2010 | Hayakawa et al. ....... 514/255.05 |

FOREIGN PATENT DOCUMENTS

| | | |
|---|---|---|
| WO | 01/83465 | 11/2001 |
| WO | 01/83478 | 11/2001 |
| WO | 01/85706 | 11/2001 |
| WO | 01/85707 | 11/2001 |
| WO | 02/08209 | 1/2002 |
| WO | 02/14312 | 2/2002 |
| WO | 02/46173 | 6/2002 |
| WO | 02/48106 | 6/2002 |
| WO | 03/095438 | 11/2003 |
| WO | 2004/050645 | 6/2004 |
| WO | 2004/052869 | 6/2004 |
| WO | 2004/063194 | 7/2004 |
| WO | 2004/072031 | 8/2004 |
| WO | 2004/072066 | 8/2004 |
| WO | 2005/095417 | 10/2005 |
| WO | 2005/095418 | 10/2005 |
| WO | 2005/103021 | 11/2005 |
| WO | 2006/016174 | 2/2006 |
| WO | 2006/016178 | 2/2006 |
| WO | 2006/016194 | 2/2006 |
| WO | 2006/058923 | 6/2006 |
| WO | 2006/059163 | 6/2006 |
| WO | 2007/026761 | 3/2007 |
| WO | 2007/041365 | 4/2007 |
| WO | 2007/041366 | 4/2007 |
| WO | 2007/048717 | 5/2007 |
| WO | 2007/051845 | 5/2007 |
| WO | 2007/051846 | 5/2007 |
| WO | 2007/051847 | 5/2007 |
| WO | 2008/005914 | 1/2008 |
| WO | 2008/005964 | 1/2008 |
| WO | 2008/012227 | 1/2008 |
| WO | 2008/078674 | 7/2008 |
| WO | 2008/111473 | 9/2008 |
| WO | 2008/119734 | 10/2008 |
| WO | 2009/091014 | 7/2009 |

OTHER PUBLICATIONS

International Preliminary Report on Patentability together with English translation of the Written Opinion dated Dec. 23, 2010 issued in International Application No. PCT/JP2009/001907.

* cited by examiner

CYCLOPENTYLACRYLAMIDE DERIVATIVE

TECHNICAL FIELD

The present invention relates to an activator of glucokinase (which may be abbreviated as GK). The present invention also relates to a pharmaceutical composition for the treatment or prevention of diabetes, obesity, and the like that contain the GK activator as an active ingredient.

BACKGROUND ART

According to a patient survey conducted by the Japanese Ministry of Health, Labor and Welfare in Heisei 14 (2002), the total number of diabetes patients in Japan was 2.28 million. Moreover, according to a diabetes survey conducted in the same year, the total number of people "strongly suspected of having diabetes" and people in whom "the possibility of diabetes cannot be denied" had increased to 16.20 million, and this increase has been perceived as a problem.

Since the insulin secretory capacity of Japanese is low due to genetic factors, the Japanese domestic market is mainly for impaired insulin secretion. However, due to the westernization of Japanese dietary habits, the number of patients with insulin resistance is gradually increasing in recent years. Accordingly, there is a demand for drugs that are expected to be effective for both impaired insulin secretion and insulin resistance.

Glucokinase (GK), which catalyzes the phosphorylation of glucose, functions as a glucose sensor in the body and increases glucose utilization in the liver and the secretion of insulin in a high glucose state. In diabetes patients, the homeostasis of glucose concentration in the body is not maintained in a normal state. Therefore, by activating GK, insulin secretion from the pancreas, which depends on the concentration of glucose, is facilitated. In the lever, the activation of GK increases the glucose utilization and suppresses glucose output. This dual action reduces the blood glucose level (Non-Patent Documents 1 to 3). Therefore, it is desirable to provide GK activators useful as diabetes drugs that are effective for both impaired insulin secretion (action in the pancreas) and insulin resistance (action in the liver).

Various amide compounds are known as GK activators. Examples of such amide compounds include: aryl cycloalkyl propionamides (Patent Document 1); 2,3-di-substituted trans olefinic N-heteroaromatic or ureido propionamides (Patent Document 2); alkynyl phenyl heteroaromatic amides (Patent Document 3); hydantoins (Patent Document 4); substituted phenylacetamides (Patent Document 5); para-alkyl, aryl, cycloheteroalkyl or heteroaryl (carbonyl or sulfonyl)amino substituted phenyl amides (Patent Document 6); alpha-acyl and alpha-heteroatom-substituted benzene acetamides (Patent Document 7); tetrazolyl-phenyl acetamides (Patent Document 8); fused heteroaromatic compounds (Patent Document 9); phenylacetamides having a cycloalkane with a single carbon atom substituted or a heterocycle (Patent Document 10); and other amide compounds (Patent Documents 11 to 21). However, these patent documents do not disclose acrylamide compounds in which two fluorine atoms are attached to different carbon atoms of a cyclopentyl group.

PRIOR ART DOCUMENT

Patent Document

[Patent Document 1] WO2000/058293 pamphlet
[Patent Document 2] WO2001/044216 pamphlet
[Patent Document 3] WO2001/083465 pamphlet
[Patent Document 4] WO2001/083478 pamphlet
[Patent Document 5] WO2001/085706 pamphlet
[Patent Document 6] WO2001/085707 pamphlet
[Patent Document 7] WO2002/008209 pamphlet
[Patent Document 8] WO2002/014312 pamphlet
[Patent Document 9] WO2002/046173 pamphlet
[Patent Document 10] WO2003/095438 pamphlet
[Patent Document 11] WO2004/052869 pamphlet
[Patent Document 12] WO2004/072031 pamphlet
[Patent Document 13] WO2004/072066 pamphlet
[Patent Document 14] WO2005/103021 pamphlet
[Patent Document 15] WO2006/016174 pamphlet
[Patent Document 16] WO2006/016178 pamphlet
[Patent Document 17] WO2006/016194 pamphlet
[Patent Document 18] WO2006/059163 pamphlet
[Patent Document 19] U.S. Pat. No. 6,911,545
[Patent Document 20] WO2007/026761 pamphlet
[Patent Document 21] WO2008/012227 pamphlet Non-Patent Document

[Non-Patent Document 1] Diabetes 45, 223-241 (1996)
[Non-Patent Document 2] Diabetes 41, 792-806 (1992)
[Non-Patent Document 3] FASEB J.10, 1213-1218 (1996)

SUMMARY OF THE INVENTION

Problems to be Solved by the Invention

It is an object of the present invention to provide compounds having an excellent GK activating effect or an excellent hypoglycemic effect and to make use of the compounds for the treatment or prevention of diabetes, obesity, and the like.

Means for Solving the Problems

The present inventors have conducted extensive studies to solve the above problems and found that, among acrylamide compounds having a 3,4-difluorocyclopentyl group at 3-position thereof, compounds having specific stereo structures have excellent GK activating and hypoglycemic effects. Thus, the present invention has been completed.

Accordingly, the present invention relates to the following:
(1) A compound represented by the general formula (1) or a pharmaceutically acceptable salt thereof:

[Chemical formula 1]

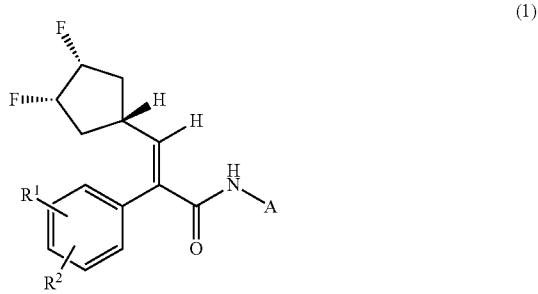

(1)

(wherein $R^1$ and $R^2$ are each independently a hydrogen atom, a halogen atom, an amino group, a hydroxyl group, a hydroxyamino group, a nitro group, a cyano group, a sulfamoyl group, a $C_1$ to $C_6$ alkyl group, a $C_1$ to $C_6$ alkoxy group, a $C_1$ to $C_6$ alkylsulfanyl group, a $C_1$ to $C_6$ alkylsulfinyl group, a $C_1$ to $C_6$ alkylsulfonyl group, or a $C_1$ to $C_6$ alkoxy-$C_1$ to $C_6$ alkylsulfonyl group, and A is a substituted or unsubstituted heteroaryl group).

(2) The compound according to (1) or a pharmaceutically acceptable salt thereof, wherein $R^1$ and $R^2$ are each independently a hydrogen atom, a halogen atom, or a $C_1$ to $C_6$ alkylsulfonyl group.

(3) The compound according to (1) or a pharmaceutically acceptable salt thereof, wherein $R^1$ is a hydrogen atom or a halogen atom, and $R^2$ is a $C_1$ to $C_6$ alkylsulfonyl group.

(4) The compound according to (1) or a pharmaceutically acceptable salt thereof, wherein $R^1$ is a hydrogen atom and $R^2$ is a $C_1$ to $C_6$ alkylsulfonyl group.

(5) The compound according to (1) or a pharmaceutically acceptable salt thereof, wherein $R^1$ is a hydrogen atom, and $R^2$ is a cyclopropylsulfonyl group.

(6) The compound according to (1) or a pharmaceutically acceptable salt thereof, wherein $R^1$ is a hydrogen atom, and $R^2$ is a methylsulfonyl group.

(7) The compound according to any of (1) to (6) or a pharmaceutically acceptable salt thereof, wherein the compound is represented by the general formula (1a):

[Chemical formula 2]

(1a)

(wherein $R^1$, $R^2$, and A are as defined in (1)).

(8) The compound according to any of (1) to (6) or a pharmaceutically acceptable salt thereof, wherein the compound is represented by the general formula (1b):

[Chemical formula 3]

(1b)

(wherein $R^1$, $R^2$, and A are as defined in (1)).

(9) The compound according to any of (1) to (8) or a pharmaceutically acceptable salt thereof, wherein A is an unsubstituted heteroaryl group or a heteroaryl group that is mono-substituted with a halogen atom, a $C_1$ to $C_6$ alkyl group optionally substituted with a halogen atom or a hydroxyl group, a $C_1$ to $C_6$ alkoxy group optionally substituted with a halogen atom or a hydroxyl group, a nitro group, a cyano group, or a group represented by the formula of $-(O)_p(CH_2)_mC(O)OR^3$ (wherein $R^3$ is a hydrogen atom or a $C_1$ to $C_6$ alkyl group, m is an integer of 0 to 2, and p is 0 or 1).

(10) The compound according to any of (1) to (8) or a pharmaceutically acceptable salt thereof, wherein A is a heteroaryl group that is mono-substituted with a halogen atom, a $C_1$ to $C_6$ alkyl group, or a $C_1$ to $C_6$ hydroxyalkyl group.

(11) The compound according to any of (1) to (8) or a pharmaceutically acceptable salt thereof, wherein A is a heteroaryl group that is mono-substituted with a $C_1$ to $C_6$ alkoxy group optionally substituted with a halogen atom or a hydroxyl group, or a $C_1$ to $C_3$ alkoxy-$C_1$ to $C_3$ alkoxy group.

(12) The compound according to any of (1) to (8) or a pharmaceutically acceptable salt thereof, wherein A is a heteroaryl group that is mono-substituted with a $C_1$ to $C_6$ alkylsulfanyl group that is optionally substituted with a halogen atom or a hydroxyl group.

(13) The compound according to any of (9) to (12) or a pharmaceutically acceptable salt thereof, wherein A is an unsubstituted or mono-substituted five- or six-membered heteroaromatic ring, the heteroaromatic ring containing 1 to 3 heteroatoms selected from a sulfur atom, an oxygen atom, and a nitrogen atom, one of which is a nitrogen atom adjacent to a ring-connecting atom.

(14) The compound according to any of (9) to (12) or a pharmaceutically acceptable salt thereof, wherein A is an unsubstituted or mono-substituted fused heterocycle having a five- or six-membered heteroaromatic ring, the heteroaromatic ring containing 1 to 3 heteroatoms selected from a sulfur atom, an oxygen atom, and a nitrogen atom, one of the heteroatoms being a nitrogen atom adjacent to a ring-connecting atom.

(15) The compound according to any of (9) to (12) or a pharmaceutically acceptable salt thereof, wherein A is an unsubstituted or substituted heteroaromatic ring selected from the following rings:

[Chemical formula 4]

-continued

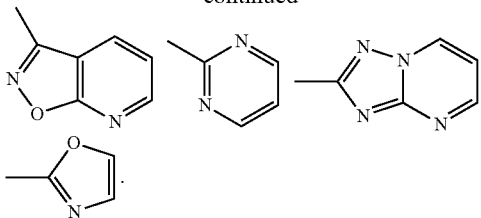

(16) The compound according to (1), or a pharmaceutically acceptable salt thereof, selected from the group consisting of (E)-3-[(1α, 3α,4α)-3,4-difluorocyclopentyl]-N-(5-fluorothiazol-2-yl)-2-(4-(methylsulfonyl)phenyl)acrylamide, (E)-N-(5-chlorothiazol-2-yl)-3-[(1α,3α,4α)-3,4-difluorocyclopentyl]-2-(4-(methylsulfonyl)phenyl)acryl amide, (E)-3-[(1α,3α,4α)-3,4-difluorocyclopentyl]-2-(4-(methylsulfonyl)phenyl)-N-(4-methylthiazol-2-yl)acrylamide, (E)-3-[(1α,3α,4α)-3,4-difluorocyclopentyl]-2-(4-(methylsulfonyl)phenyl)-N-(5-methylthiazol-2-yl)acrylamide, (+)-(E)-3-[(1α,3α,4α)-3,4-difluorocyclopentyl]-N-[4-(2,2-dimethyl-1,3-dioxolan-4-yl)thiazol-2-yl]-2-(4-(methylsulfonyl)phenyl)acrylamide, (−)-(E)-3-[(1α,3α,4α)-3,4-difluorocyclopentyl]-N-[4-(2,2-dimethyl-1,3-dioxolan-4-yl)thiazol-2-yl]-2-(4-(methylsulfonyl)phenyl)acrylamide, (+)-(E)-3-[(1α,3α,4α)-3,4-difluorocyclopentyl]-N-[4-(1,2-dihydroxyethyl)thiazol-2-yl]-2-(4-(methylsulfonyl)phenyl)acrylamide, (−)-(E)-3-[(1α,3α,4α)-3,4-difluorocyclopentyl]-N-[4-(1,2-dihydroxyethyl)thiazol-2-yl]-2-(4-(methylsulfonyl)phenyl)acrylamide, (E)-N-[4-tert-butylthiazol-2-yl]-3-[(1α,3α,4α)-3,4-difluorocyclopentyl]-2-(4-(methylsulfonyl)phenyl)acryl amide, (E)-3-[(1α,3α,4α)-3,4-difluorocyclopentyl]-2-(4-(methylsulfonyl)phenyl)-N-{4-[2-(tetrahydro-2H-pyran-2-yloxy)ethyl]thiazol-2-yl}acrylamide, (E)-3-[(1α,3α,4α)-3,4-difluorocyclopentyl]-N-[4-(2-hydroxyethyl)thiazol-2-yl]-2-(4-(methylsulfonyl)phenyl)acrylamide, (E)-3-[(1α,3α,4α)-3,4-difluorocyclopentyl]-N-[5-(N,N-dimethylsulfamoyl)thiazol-2-yl]-2-(4-(methylsulfonyl)phenyl)acrylamide, (E)-3-[(1α,3α,4α)-3,4-difluorocyclopentyl]-N-[5-(4-methylpiperazine-1-ylsulfonyl)thiazol-2-yl]-2-(4-(methylsulfonyl)phenyl)acrylamide, (E)-3-[(1α,3α,4α)-3,4-difluorocyclopentyl]-2-(4-(methylsulfonyl)phenyl)-N-(1,2,4-thiadiazol-5-yl)acrylamide, (E)-3-[(1α,3α,4α)-3,4-difluorocyclopentyl]-2-(4-(methylsulfonyl)phenyl)-N-(3-methyl-1,2,4-thiadiazol-5-yl)acrylamide, (E)-3-[(1α,3α,4α)-3,4-difluorocyclopentyl]-N-(3-ethyl-1,2,4-thiadiazol-5-yl)-2-(4-(methylsulfonyl)phenyl)acrylamide, (E)-3-[(1α,3α,4α)-3,4-difluorocyclopentyl]-N-(3-methoxy-1,2,4-thiadiazol-5-yl)-2-(4-(methylsulfonyl)phenyl)acrylamide, (E)-3-[(1α,3α,4α)-3,4-difluorocyclopentyl]-2-(4-(methylsulfonyl)phenyl)-N-(pyridin-2-yl)acrylamide, (E)-3-[(1α,3α,4α)-3,4-difluorocyclopentyl]-N-(5-fluoropyridin-2-yl)-2-(4-(methylsulfonyl)phenyl)acrylamide, (E)-N-(5-chloropyridin-2-yl)-3-[(1α,3α,4α)-3,4-difluorocyclopentyl]-2-(4-(methylsulfonyl)phenyl)acrylamide, (E)-3-[(1α,3α,4α)-3,4-difluorocyclopentyl]-2-(4-(methylsulfonyl)phenyl)-N-[5-(methylthio)pyridin-2-yl]acrylamide, (E)-N-(5-cyclopropylpyridin-2-yl)-3-[(1α,3α,4α)-3,4-difluorocyclopentyl]-2-(4-(methylsulfonyl)phenyl)acryl amide, (E)-3-[(1α,3α,4α)-3,4-difluorocyclopentyl]-N-[5-(hydroxymethyl)pyridin-2-yl]-2-(4-(methylsulfonyl)phenyl)acrylamide, (E)-3-[(1α,3α,4α)-3,4-difluorocyclopentyl]-N-[5-(N,N-dimethylsulfamoyl)pyridin-2-yl]-2-(4-(methylsulfonyl)phenyl)acrylamide, (E)-3-[(1α,3α,4α)-3,4-difluorocyclopentyl]-2-(4-(methylsulfonyl)phenyl)-N-(pyrazin-2-yl)acrylamide, (E)-3-[(1α,3α,4α)-3,4-difluorocyclopentyl]-N-(5-methylpyrazin-2-yl)-2-(4-(methylsulfonyl)phenyl)acrylamide, (E)-3-[(1α,3α,4α)-3,4-difluorocyclopentyl]-N-(5-ethylpyrazin-2-yl)-2-(4-(methylsulfonyl)phenyl)acrylamide, (E)-3-[(1α,3α,4α)-3,4-difluorocyclopentyl]-N-(5-methoxypyrazin-2-yl)-2-(4-(methylsulfonyl)phenyl)acrylamide, (E)-3-[(1α,3α,4α)-3,4-difluorocyclopentyl]-N-[5-(2-methylethoxy)pyrazin-2-yl]-2-(4-(methylsulfonyl)phenyl)acrylamide, (E)-3-[(1α,3α,4α)-3,4-difluorocyclopentyl]-N-[5-(2-methoxyethoxy)pyrazin-2-yl]-2-(4-(methylsulfonyl)phenyl)acrylamide, (E)-3-[(1α,3α,4α)-3,4-difluorocyclopentyl]-N-[5-(3-methoxypropoxy)pyrazin-2-yl]-2-(4-(methylsulfonyl)phenyl)acrylamide, (E)-3-[(1α,3α,4α)-3,4-difluorocyclopentyl]-N-[5-(2-ethoxyethoxy)pyrazin-2-yl]-2-(4-(methylsulfonyl)phenyl)acrylamide, (E)-3-[(1α,3α,4α)-3,4-difluorocyclopentyl]-2-(4-(methylsulfonyl)phenyl)-N-{5-[2-(methylthio)ethoxy]pyrazin-2-yl}acrylamide, (E)-2-(4-(methylsulfonyl)phenyl)-3-[(1α,3α,4α)-3,4-difluorocyclopentyl]-N-[5-(2-hydroxyethylthio)pyrazin-2-yl]acrylamide, (E)-3-[(1α,3α,4α)-3,4-difluorocyclopentyl]-2-(4-(methylsulfonyl)phenyl)-N-{5-[2-(tetrahydro-2H-pyran-2-yloxy)ethoxy]pyrazin-2-yl}acrylamide, (E)-3-[(1α,3α,4α)-3,4-difluorocyclopentyl]-N-[5-(2-(hydroxyethoxy)pyrazin-2-yl]-2-(4-(methylsulfonyl)phenyl)acrylamide, (E)-3-[(1α,3α,4α)-3,4-difluorocyclopentyl]-N-{5-[(4R)-2,2-dimethyl-1,3-dioxolan-4-yl]pyrazin-2-yl}-2-(4-(methylsulfonyl)phenyl)acrylamide, (E)-3-[(1α,3α,4α)-3,4-difluorocyclopentyl]-N-{5-[(4S)-2,2-dimethyl-1,3-dioxolan-4-yl]pyrazin-2-yl}-2-(4-(methylsulfonyl)phenyl)acrylamide, (E)-3-[(1α,3α,4α)-3,4-difluorocyclopentyl]-N-{5-[(2R)-1,2-dihydroxyethyl]pyrazin-2-yl}-2-(4-(methylsulfonyl)phenyl)acrylamide, (E)-3-[(1α,3α,4α)-3,4-difluorocyclopentyl]-N-{5-[(2S)-1,2-dihydroxyethyl]pyrazin-2-yl}-2-(4-(methylsulfonyl)phenyl)acrylamide, diethyl 5-{(E)-3-[(1α,3α,4α)-3,4-difluorocyclopentyl-2-(4-(methylsulfonyl)phenyl)]acrylamide}pyrazin-2-ylphosphonate, diethyl (5-{(E)-3-[(1α,3α,4α)-3,4-difluorocyclopentyl-2-(4-(methylsulfonyl)phenyl)]acrylamide}pyrazin-2-yl)methylphosphonate, (E)-3-[(1α,3α,4α)-3,4-difluorocyclopentyl]-N-[1-methyl-1H-pyrazol-3-yl]-2-(4-(methylsulfonyl)phenyl)acrylamide, (E)-3-[(1α,3α,4α)-3,4-difluorocyclopentyl]-N-[1-ethyl-1H-pyrazol-3-yl]-2-(4-(methylsulfonyl)phenyl)acrylamide, (E)-3-[(1α,3α,4α)-3,4-difluorocyclopentyl]-N-[1-(difluoromethyl)-1H-pyrazol-3-yl]-2-(4-(methylsulfonyl)phenyl)acrylamide, (E)-3-[(1α,3α,4α)-3,4-difluorocyclopentyl]-N-[1-(2-fluoroethyl)-1H-pyrazol-3-yl]-2-(4-(methylsulfonyl)phenyl)acrylamide, (E)-3-[(1α,3α,4α)-3,4-difluorocyclopentyl]-2-(4-(methylsulfonyl)phenyl)-N-[1-(2,2,2-trifluoroethyl)-1H-pyrazol-3-yl]acrylamide, (E)-3-[(1α,3 α,4α)-3,4-difluorocyclopentyl]-N-[1-(2-hydroxyethyl)-1H-pyrazol-3-yl]-2-(4-(methylsulfonyl)phenyl)acrylamide, (E)-3-[(1α,3α,4α)-3,4-difluorocyclopentyl]-N-[1-(2-hydroxy-2-methylpropyl)-1H-pyrazol-3-yl]-2-(4-(methylsulfonyl)phenyl)acrylamide, (E)-3-[(1α,3α,4α)-3,4-difluorocyclopentyl]-N-(1-{[(4R)-2,2-dimethyl-1,3-dioxolan-4-yl]methyl}-1H-pyrazol-3-yl)-2-(4-(methylsulfonyl)phenyl)acrylamide, (E)-3-[(1α,3α,4α)-3,4-difluorocyclopentyl]-N-(1-{[(4S)-2,2-dimethyl-1,3-dioxolan-4-yl]methyl}-1H-pyrazol-3-yl)-2-(4-(methylsulfonyl)phenyl)acrylamide, (E)-3-[(1α,3α,4α)-3,4-difluorocyclopentyl]-N-{1-[(2R)-2,3-dihydroxypropyl]-1H-pyrazol-3-yl}-2-(4-(methylsulfonyl)phenyl)acrylamide, (E)-3-[(1α,3α,4α)-3,4-difluorocyclopentyl]-N-{1-[(2S)-2,3-dihydroxypropyl]-1H-pyrazol-3-yl}-2-(4-(methylsulfonyl)

phenyl)acrylamide, (E)-3-[(1α,3α,4α)-3,4-difluorocyclopentyl]-N-(isoxazol-3-yl)-2-(4-(methylsulfonyl)phenyl)acrylamide, (E)-3-[(1α,3α,4α)-3,4-difluorocyclopentyl]-N-(6-methoxybenzo[d]thiazol-2-yl)-2-(4-(methylsulfonyl)phenyl)acrylamide, (E)-3-[(1α,3α,4α)-3,4-difluorocyclopentyl]-N-[6-(difluoromethoxy)benzo[d]thiazol-2-yl]-2-(4-(methylsulfonyl)phenyl)acrylamide, (E)-3-[(1α,3α,4α)-3,4-difluorocyclopentyl]-N-[5-(2-methoxyethoxy)thiazolo[5,4-b]pyridin-2-yl]-2-(4-(methylsulfonyl)phenyl)acrylamide, and ethyl (E)-2-{2-[(R)-2-(4-(methylsulfonyl)phenyl)-3-[(1α,3α,4α)-3,4-difluorocyclopentyl]acrylamide]thiazolo[5,4-b]pyridin-2-yloxy}acetate.

(17) The compound according to (1), or a pharmaceutically acceptable salt thereof, selected from the group consisting of (E)-2-(4-(cyclopropylsulfonyl)phenyl)-3-[(1α,3α,4α)-3,4-difluorocyclopentyl]-N-(5-fluorothiazol-2-yl)acrylamide, (E)-N-(5-bromothiazol-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-(4-methylthiazol-2-yl)acrylamide, (E)-2-(4-(cyclopropylsulfonyl)phenyl)-3-[(1α,3α,4α)-3,4-difluorocyclopentyl]-N-(5-methylthiazol-2-yl)acrylamide, (+)-(E)-2-(4-(cyclopropylsulfonyl)phenyl)-3-[(1α,3α,4α)-3,4-difluorocyclopentyl]-N-[4-(2,2-dimethyl-1,3-dioxolan-4-yl)thiazol-2-yl]acrylamide, (−)-(E)-2-(4-(cyclopropylsulfonyl)phenyl)-3-[(1α,3α,4α)-3,4-difluorocyclopentyl]-N-[4-(2,2-dimethyl-1,3-dioxolan-4-yl)thiazol-2-yl]acrylamide, (E)-N-(4-tert-butylthiazol-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-[5-(4-methylpiperazin-1-ylsulfonyl)thiazol-2-yl]acrylamide, methyl 3-{2-[(E)-2-(4-(cyclopropylsulfonyl)phenyl)-3-[(1α,3α,4α)-3,4-difluorocyclopentyl]acrylamide]thiazol-4-yl}propionate, (E)-2-(4-(cyclopropylsulfonyl)phenyl)-3-[(1α,3α,4α)-3,4-difluorocyclopentyl]-N-(1,2,4-thiadiazol-5-yl)acrylamide, (E)-2-(4-(cyclopropylsulfonyl)phenyl)-3-[(1α,3α,4α)-3,4-difluorocyclopentyl]-N-(3-methyl-1,2,4-thiadiazol-5-yl)acrylamide, (E)-2-(4-(cyclopropylsulfonyl)phenyl)-3-[(1α,3α,4α)-3,4-difluorocyclopentyl]-N-(3-ethyl-1,2,4-thiadiazol-5-yl)acrylamide, (E)-2-(4-(cyclopropylsulfonyl)phenyl)-3-[(1α,3α,4α)-3,4-difluorocyclopentyl]-N-(3-phenyl-1,2,4-thiadiazol-5-yl)acrylamide, (E)-2-(4-(cyclopropylsulfonyl)phenyl)-3-[(1α,3α,4α)-3,4-difluorocyclopentyl]-N-(pyridin-2-yl)acrylamide, (E)-2-(4-(cyclopropylsulfonyl)phenyl)-3-[(1α,3α,4α)-3,4-difluorocyclopentyl]-N-[5-(methylthio)pyridin-2-yl]acrylamide, (E)-N-(5-cyclopropylpyridin-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-[5-(hydroxymethyl)pyridin-2-yl]acrylamide, (E)-2-(4-(cyclopropylsulfonyl)phenyl)-3-[(1α,3α,4α)-3,4-difluorocyclopentyl]-N-[5-(N,N-dimethylsulfamoyl)pyridin-2-yl]acrylamide, (E)-2-(4-(cyclopropylsulfonyl)phenyl)-3-[(1α,3α,4α)-3,4-difluorocyclopentyl]-N-(pyrazin-2-yl)acrylamide, (E)-2-(4-(cyclopropylsulfonyl)phenyl)-3-[(1α,3α,4α)-3,4-difluorocyclopentyl]-N-(5-methylpyrazin-2-yl)acrylamide, (E)-2-(4-(cyclopropylsulfonyl)phenyl)-3-[(1α,3α,4α)-3,4-difluorocyclopentyl]-N-(5-ethylpyrazin-2-yl)acrylamide, (E)-2-(4-(cyclopropylsulfonyl)phenyl)-3-[(1α,3α,4α)-3,4-difluorocyclopentyl]-N-(5-methoxypyrazin-2-yl)acrylamide, (E)-2-(4-(cyclopropylsulfonyl)phenyl)-3-[(1α,3α,4α)-3,4-difluorocyclopentyl]-N-[5-(methylthio)pyrazin-2-yl]acrylamide, (E)-2-(4-(cyclopropylsulfonyl)phenyl)-3-[(1α,3α,4α)-3,4-difluorocyclopentyl]-N-[5-(2-methylethoxy)pyrazin-2-yl]acrylamide, (E)-2-(4-(cyclopropylsulfonyl)phenyl)-3-[(1α,3α,4α)-3,4-difluorocyclopentyl]-N-[5-(2-methoxyethoxy)pyrazin-2-yl]acrylamide, (E)-2-(4-(cyclopropylsulfonyl)phenyl)-3-[(1α,3α,4α)-3,4-difluorocyclopentyl]-N-[5-(3-methoxypropoxy)pyrazin-2-yl]acrylamide, (E)-2-(4-(cyclopropylsulfonyl)phenyl)-3-[(1α,3α,4α)-3,4-difluorocyclopentyl]-N-[5-(2-ethoxyethoxy)pyrazin-2-yl]acrylamide, (E)-2-(4-(cyclopropylsulfonyl)phenyl)-3-[(1α,3α,4α)-3,4-difluorocyclopentyl]-N-{5-[2-(methylthio)ethoxy]pyrazin-2-yl}acrylamide, (E)-2-(4-(cyclopropylsulfonyl)phenyl)-3-[(1α,3α,4α)-3,4-difluorocyclopentyl]-N-{5-[2-(tetrahydro-2H-pyran-2-yloxy)ethoxy]pyrazin-2-yl}acrylamide, (E)-2-(4-(cyclopropylsulfonyl)phenyl)-3-[(1α,3α,4α)-3,4-difluorocyclopentyl]-N-[5-(2-hydroxyethoxy)pyrazin-2-yl]acrylamide, (E)-2-(4-(cyclopropylsulfonyl)phenyl)-3-[(1α,3α,4α)-3,4-difluorocyclopentyl]-N-{5-[(4R)-2,2-dimethyl-1,3-dioxolan-4-yl]pyrazin-2-yl}acrylamide, (E)-2-(4-(cyclopropylsulfonyl)phenyl)-3-[(1α,3α,4α)-3,4-difluorocyclopentyl]-N-{5-[(4S)-2,2-dimethyl-1,3-dioxolan-4-yl]pyrazin-2-yl}acrylamide, (E)-2-(4-(cyclopropylsulfonyl)phenyl)-3-[(1α,3α,4α)-3,4-difluorocyclopentyl]-N-{5-[(2R)-1,2-dihydroxyethyl]pyrazin-2-yl}acrylamide, (E)-2-(4-(cyclopropylsulfonyl)phenyl)-3-[(1α,3α,4α)-3,4-difluorocyclopentyl]-N-{5-[(2S)-1,2-dihydroxyethyl]pyrazin-2-yl}acrylamide, diethyl 5-{(E)-2-(4-(cyclopropylsulfonyl)phenyl)-3-[(1α,3α,4α)-3,4-difluorocyclopentyl]acrylamide}pyrazin-2-yl phosphonate, diethyl (5-{(E)-2-(4-(cyclopropylsulfonyl)phenyl)-3-[(1α,3α,4α)-3,4-difluorocyclopentyl]acrylamide}pyrazin-2-yl methylphosphonate, (E)-2-(4-(cyclopropylsulfonyl)phenyl)-3-[(1α,3α,4α)-3,4-difluorocyclopentyl]-N-(1-methyl-1H-pyrazol-3-yl)acrylamide, (E)-2-(4-(cyclopropylsulfonyl)phenyl)-3-[(1α,3α,4α)-3,4-difluorocyclopentyl]-N-(1-ethyl-1H-pyrazol-3-yl)acrylamide, (E)-2-(4-(cyclopropylsulfonyl)phenyl)-3-[(1α,3α,4α)-3,4-difluorocyclopentyl]-N-(1-(2-fluoroethyl)-1H-pyrazol-3-yl)acrylamide, (E)-2-(4-(cyclopropylsulfonyl)phenyl)-3-[(1α,3α,4α)-3,4-difluorocyclopentyl]-N-[1-(2-hydroxyethyl)-1H-pyrazol-3-yl]acrylamide, (E)-2-(4-(cyclopropylsulfonyl)phenyl)-3-[(1α,3α,4α)-3,4-difluorocyclopentyl]-N-[1-(2-hydroxy-2-methylpropyl)-1H-pyrazol-3-yl]acrylamide, (E)-2-(4-(cyclopropylsulfonyl)phenyl)-3-[(1α,3α,4α)-3,4-difluorocyclopentyl]-N-(1-{[(4R)-2,2-dimethyl-1,3-dioxolan-4-yl]methyl}-1H-pyrazol-3-yl)acrylamide, (E)-2-(4-(cyclopropylsulfonyl)phenyl)-3-[(1α,3α,4α)-3,4-difluorocyclopentyl]-N-{1-{[(4S)-2,2-dimethyl-1,3-dioxolan-4-yl]methyl}-1H-pyrazol-3-yl}acrylamide, (E)-2-(4-(cyclopropylsulfonyl)phenyl)-3-[(1α,3α,4α)-3,4-difluorocyclopentyl]-N-{1-[(2R)-2,3-dihydroxypropyl]-1 H-pyrazol-3-yl}acrylamide, (E)-2-(4-(cyclopropylsulfonyl)phenyl)-3-[(1α,3α,4α)-3,4-difluorocyclopentyl]-N-(1-{[(4S)-2,2-dimethyl-1,3-dioxolan-4-yl]methyl}-1H-pyrazol-3-yl)acrylamide, (E)-2-(4-(cyclopropylsulfonyl)phenyl)-3-[(1α,3α,4α)-3,4-difluorocyclopentyl]-N-(isoxazol-3-yl)acrylamide, (E)-N-(benzo[d]thiazol-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-(6-methoxybenzo[d]thiazol-2-yl)acrylamide, (E)-2-(4-(cyclopropylsulfonyl)phenyl)-3-[(1α,3α,4α)-3,4-difluorocyclopentyl]-N-[6-difluoromethoxy]benzo[d]thiazol-2-yl]acrylamide, (E)-2-(4-(cyclopropylsulfonyl)phenyl)-3-[(1α,3α,4α)-3,4-difluorocyclopentyl]-N-(6-fluorobenzo[d]thiazol-2-yl)

acrylamide, 2-methylethyl 2-{(E)-2-(4-(cyclopropylsulfonyl)phenyl)-3-[(1α,3α,4α)-3,4-difluorocyclopentyl]acrylamide}benzo[d]thiazol-6-carboxylic acid, (E)-2-(4-(cyclopropylsulfonyl)phenyl)-3-[(1α,3α,4α)-3,4-difluorocyclopentyl]-N-(thiazolo[5,4-b]pyridin-2-yl)acrylamide, (E)-N-(5-butoxythiazolo[5,4-b]pyridin-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-[5-(2-methoxyethoxy)thiazolo[5,4-b]pyridin-2-yl)acrylamide, and ethyl 2-{2-[(R)-2-(4-(cyclopropylsulfonyl)phenyl)-3-[(1α,3α,4α)-3,4-difluorocyclopentyl]acrylamide]thiazolo[5,4-b]pyridin-5-yloxy}acetate.

(18) The compound according to (1), or a pharmaceutically acceptable salt thereof, selected from the group consisting of (E)-3-[(1α,3α,4α)-3,4-difluorocyclopentyl]-2-[4-(ethylsulfonyl)phenyl]-N-(thiazol-2-yl)acrylamide, (E)-3-[(1α,3α,4α)-3,4-difluorocyclopentyl]-2-[4-(ethylsulfonyl)phenyl]-N-(5-methylpyrazin-2-yl)acrylamide, and (E)-3-[(1α,3α,4α)-3,4-difluorocyclopentyl]-2-[4-(ethylsulfonyl)phenyl]-N-(1-methyl-1H-pyrazol-3-yl)acrylamide.

(19) The compound according to (1), or a pharmaceutically acceptable salt thereof, selected from the group consisting of (E)-3-[(1α,3α,4α)-3,4-difluorocyclopentyl]-2-[4-(2-methoxyethylsulfonyl)phenyl]-N-(thiazol-2-yl)acrylamide, (E)-3-[(1α,3α,4α)-3,4-difluorocyclopentyl]-2-[4-(2-methoxyethylsulfonyl)phenyl]-N-(5-methylpyrazin-2-yl)acrylamide, and (E)-3-[(1α,3α,4α)-3,4-difluorocyclopentyl]-2-[4-(2-methoxyethylsulfonyl)phenyl]-N-(1-methyl-1H-pyrazol-3-yl)acrylamide.

(20) A method for treating or preventing diabetes, comprising administering the compound according to any of (1) to (19) or a pharmaceutically acceptable salt thereof.

(21) Use of a compound according to any of (1) to (19) or a pharmaceutically acceptable salt thereof for manufacturing a pharmaceutical for treatment or prevention of diabetes.

(22) A pharmaceutical composition, comprising the compound according to any of (1) to (19), or a pharmaceutically acceptable salt thereof, and a pharmaceutically acceptable carrier.

(23) A compound represented by the general formula (2):

[Chemical formula 5]

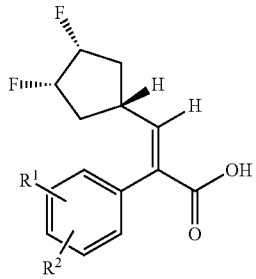

(2)

(wherein $R^1$ and $R^2$ are each independently a hydrogen atom, a halogen atom, an amino group, a hydroxyl group, a hydroxyamino group, a nitro group, a cyano group, a sulfamoyl group, a $C_1$ to $C_6$ alkyl group, a $C_1$ to $C_6$ alkoxy group, a $C_1$ to $C_6$ alkylsulfanyl group, a $C_1$ to $C_6$ alkylsulfinyl group, a $C_1$ to $C_6$ alkylsulfonyl group, or a $C_1$ to $C_6$ alkoxy-$C_1$ to $C_6$ alkylsulfonyl group).

(24) The compound according to (23), wherein $R^1$ is a hydrogen atom, and $R^2$ is a cyclopropylsulfonyl group.

(25) The compound according to (23), wherein $R^1$ is a hydrogen atom, and $R^2$ is a methylsulfonyl group.

ADVANTAGES OF THE INVENTION

According to the present invention, compounds having an excellent GK activating or hypoglycemic effect and few side effects (such as Q-T interval prolongation (relating to hERG current suppression) and insulin-induced hypoglycemia) are provided, and therefore pharmaceuticals excellent for the treatment or prevention of diabetes, obesity, and the like can be provided.

BEST MODE FOR CARRYING OUT THE INVENTION

The term "halogen atom" refers to a fluorine atom, a chlorine atom, a bromine atom, or an iodine atom.

The term "$C_1$ to $C_6$ alkyl group" is a linear or branched alkyl group having 1 to 6 carbon atoms or a cyclic alkyl group having 3 to 6 carbon atoms. Examples of the $C_1$ to $C_6$ alkyl group include a methyl group, an ethyl group, a propyl group, an isopropyl group, a butyl group, an isobutyl group, a sec-butyl group, a tert-butyl group, a cyclopropyl group, and a cyclobutyl group.

The term "$C_1$ to $C_6$ alkoxy group" is a linear or branched alkoxy group having 1 to 6 carbon atoms or a cyclic alkoxy group having 3 to 6 carbon atoms. Examples of the $C_1$ to $C_6$ alkoxy group include a methoxy group, an ethoxy group, a propoxy group, an isopropoxy group, a butoxy group, an isobutoxy group, a sec-butoxy group, a tert-butoxy group, a cyclopropoxy group, and a cyclobutoxy group.

The term "$C_1$ to $C_6$ alkylsulfanyl group" is a linear or branched alkylsulfanyl group having 1 to 6 carbon atoms or a cyclic alkylsulfanyl group having 3 to 6 carbon atoms. Examples of the $C_1$ to $C_6$ alkylsulfanyl group include a methylsulfanyl group, an ethylsulfanyl group, a propylsulfanyl group, an isopropylsulfanyl group, a butylsulfanyl group, an isobutylsulfanyl group, a sec-butylsulfanyl group, a tert-butylsulfanyl group, a cyclopropylsulfanyl group, a cyclobutylsulfanyl group, and a cyclopentylsulfanyl group.

The term "$C_1$ to $C_6$ alkylsulfinyl group" is a linear or branched alkylsulfinyl group having 1 to 6 carbon atoms or a cyclic alkylsulfinyl group having 3 to 6 carbon atoms. Examples of the $C_1$ to $C_6$ alkylsulfinyl group include a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a cyclopropylsulfinyl group, a cyclobutylsulfinyl group, and a cyclopentylsulfinyl group.

The term "$C_1$ to $C_6$ alkylsulfonyl group" is a linear or branched alkylsulfonyl group having 1 to 6 carbon atoms or a cyclic alkylsulfonyl group having 3 to 6 carbon atoms. Examples of the $C_1$ to $C_6$ alkylsulfonyl group include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a cyclopropylsulfonyl group, a cyclobutylsulfonyl group, and a cyclopentylsulfonyl group.

The term "$C_1$ to $C_6$ alkoxy-$C_1$ to $C_6$ alkylsulfonyl group" is a linear or branched alkylsulfonyl group having 1 to 6 carbon atoms that is substituted with a linear or branched alkoxy group having 1 to 6 carbon atoms or with a cyclic alkoxy group having 3 to 6 carbon atoms. Examples thereof include a methoxymethylsulfonyl group, a methoxyethylsulfonyl group, a methoxypropylsulfonyl group, an isopropoxymethylsulfonyl group, and a cyclopropoxy methylsulfonyl group.

The term "heteroaryl group" is a five- or six-membered heteroaromatic ring containing 1 to 3 heteroatoms selected from a sulfur atom, an oxygen atom, and a nitrogen atom as the constituent atom of the ring, and the heteroaromatic ring may optionally form a fused ring with a benzene ring or a five- or six-membered heteroaromatic ring. Preferred examples of the heteroaryl group include a group in which the heteroaromatic ring contains 1 to 3 heteroatoms selected from a sulfur atom, an oxygen atom, and a nitrogen atom and in which one of the heteroatoms is a nitrogen atom adjacent to a ring-connecting atom. The ring-connecting atom is an atom in the ring that is involved in the bond to the nitrogen atom in the amide group, and a carbon atom is preferred as the ring-connecting atom.

Preferred examples of the heteroaryl group include a thiazolyl group, a thiadiazolyl group, a pyrazolyl group, a pyridyl group, a pyrazinyl group, a pyrimidinyl group, a pyridazinyl group, an oxazolyl group, an isoxazolyl group, an imidazolyl group, a triazinyl group, a benzothiazolyl group, a benzoxazolyl group, a benzimidazolyl group, a pyridothiazolyl group, and a quinolinyl group. More preferably, the heteroaryl group is a thiazolyl group, a pyrazolyl group, a pyrazinyl group, a pyridyl group, a thiazolo[5,4-b]pyridinyl group, a thiadiazolyl group, or a pyridothiazolyl group.

Preferably, the "substituted or unsubstituted heteroaryl group" in A is an unsubstituted or mono-substituted heteroaryl group. Examples of the substituent include: halogen atoms; $C_1$ to $C_6$ alkyl groups optionally substituted with a halogen atom or a hydroxyl group (such as a methyl group, a tert-butyl group, a cyclopropyl group, a fluoroethyl group, a difluoromethyl group, and a 1,2-dihydroxyethyl group); $C_1$ to $C_6$ alkoxy groups optionally substituted with a halogen atom or a hydroxyl group; $C_1$ to $C_3$ alkoxy-$C_1$ to $C_3$ alkoxy groups; $C_1$ to $C_3$ alkoxycarbonyl-$C_1$ to $C_3$ alkoxy groups; $C_1$ to $C_3$ alkoxycarbonyl-$C_1$ to $C_6$ alkylsulfanyl groups; $C_1$ to $C_6$ alkylsulfanyl groups; $C_1$ to $C_6$ aminoalkylsulfanyl group optionally substituted with a $C_1$ to $C_3$ alkyl group; $C_1$ to $C_6$ alkylsulfanyl-$C_1$ to $C_6$ alkoxy groups; aryl groups (such as a phenyl group), heteroaryl groups; aliphatic heterocyclyl groups optionally substituted with a $C_1$ to $C_6$ alkyl group (such as a morpholino group and a dioxolyl group); aliphatic heterocyclylcarbonyl groups; aliphatic heterocyclylsulfonyl groups; aliphatic heterocyclyl-$C_1$ to $C_3$ alkyl groups; aliphatic heterocyclyl-$C_1$ to $C_3$ alkoxy group; aliphatic heterocyclyloxy-$C_1$ to $C_3$ alkoxy groups; aminosulfonyl groups optionally substituted with a $C_1$ to $C_3$ alkyl group; $C_1$ to $C_6$ hydroxyalkylsulfanyl groups; a nitro group; a cyano group; groups represented by the formula of

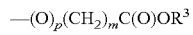
—(O)$_p$(CH$_2$)$_m$C(O)OR$^3$ (wherein R$^3$ is a hydrogen atom, a $C_1$ to $C_6$ alkyl group, or a $C_1$ to $C_3$ alkoxy-$C_1$ to $C_3$ alkyl group, m is an integer of 0 to 2, and p is 0 or 1); and groups represented by the formula of

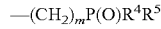
—(CH$_2$)$_m$P(O)R$^4$R$^5$ (wherein R$^4$ and R$^5$ are each independently a hydroxyl group, a $C_1$ to $C_3$ alkyl group, or a $C_1$ to $C_3$ alkoxy group, and m is an integer of 0 to 2).

Examples of the pharmaceutically acceptable salt include salts of inorganic and organic acids such as hydrochloric acid, hydrobromic acid, nitric acid, sulfuric acid, phosphoric acid, citric acid, formic acid, maleic acid, acetic acid, succinic acid, and tartaric acid.

Specific examples of the compound according to the present invention include the following compounds and pharmaceutically acceptable salts thereof. (E)-3-[(1α,3α,4α)-3,4-difluorocyclopentyl]-N-(5-fluorothiazol-2-yl)-2-(4-(methylsulfonyl)phenyl)acrylamide, (E)-N-(5-chlorothiazol-2-yl)-3-[(1α,3α,4α)-3,4-difluorocyclopentyl]-2-(4-(methylsulfonyl)phenyl)acrylamide, (E)-3-[(1α,3α,4α)-3,4-difluorocyclopentyl]-2-(4-(methylsulfonyl)phenyl)-N-(4-methylthiazol-2-yl)acrylamide, (E)-3-[(1α,3α,4α)-3,4-difluorocyclopentyl]-2-(4-(methylsulfonyl)phenyl)-N-(5-methylthiazol-2-yl)acrylamide, (+)-(E)-3-[(1α,3α,4α)-3,4-difluorocyclopentyl]-N-[4-(2,2-dimethyl-1,3-dioxolan-4-yl)thiazol-2-yl]-2-(4-(methylsulfonyl)phenyl)acrylamide, (−)-(E)-3-[(1α,3α,4α)-3,4-difluorocyclopentyl]-N-[4-(2,2-dimethyl-1,3-dioxolan-4-yl)thiazol-2-yl]-2-(4-(methylsulfonyl)phenyl)acrylamide, (+)-(E)-3-[(1α,3α,4α)-3,4-difluorocyclopentyl]-N-[4-(1,2-dihydroxyethyl)thiazol-2-yl]-2-(4-(methylsulfonyl)phenyl)acrylamide, (−)-(E)-3-[(1α,3α,4α)-3,4-difluorocyclopentyl]-N-[4-(1,2-dihydroxyethyl)thiazol-2-yl]-2-(4-(methylsulfonyl)phenyl)acrylamide, (E)-N-[4-tert-butylthiazol-2-yl]-3-[(1α,3α,4α)-3,4-difluorocyclopentyl]-2-(4-(methylsulfonyl)phenyl)acrylamide, (E)-3-[(1α,3α,4α)-3,4-difluorocyclopentyl]-2-(4-(methylsulfonyl)phenyl)-N-(4-[2-(tetrahydro-2H-pyran-2-yloxy)ethyl]thiazol-2-yl)acrylamide, (E)-3-[(1α,3α,4α)-3,4-difluorocyclopentyl]-N-[4-(2-hydroxyethyl)thiazol-2-yl]-2-(4-(methylsulfonyl)phenyl)acrylamide, (E)-3-[(1α,3α,4α)-3,4-difluorocyclopentyl]-N-[5-(N,N-dimethylsulfamoyl)thiazol-2-yl]-2-(4-(methylsulfonyl)phenyl)acrylamide, (E)-3-[(1α,3α,4α)-3,4-difluorocyclopentyl]-N-[5-(4-methylpiperazine-1-ylsulfonyl)thiazol-2-yl]-2-(4-(methylsulfonyl)phenyl)acrylamide, (E)-3-[(1α,3α,4α)-3,4-difluorocyclopentyl]-2-(4-(methylsulfonyl)phenyl)-N-(1,2,4-thiadiazol-5-yl)acrylamide, (E)-3-[(1α,3α,4α)-3,4-difluorocyclopentyl]-2-(4-(methylsulfonyl)phenyl)-N-(3-methyl-1,2,4-thiadiazol-5-yl)acrylamide, (E)-3-[(1α,3α,4α)-3,4-difluorocyclopentyl]-N-(3-ethyl-1,2,4-thiadiazol-5-yl)-2-(4-(methylsulfonyl)phenyl)acrylamide, (E)-3-[(1α,3α,4α)-3,4-difluorocyclopentyl]-N-(3-methoxy-1,2,4-thiadiazol-5-yl)-2-(4-(methylsulfonyl)phenyl)acrylamide, (E)-3-[(1α,3α,4α)-3,4-difluorocyclopentyl]-2-(4-(methylsulfonyl)phenyl)-N-(pyridin-2-yl)acrylamide, (E)-3-[(1α,3α,4α)-3,4-difluorocyclopentyl]-N-(5-fluoropyridin-2-yl)-2-(4-(methylsulfonyl)phenyl)acrylamide, (E)-N-(5-chloropyridin-2-yl)-3-[(1α,3α,4α)-3,4-difluorocyclopentyl]-2-(4-(methylsulfonyl)phenyl)acrylamide, (E)-3-[(1α,3α,4α)-3,4-difluorocyclopentyl]-2-(4-(methylsulfonyl)phenyl)-N-[5-(methylthio)pyridin-2-yl]acrylamide, (E)-N-(5-cyclopropylpyridin-2-yl)-3-[(1α,3α,4α)-3,4-difluorocyclopentyl]-2-(4-(methylsulfonyl)phenyl)acrylamide, (E)-3-[(1α,3α,4α)-3,4-difluorocyclopentyl]-N-[5-(hydroxymethyl)pyridin-2-yl]-2-(4-(methylsulfonyl)phenyl)acrylamide, (E)-3-[(1α,3α,4α)-3,4-difluorocyclopentyl]-N-[5-(N,N-dimethylsulfamoyl)pyridin-2-yl]-2-(4-(methylsulfonyl)phenyl)acrylamide, (E)-3-[(1α,3α,4α)-3,4-difluorocyclopentyl]-2-(4-(methylsulfonyl)phenyl)-N-(pyrazin-2-yl)acrylamide, (E)-3-[(1α,3α,4α)-3,4-difluorocyclopentyl]-N-(5-methylpyrazin-2-yl)-2-(4-(methylsulfonyl)phenyl)acrylamide, (E)-3-[(1α,3α,4α)-3,4-difluorocyclopentyl]-N-(5-ethylpyrazin-2-yl)-2-(4-(methylsulfonyl)phenyl)acrylamide, (E)-3-[(1α,3α,4α)-3,4-difluorocyclopentyl]-N-(5-methoxypyrazin-2-yl)-2-(4-(methylsulfonyl)phenyl)acrylamide, (E)-3-[(1α,3α,4α)-3,4-difluorocyclopentyl]-N-[5-(2-methylethoxy)pyrazin-2-yl]-2-(4-(methylsulfonyl)phenyl)acrylamide, (E)-3-[(1α,3α,4α)-3,4-difluorocyclopentyl]-N-[5-(2-methoxyethoxy)pyrazin-2-yl]-2-(4-(methylsulfonyl)phenyl)acrylamide, (E)-3-[(1α,3α,4α)-3,4-difluorocyclopentyl]-N-[5-(3-methoxypropoxy)pyrazin-2-yl]-2-(4-(methylsulfonyl)phenyl)acrylamide, (E)-

3-[(1α,3α,4α)-3,4-difluorocyclopentyl]-N-[5-(2-ethoxyethoxy)pyrazin-2-yl]-2-(4-(methylsulfonyl)phenyl)acrylamide, (E)-3-[(1α,3α,4α)-3,4-difluorocyclopentyl]-2-(4-(methylsulfonyl)phenyl)-N-{5-[2-(methylthio)ethoxy]pyrazin-2-yl}acrylamide, (E)-2-(4-(methylsulfonyl)phenyl)-3-[(1α,3α,4α)-3,4-difluorocyclopentyl]-N-[5-(2-hydroxyethylthio)pyrazin-2-yl]acrylamide, (E)-3-[(1α,3α,4α)-3,4-difluorocyclopentyl]-2-(4-(methylsulfonyl)phenyl)-N-{5-[2-(tetrahydro-2H-pyran-2-yloxy)ethoxy]pyrazin-2-yl}acrylamide, (E)-3-[(1α,3α,4α)-3,4-difluorocyclopentyl]-N-[5-(2-(hydroxyethoxy)pyrazin-2-yl)-2-(4-(methylsulfonyl)phenyl)acrylamide, (E)-3-[(1α,3α,4α)-3,4-difluorocyclopentyl]-N-{5-[(4R)-2,2-dimethyl-1,3-dioxolan-4-yl]pyrazin-2-yl}-2-(4-(methylsulfonyl)phenyl)acrylamide, (E)-3-[(1α,3α,4α)-3,4-difluorocyclopentyl]-N-{5-[(4S)-2,2-dimethyl-1,3-dioxolan-4-yl]pyrazin-2-yl}-2-(4-(methylsulfonyl)phenyl)acrylamide, (E)-3-[(1α,3α,4α)-3,4-difluorocyclopentyl]-N-{5-[(2R)-1,2-dihydroxyethyl]pyrazin-2-yl}-2-(4-(methylsulfonyl)phenyl)acrylamide, (E)-3-[(1α,3α,4α)-3,4-difluorocyclopentyl]-N-{5-[(2S)-1,2-dihydroxyethyl]pyrazin-2-yl}-2-(4-(methylsulfonyl)phenyl)acrylamide, diethyl 5-{(E)-3-[(1α,3α,4α)-3,4-difluorocyclopentyl-2-(4-(methylsulfonyl)phenyl)]acrylamide}pyrazin-2-ylphosphonate, diethyl (5-{(E)-3-[(1α,3α,4α)-3,4-difluorocyclopentyl-2-(4-(methylsulfonyl)phenyl)]acrylamide}pyrazin-2-yl)methylphosphonate, (E)-3-[(1α,3α,4α)-3,4-difluorocyclopentyl]-N-[1-methyl-1H-pyrazol-3-yl]-2-(4-(methylsulfonyl)phenyl)acrylamide, (E)-3-[(1α,3α,4α)-3,4-difluorocyclopentyl]-N-[1-ethyl-1H-pyrazol-3-yl]-2-(4-(methylsulfonyl)phenyl)acrylamide, (E)-3-[(1α,3α,4α)-3,4-difluorocyclopentyl]-N-[1-(difluoromethyl)-1H-pyrazol-3-yl]-2-(4-(methylsulfonyl)phenyl)acrylamide, (E)-3-[(1α,3α,4α)-3,4-difluorocyclopentyl]-N-[1-(2-fluoroethyl)-1H-pyrazol-3-yl]-2-(4-(methylsulfonyl)phenyl)acrylamide, (E)-3-[(1α,3α,4α)-3,4-difluorocyclopentyl]-2-(4-(methylsulfonyl)phenyl)-N-[1-(2,2,2-trifluoroethyl)-1H-pyrazol-3-yl]acrylamide, (E)-3-[(1α,3α,4α)-3,4-difluorocyclopentyl]-N-[1-(2-hydroxyethyl)-1H-pyrazol-3-yl]-2-(4-(methylsulfonyl)phenyl)acrylamide, (E)-3-[(1α,3α,4α)-3,4-difluorocyclopentyl]-N-[1-(2-hydroxy-2-methylpropyl)-1H-pyrazol-3-yl]-2-(4-(methylsulfonyl)phenyl)acrylamide, (E)-3-[(1α,3α,4α)-3,4-difluorocyclopentyl]-N-(1-{[(4R)-2,2-dimethyl-1,3-dioxolan-4-yl]methyl}-1H-pyrazol-3-yl)-2-(4-(methylsulfonyl)phenyl)acrylamide, (E)-3-[(1α,3α,4α)-3,4-difluorocyclopentyl]-N-(1-{[(4S)-2,2-dimethyl-1,3-dioxolan-4-yl]methyl}-1H-pyrazol-3-yl)-2-(4-(methylsulfonyl)phenyl)acrylamide, (E)-3-[(1α,3α,4α)-3,4-difluorocyclopentyl]-N-{1-[(2R)-2,3-dihydroxypropyl]-1H-pyrazol-3-yl}-2-(4-(methylsulfonyl)phenyl)acrylamide, (E)-3-[(1α,3α,4α)-3,4-difluorocyclopentyl]-N-{1-[(2S)-2,3-dihydroxypropyl]-1H-pyrazol-3-yl}-2-(4-(methylsulfonyl)phenyl)acrylamide, (E)-3-[(1α,3α,4α)-3,4-difluorocyclopentyl]-N-(isoxazol-3-yl)-2-(4-(methylsulfonyl)phenyl)acrylamide, (E)-3-[(1α,3α,4α)-3,4-difluorocyclopentyl]-N-(6-methoxybenzo[d]thiazol-2-yl)-2-(4-(methylsulfonyl)phenyl)acrylamide, (E)-3-[(1α,3α,4α)-3,4-difluorocyclopentyl]-N-[6-(difluoromethoxy)benzo[d]thiazol-2-yl]-2-(4-(methylsulfonyl)phenyl)acrylamide, (E)-3-[(1α,3α,4α)-3,4-difluorocyclopentyl]-N-[5-(2-methoxyethoxy)thiazolo[5,4-b]pyridin-2-yl]-2-(4-(methylsulfonyl)phenyl)acrylamide, ethyl (E)-2-{2-[(R)-2-(4-(methylsulfonyl)phenyl)-3-[(1α,3α,4α)-3,4-difluorocyclopentyl]acrylamide]thiazolo[5,4-b]pyridin-2-yloxy}acetate, (E)-2-(4-(cyclopropylsulfonyl)phenyl)-3-[(1α,3α,4α)-3,4-difluorocyclopentyl]-N-(5-fluorothiazol-2-yl)acrylamide, (E)-N-(5-bromothiazol-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-(4-methylthiazol-2-yl)acrylamide, (E)-2-(4-(cyclopropylsulfonyl)phenyl)-3-[(1α,3α,4α)-3,4-difluorocyclopentyl]-N-(5-methylthiazol-2-yl)acrylamide, (+)-(E)-2-(4-(cyclopropylsulfonyl)phenyl)-3-[(1α,3α,4α)-3,4-difluorocyclopentyl]-N-[4-(2,2-dimethyl-1,3-dioxolan-4-yl)thiazol-2-yl]acrylamide, (−)-(E)-2-(4-(cyclopropylsulfonyl)phenyl)-3-[(1α,3α,4α)-3,4-difluorocyclopentyl]-N-[4-(2,2-dimethyl-1,3-dioxolan-4-yl)thiazol-2-yl]acrylamide, (E)-N-(4-tert-butylthiazol-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-[5-(4-methylpiperazin-1-ylsulfonyl)thiazol-2-yl]acrylamide, methyl 3-(2-[(E)-2-(4-(cyclopropylsulfonyl)phenyl)-3-[(1α,3α,4α)-3,4-difluorocyclopentyl]acrylamide]thiazol-4-yl)propionate, (E)-2-(4-(cyclopropylsulfonyl)phenyl)-3-[(1α,3α,4α)-3,4-difluorocyclopentyl]-N-(1,2,4-thiadiazol-5-yl)acrylamide, (E)-2-(4-(cyclopropylsulfonyl)phenyl)-3-[(1α,3α,4α)-3,4-difluorocyclopentyl]-N-(3-methyl-1,2,4-thiadiazol-5-yl)acrylamide, (E)-2-(4-(cyclopropylsulfonyl)phenyl)-3-[(1α,3α,4α)-3,4-difluorocyclopentyl]-N-(3-ethyl-1,2,4-thiadiazol-5-yl)acrylamide, (E)-2-(4-(cyclopropylsulfonyl)phenyl)-3-[(1α,3α,4α)-3,4-difluorocyclopentyl]-N-(3-phenyl-1,2,4-thiadiazol-5-yl)acrylamide, (E)-2-(4-(cyclopropylsulfonyl)phenyl)-3-[(1α,3α,4α)-3,4-difluorocyclopentyl]-N-(pyridin-2-yl)acrylamide, (E)-2-(4-(cyclopropylsulfonyl)phenyl)-3-[(1α,3α,4α)-3,4-difluorocyclopentyl]-N-[5-(methylthio)pyridin-2-yl]acrylamide, (E)-N-(5-cyclopropylpyridin-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-[5-(hydroxymethyl)pyridin-2-yl]acrylamide, (E)-2-(4-(cyclopropylsulfonyl)phenyl)-3-[(1α,3α,4α)-3,4-difluorocyclopentyl]-N-[5-(N,N-dimethylsulfamoyl)pyridin-2-yl]acrylamide, (E)-2-(4-(cyclopropylsulfonyl)phenyl)-3-[(1α,3α,4α)-3,4-difluorocyclopentyl]-N-(pyrazin-2-yl)acrylamide, (E)-2-(4-(cyclopropylsulfonyl)phenyl)-3-[(1α,3α,4α)-3,4-difluorocyclopentyl]-N-(5-methylpyrazin-2-yl)acrylamide, (E)-2-(4-(cyclopropylsulfonyl)phenyl)-3-[(1α,3α,4α)-3,4-difluorocyclopentyl]-N-(5-ethylpyrazin-2-yl)acrylamide, (E)-2-(4-(cyclopropylsulfonyl)phenyl)-3-[(1α,3α,4α)-3,4-difluorocyclopentyl]-N-(5-methoxypyrazin-2-yl)acrylamide, (E)-2-(4-(cyclopropylsulfonyl)phenyl)-3-[(1α,3α,4α)-3,4-difluorocyclopentyl]-N-[5-(methylthio)pyrazin-2-yl]acrylamide, (E)-2-(4-(cyclopropylsulfonyl)phenyl)-3-[(1α,3α,4α)-3,4-difluorocyclopentyl]-N-[5-(2-methylethoxy)pyrazin-2-yl]acrylamide, (E)-2-(4-(cyclopropylsulfonyl)phenyl)-3-[(1α,3α,4α)-3,4-difluorocyclopentyl]-N-[5-(2-methoxyethoxy)pyrazin-2-yl]acrylamide, (E)-2-(4-(cyclopropylsulfonyl)phenyl)-3-[(1α,3α,4α)-3,4-difluorocyclopentyl]-N-[5-(3-methoxypropoxy)pyrazin-2-yl]acrylamide, (E)-2-(4-(cyclopropylsulfonyl)phenyl)-3-[(1α,3α,4α)-3,4-difluorocyclopentyl]-N-[5-(2-ethoxyethoxy)pyrazin-2-yl]acrylamide, (E)-2-(4-(cyclopropylsulfonyl)phenyl)-3-[(1α,3α,4α)-3,4-difluorocyclopentyl]-N-{5-[2-(methylthio)ethoxy]pyrazin-2-yl}acrylamide, (E)-2-(4-(cyclopropylsulfonyl)phenyl)-3-[(1α,3α,4α)-3,4-difluorocyclopentyl]-N-{5-[2-(tetrahydro-2H-pyran-2-yloxy)ethoxy]pyrazin-2-yl}acrylamide, (E)-2-(4-(cyclopropylsulfonyl)phenyl)-3-[(1α,3α,4α)-3,4-difluorocyclopentyl]-N-{5-(2-(hydroxyethoxy)pyrazin-2- yl}acrylamide, (E)-2-(4-(cyclopropylsulfonyl)phenyl)-3-[(1α,3α,4α)-3,4-difluorocyclopentyl]-N-{5-[(4R)-2,2-dimethyl-1,3-dioxolan-4-yl]pyrazin-2-yl}acrylamide, (E)-2-(4-(cyclopropylsulfonyl)phenyl)-3-[(1α,3α,4α)-3,4-difluorocyclopentyl]-N-{5-[(4S)-2,2-dimethyl-1,3-dioxolan-4-yl]pyrazin-2-yl}acrylamide, (E)-2-(4-(cyclopropylsulfonyl)phenyl)-3-[(1α,3α,4α)-3,4-difluorocyclopentyl]-N-{5-[(2R)-1,2-dihydroxyethyl]pyrazin-2-yl}acrylamide, (E)-2-(4-(cyclopropylsulfonyl)phenyl)-3-[(1α,3α,4α)-3,4-difluorocyclopentyl]-N-{5-[(2S)-1,2-dihydroxyethyl]pyrazin-2-yl}acrylamide, diethyl 5-{(E)-2-(4-(cyclopropylsulfonyl)phenyl)-3-[(1α,3α,4α)-3,4-difluorocyclopentyl]acrylamide}pyrazin-2-yl phosphonate, diethyl (5-{(E)-2-(4-(cyclopropylsulfonyl)phenyl)-3-[(1α,3α,4α)-3,4-difluorocyclopentyl]acrylamide}pyrazin-2-yl methylphosphonate, (E)-2-(4-(cyclopropylsulfonyl)phenyl)-3-[(1α,3α,4α)-3,4-difluorocyclopentyl]-N-(1-methyl-1H-pyrazol-3-yl)acryl amide, (E)-2-(4-(cyclopropylsulfonyl)phenyl)-3-[(1α,3α,4α)-3,4-difluorocyclopentyl]-N-(1-ethyl-1H-pyrazol-3-yl)acrylamide, (E)-2-(4-(cyclopropylsulfonyl)phenyl)-3-[(1α,3α,4α)-3,4-difluorocyclopentyl]-N-(1-(2-fluoroethyl)-1H-pyrazol-3-yl)acrylamide, (E)-2-(4-(cyclopropylsulfonyl)phenyl)-3-[(1α,3α,4α)-3,4-difluorocyclopentyl]-N-[1-(2-hydroxyethyl)-1H-pyrazol-3-yl]acrylamide, (E)-2-(4-(cyclopropylsulfonyl)phenyl)-3-[(1α,3α,4α)-3,4-difluorocyclopentyl]-N-[1-(2-hydroxy-2-methylpropyl)-1H-pyrazol-3-yl]acrylamide, (E)-2-(4-(cyclopropylsulfonyl)phenyl)-3-[(1α,3α,4α)-3,4-difluorocyclopentyl]-N-(1-{[(4R)-2,2-dimethyl-1,3-dioxolan-4-yl]methyl}-1H-pyrazol-3-yl}acrylamide, (E)-2-(4-(cyclopropylsulfonyl)phenyl)-3-[(1α,3α,4α)-3,4-difluorocyclopentyl]-N-(1-{[(4S)-2,2-dimethyl-1,3-dioxolan-4-yl]methyl}-1H-pyrazol-3-yl}acrylamide, (E)-2-(4-(cyclopropylsulfonyl)phenyl)-3-[(1α,3α,4α)-3,4-difluorocyclopentyl]-N-{1-[(2R)-2,3-dihydroxypropyl]-1H-pyrazol-3-yl}acrylamide, (E)-2-(4-(cyclopropylsulfonyl)phenyl)-3-[(1α,3α,4α)-3,4-difluorocyclopentyl]-N-(1-{[(4S)-2,2-dimethyl-1,3-dioxolan-4-yl]methyl}-1H-pyrazol-3-yl}acrylamide, (E)-2-(4-(cyclopropylsulfonyl)phenyl)-3-[(1α,3α,4α)-3,4-difluorocyclopentyl]-N-(isoxazol-3-yl)acrylamide, (E)-N-(benzo[d]thiazol-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-(6-methoxybenzo[d]thiazol-2-yl)acrylamide, (E)-2-(4-(cyclopropylsulfonyl)phenyl)-3-[(1α,3α,4α)-3,4-difluorocyclopentyl]-N-[6-difluoromethoxy]benzo[d]thiazol-2-yl]acrylamide, (E)-2-(4-(cyclopropylsulfonyl)phenyl)-3-[(1α,3α,4α)-3,4-difluorocyclopentyl]-N-(6-fluorobenzo[d]thiazol-2-yl)acrylamide, 2-methylethyl 2-{(E)-2-(4-(cyclopropylsulfonyl)phenyl)-3-[(1α,3α,4α)-3,4-difluorocyclopentyl]acrylamide}benzo[d]thiazol-6-carboxylic acid, (E)-2-(4-(cyclopropylsulfonyl)phenyl)-3-[(1α,3α,4α)-3,4-difluorocyclopentyl]-N-(thiazolo[5,4-b]pyridin-2-yl)acrylamide, (E)-N-(5-butoxythiazolo[5,4-b]pyridin-2-yl)-2-(4-(cyclopropylsulfonyl)phenyl)-3-[(1α,3α,4α)-3,4-difluorocyclopentyl]acrylamide, (E)-2-(4-(cyclopropylsulfonyl)phenyl)-3-[(1α,3α,4α)-3,4-difluorocyclopentyl]-N-[5-(2-methoxyethoxy)thiazolo[5,4-b]pyridin-2-yl)acrylamide, ethyl 2-{2-[(R)-2-(4-(cyclopropylsulfonyl)phenyl)-3-[(1α,3α,4α)-3,4-difluorocyclopentyl]acrylamide]thiazolo[5,4-b]pyridin-5-yloxy}acetate, (E)-3-[(1α,3α,4α)-3,4-difluorocyclopentyl]-2-[4-(ethylsulfonyl)phenyl]-N-(thiazol-2-yl)acrylamide, (E)-3-[(1α,3α,4α)-3,4-difluorocyclopentyl]-2-[4-(ethylsulfonyl)phenyl]-N-(5-methylpyrazin-2-yl)acrylamide, (E)-3-[(1α,3α,4α)-3,4-difluorocyclopentyl]-2-[4-(ethylsulfonyl)phenyl]-N-(1-methyl-1H-pyrazol-3-yl)acrylamide, (E)-3-[(1α,3α,4α)-3,4-difluorocyclopentyl]-2-[4-(2-methoxyethylsulfonyl)phenyl]-N-(thiazol-2-yl)acrylamide, (E)-3-[(1α,3α,4α)-3,4-difluorocyclopentyl]-2-[4-(2-methoxyethylsulfonyl)phenyl]-N-(5-methylpyrazin-2-yl)acrylamide, and (E)-3-[(1α,3α,4α)-3,4-difluorocyclopentyl]-2-[4-(2-methoxyethylsulfonyl)phenyl]-N-(1-methyl-1H-pyrazol-3-yl)acrylamide.

The compound represented by the general formula (1) of the present invention can be produced by, for example, the following production process with the compound represented by the general formula (2) as an intermediate:

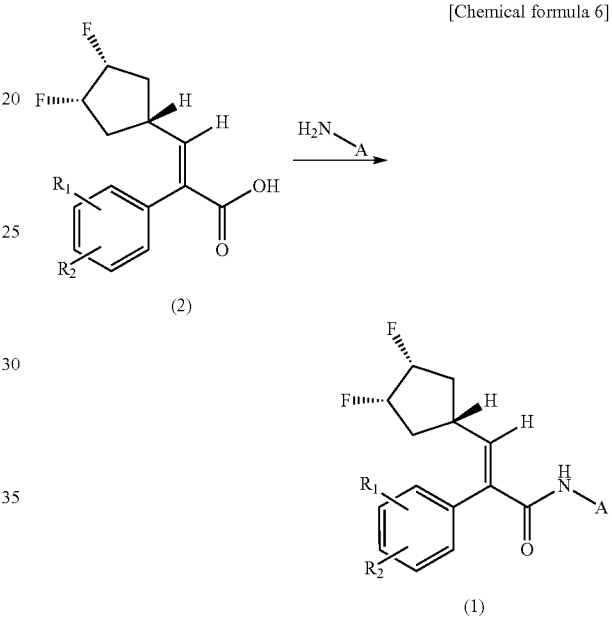

[Chemical formula 6]

(wherein $R^1$, $R^2$, and A are as defined above).

In this process, the compound represented by the general formula (2) is reacted with a heteroarylamine in the presence of a suitable reagent to produce the compound represented by the general formula (1).

This reaction may be performed using an appropriate method such as a method using a general condensation agent, the active ester method, the mixed anhydride method, the acid halide method, or the carbodiimide method. Examples of the reagent used in the above reaction include thionyl chloride, oxalyl chloride, N,N'-dicyclohexylcarbodiimide, N,N'-diisopropylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazo-1-yl-oxy-tris(dimethylamino)phosphonium hexafluorophosphate, and N-bromosuccinimide/triphenylphosphine. In this process, a base and a condensation aid may be used together with the above reagent. Any base can be used in this process, so long as it is not involved in the reaction. The reaction can be performed in the presence of such a base. Examples of the base include: alkali metal alkoxides such as sodium methoxide and sodium ethoxide; alkali metal hydrides such as sodium hydride and potassium hydride; alkali metal organic bases such as n-butyllithium, lithium bis(trimethylsilyl)amide, sodium bis(trimethylsilyl)amide, and potassium bis(trimethylsilyl)amide; tertiary organic bases such as triethylamine, diisopropylethylamine, pyridine, N-methylmorpholine, imidazole, N-methylpyrrolidine, N-methylpiperidine, 1,5-diazabicyclo[4.3.0]non-5-ene, and 1,8-diazabicyclo[5.4.0]undec-7-ene; and inorganic bases such as potassium carbonate and sodium hydrogen carbonate. Examples of the condensation aid include N-hydroxybenzotriazole hydrate, N-hydroxysuccinimide, N-hydroxy-5-norbornene-2,3-dicarboxyimide, 3-hydroxy-3,4-dihydro-4-oxo-1,2,3-benzotriazole, and pentafluorophenol. Any solvent can be used as the reaction solvent, so long as it is not involved in the reaction. Preferred examples of such a solvent include: hydrocarbon solvents such as pentane, hexane, cyclohexane, benzene, toluene, and xylene; halogenated hydrocarbon solvents such as dichloromethane, 1,2-dichloroethane, chloroform, and carbon tetrachloride; ether solvents such as diethyl ether, tetrahydrofuran, and 1,4-dioxane; and aprotic polar solvents such as acetonitrile, propionitrile, nitromethane, nitroethane, N,N-dimethylformamide, N-methylpiperidone, sulfolane, and dimethyl sulfoxide. The reaction typically proceeds smoothly at −78° C. to 200° C.

Furthermore, the compounds represented by the formulae (1) and (2) of the present invention can also be produced based on the following production steps.

[Formula 7]

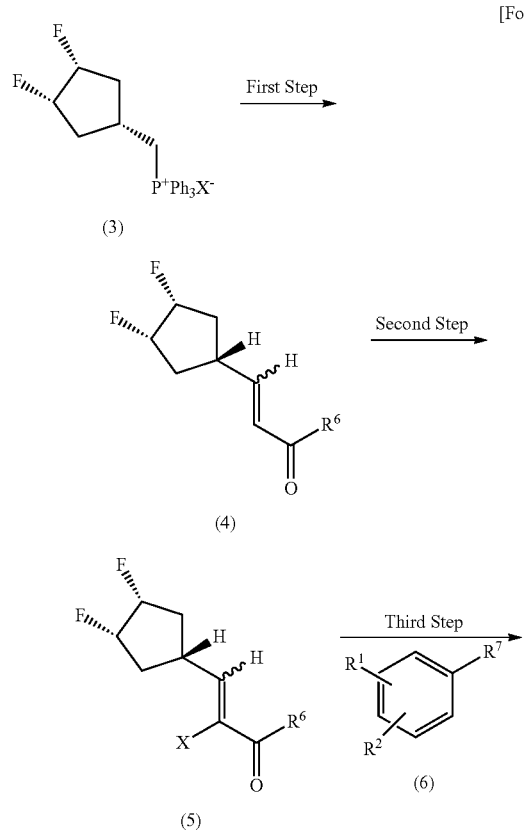

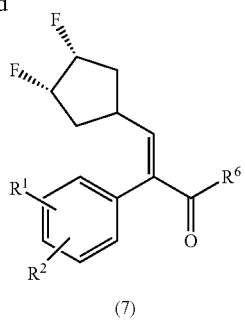

(wherein $R^6$ represents an optionally substituted alkoxy group or an optionally substituted amino group, $R^7$ represents a boric acid derivative, a halogen atom, or a trifluoromethanesulfonyloxy group, and X represents a halogen atom; $R^1$ and $R^2$ are as defined above)

(First Step)

This step is for producing an acrylic acid derivative (4) by reacting the compound represented by the formula (3) with a glyoxylaldehyde in the presence of a base. Examples of the base used in this reaction include alkali metal amides such as lithium diisopropylamide, lithium bis(trimethylsilyl)amide, sodium bis(trimethylsilyl)amide, and potassium bis(trimethylsilyl)amide, metal hydrides such as lithium hydride, sodium hydride, and potassium hydride, potassium carbonate, tert-butoxy potassium, and n-butyllithium. In this reaction, lithium bis(trimethylsilyl)amide is preferred.

Any solvent can be used as the solvent used in this reaction, as long as it is not involved in the reaction. Examples of such a solvent include hydrocarbon solvents such as pentane, hexane, cyclohexane, benzene, toluene, and xylene, halogenated hydrocarbon solvents such as dichloromethane, 1,2-dichloroethane, chloroform, and carbon tetrachloride, and ether solvents such as diethyl ether, tetrahydrofuran, and 1,4-dioxane. The reaction proceeds smoothly at −80° C. to 80° C.

(Second Step)

This step is for producing a 3-(3,4-difluorocyclopentyl)-2-halogeno acrylic acid derivative by halogenating the 3-(3,4-difluorocyclopentyl)acrylic acid derivative represented by the formula (4) obtained in the above first step with molecular halogen, and then reacting with the base.

Examples of the base used in this reaction include carbonic acid salts such as sodium carbonate, potassium carbonate, calcium carbonate, cesium carbonate, and barium carbonate, or organic bases such as triethylamine, diisopropylethylamine, N,N,N,N-tetramethylethylenediamine, diazabicyclo[5.4.0]-7-undecene, diazabicyclo[4.3.0]-5-nonene, phosphazene bases, and pentaisopropylguanidine. However, in this reaction, triethylamine is preferred.

Any solvent can be used as the solvent used in this reaction, as long as it is not involved in the reaction. Examples of such a solvent include hydrocarbon solvents such as pentane, hexane, cyclohexane, benzene, toluene, and xylene, halogenated hydrocarbon solvents such as dichloromethane, 1,2-dichloroethane, chloroform, and carbon tetrachloride, and ether solvents such as diethyl ether, tetrahydrofuran, and 1,4-dioxane. The reaction proceeds smoothly at −80° C. to 80° C.

(Third Step)

This step is for producing a 3-(3,4-difluorocyclopentyl)-2-(substituted phenyl)acrylic acid derivative by reacting a compound represented by the formula (6) with the 3-(3,4-difluorocyclopentyl)-2-halogeno acrylic acid derivative represented by the formula (5) obtained in the above second step in the presence of a catalyst and a base.

In the formula, if $R^7$ is a halogen atom or a trifluoromethanesulfonyloxy group, for example, boric acid, pinacolato diboron or the like can be reacted to convert the compound into a boric acid derivative for use in the presence of a palladium complex, such as 1,1-bis(diphenylphosphino) ferrocene-palladium(II) dichloride, and an acetic acid salt, such as potassium acetate. The thus-obtained boric acid derivative is used after isolated and purified, or is prepared in the reaction system. As the catalyst used in this reaction, tetrakis(triphenylphosphine)palladium, palladium acetate, or a palladium complex such as 1,1-bis(diphenylphosphino)ferrocene-palladium(II)dichloride, can be used.

As the base used in this reaction, a carbonic acid salt such as sodium carbonate, potassium carbonate, calcium carbonate, cesium carbonate, and barium carbonate, or an acetic acid salt such as potassium acetate and sodium acetate, can be used.

Any solvent can be used as the reaction solvent, so long as it is not involved in the reaction. Examples of such a solvent include: hydrocarbon solvents such as pentane, hexane, cyclohexane, benzene, toluene, and xylene; halogenated hydrocarbon solvents such as dichloromethane, 1,2-dichloroethane, chloroform, and carbon tetrachloride; ether solvents such as diethyl ether, tetrahydrofuran, and 1,4-dioxane; aprotic polar solvents such as acetonitrile, propionitrile, nitromethane, nitroethane, N,N-dimethylformamide, and dimethyl sulfoxide; alcohol solvents such as methanol, ethanol, 1-propanol, 2-propanol, 1-butanol, 2-butanol, 2-methyl-1-propanol, 2-methyl-2-propanol, and benzyl alcohol; and water. One kind of solvent, or two or three kinds of solvents in combination, may be used. The reaction proceeds smoothly at −80° C. to 150° C.

One embodiment of the present invention relates to a pharmaceutical containing, as an active ingredient, the compound represented by the formula (1) or a pharmaceutically acceptable salt thereof. The pharmaceuticals of the present invention have a GK activating effect or a hypoglycemic effect and therefore is useful for the treatment or prevention of type I diabetes, type II diabetes, hyperlipemia (hyper LDL cholesterolemia, hypertriglyceridemia, and hypo HDL cholesterolemia), obesity, insulin resistance, impaired glucose tolerance, metabolic syndrome, and the like.

The pharmaceutical of the present invention may be administered orally or parenterally, for example, intrarectally, subcutaneously, intravenously, intramuscularly, or percutaneously.

The compound of the present invention or a pharmaceutically acceptable salt thereof may be used as pharmaceuticals in any form (for example, a solid composition, a liquid composition, or other type of composition). An optimal form is selected in accordance with need. The pharmaceutical of the present invention can be produced by adding a pharmaceutically acceptable carrier to the compound of the present invention. More specifically, commonly used additives such as excipient, extender, binder, disintegrator, coating, sugar-coating agent, pH modifier, and solubilizing agent and an aqueous or non-aqueous solvent are added to the compound of the present invention, and the mixture can be formed into various forms such as tablets, pills, capsules, granules, powders, powdered drugs, liquid formulations, emulsions, suspensions, and injections by any commonly used formulation method.

The dose of the compound of the present invention or a pharmaceutically acceptable salt thereof depends on the type of disease, the condition, weight, age, and sex of a patient, the route of administration, and the like. The oral dose for an adult is preferably about 0.01 to about 1000 mg/kg body weight/day, and more preferably about 0.5 to about 200 mg/kg body weight/day. This amount may be administered in a single dose or in divided doses throughout the day.

If necessary, the compound of the present invention or a pharmaceutically acceptable salt thereof may be used together with one or more compounds other than GK activators. For example, the compound of the present invention or a pharmaceutically acceptable salt thereof may be used in combination with one or more of anti-obesity agents and antidiabetic (or hypoglycemic) agents including sulfonylureas, biguanides, glucagon antagonists, α-glucosidase inhibitors, insulin secretion promoters, insulin sensitizers, and the like.

Examples of the sulfonylureas include glyburide, glimepiride, glipiride, glipizide, chlorpropamide, gliclazide, glisoxepide, acetohexamide, glibornuride, tolbutamide, tolazamide, carbutamide, gliquidone, glyhexamide, phenbutamide, and tolcyclamide. Examples of the biguanides include metformin, phenformin, and buformin. Examples of the glucagon antagonists include peptide and non-peptide glucagon antagonists. Examples of the α-glucosidase inhibitors include acarbose, voglibose, and miglitol. Examples of the insulin sensitizers include troglitazone, rosiglitazone, pioglitazone, and ciglitazone. Examples of the anti-obesity agents include sibutramine and orlistat. The compound of the present invention or a pharmaceutically acceptable salt thereof may be administered simultaneously, sequentially or separately with other antidiabetic, hypoglycemic, and anti-obesity agents.

EXAMPLE 1

3-[(1α,3α,4α)-3,4-Difluorocyclopentyl]-2-[4-(methylthio)phenyl]acrylic acid ethyl ester

[Chemical formula 8]

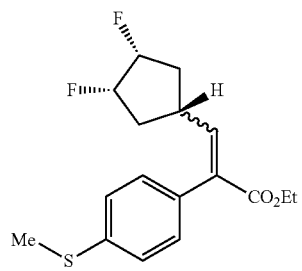

(1α,3α,4α)-(3,4-Difluorocyclopentyl)methyltriphenylphosphonium iodide (2.67 g) was suspended in tetrahydrofuran (10 mL). Lithium bis(trimethylsilyl)amide (a 1 mol/L tetrahydrofuran solution, 5.30 mL) was added to the suspension at −40° C. in an argon atmosphere, and the mixture was stirred at −40° C. for 2 hours. Subsequently, a solution of 2-[(4-methylthio)phenyl]oxoacetic acid ethyl ester (1.12 g) in tetrahydrofuran (3.70 mL) was added dropwise to the reaction mixture cooled to −40° C., and the resultant mixture was stirred at −40° C. for 2 hours and further stirred at room temperature for 18 hours. Water (10 mL) was added to the reaction mixture, and the pH of the mixture was adjusted to 2 with 3 mol/L hydrochloric acid. Tetrahydrofuran was evaporated under reduced pressure, and the residue was extracted with ethyl acetate (20 mL×2). The ethyl acetate extracts were combined, washed with saturated brine (10 mL), dried over anhydrous sodium sulfate, filtrated, and concentrated under reduced pressure. The residue was purified by silica gel column chromatography (eluent; hexane:ethyl acetate=4:1) to give 3-[(1α,3α,4α)-3,4-difluorocyclopentyl]-2-[4-(methylthio)phenyl]acrylic acid ethyl ester (1.54 g).

$^1$H NMR (400 MHz, CDCl$_3$) δ 1.27 (t, J=7.3 Hz, 3H), 1.30 (t, J=7.3 Hz, 3H), 1.84-2.19 (m, 6H), 2.28-2.42 (m, 2H), 2.49 (s, 3H), 2.50 (s, 3H), 2.55-2.69 (m, 1H), 3.17-3.31 (m, 1H), 4.21 (q, J=7.3 Hz, 2H), 4.27 (q, J=7.3 Hz, 2H), 4.68-5.04 (m, 4H), 6.13 (d, J=9.8 Hz, 1H), 7.00 (d, J=10.4 Hz, 1H), 7.03-7.08 (m, 2H), 7.22-7.25 (m, 6H).

MS (ESI$^+$) m/z: 327 (MH$^+$).

EXAMPLE 2

3-[(1α,3α,4α)-3,4-Difluorocyclopentyl]-2-[4-(methylsulfonyl)phenyl]acrylic acid ethyl ester

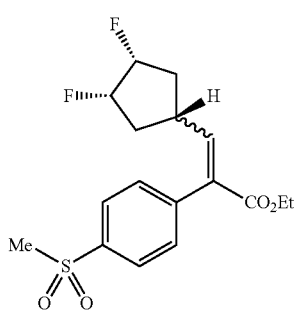

[Chemical formula 9]

3-[(1α,3α,4α)-3,4-Difluorocyclopentyl]-2-[4-(methylthio)phenyl]acrylic acid ethyl ester (3.00 g) was dissolved in dichloromethane (31 mL). m-Chloroperoxybenzoic acid (5.37 g) was added to the prepared solution cooled in an ice bath, and the mixture was stirred for 0.5 hours while cooled in the ice bath and further stirred at room temperature for 1.5 hours. Insoluble materials in the reaction mixture were removed by filtration, and the filtrate was diluted with dichloromethane (42 mL). The obtained dichloromethane solution was washed with a 10% aqueous sodium sulfite solution (20 mL×2), a saturated aqueous sodium hydrogen carbonate solution (20 mL×2), and saturated brine (20 mL), dried over anhydrous sodium sulfate, filtrated, and concentrated under reduced pressure to give 3-[(1α,3α,4α)-3,4-difluorocyclopentyl]-2-[4-(methylsulfonyl)phenyl]acrylic acid ethyl ester (3.41 g).

$^1$H NMR (400 MHz, CDCl$_3$) δ 1.30 (t, J=7.3 Hz, 3H), 1.31 (t, J=7.3 Hz, 3H), 1.86-2.20 (m, 6H), 2.30-2.56 (m, 3H), 3.06 (s, 3H), 3.10 (s, 3H), 3.35-3.48 (m, 1H), 4.24 (q, J=7.3 Hz, 2H), 4.29 (q, J=7.3 Hz, 2H), 4.69-5.10 (m, 4H), 6.29 (d, J=9.8 Hz, 1H), 7.09 (d, J=10.4 Hz, 1H), 7.33-7.38 (m, 2H), 7.48-7.53 (m, 2H), 7.89-7.93 (m, 2H), 7.93-7.97 (m, 2H).

MS (EI) m/z: 358 (M$^+$).

EXAMPLE 3

(E)-3-[(1α,3α,4α)-3,4-difluorocyclopentyl]-2-[4-(methylsulfonyl)phenyl]acrylic acid methyl ester

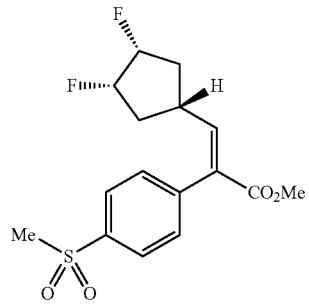

[Chemical formula 10]

3-[(1α,3α,4α)-3,4-Difluorocyclopentyl]-2-[4-(methylsulfonyl)phenyl]acrylic acid ethyl ester (5.00 g) was suspended in methanol (26 mL). A sodium methoxide solution prepared from 460 mg of sodium and 20 mL of methanol was added dropwise to the obtained suspension at room temperature, and the resultant mixture was stirred at room temperature for 3 hours. Methanol was evaporated under reduced pressure, and the resultant residue was collected by filtration and washed with methanol (50 mL) to give (E)-3-[(1α,3α,4α)-3,4-difluorocyclopentyl]-2-[4-(methylsulfonyl)phenyl]acrylic acid methyl ester (3.98 g).

$^1$H NMR (400 MHz, CDCl$_3$) δ 1.87-2.20 (m, 4H), 2.43-2.58 (m, 1H), 3.10 (s, 3H), 3.78 (s, 3H), 4.69-4.95 (m, 2H), 7.12 (d, J=11.0 Hz, 1H), 7.34 (d, J=7.9 Hz, 2H), 7.96 (d, J=7.9 Hz, 2H).

MS (EI) m/z: 344 (M$^+$).

EXAMPLE 4

(E)-3-[(1α,3α,4α)-3,4-difluorocyclopentyl]-2-[4-(methylsulfonyl)phenyl]acrylic acid

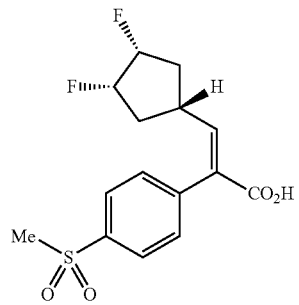

[Chemical formula 11]

A mixed solution of concentrated sulfuric acid (6.89 mL), acetic acid (37.1 mL), and water (22.5 mL) was added to (E)-3-[(1α,3α,4α)-3,4-difluorocyclopentyl]-2-[4-(methylsulfonyl)phenyl]acrylic acid methyl ester (3.95 g), and the mixture was stirred under heating at 103° C. (internal temperature) for 3 hours. After allowed to cool, the reaction mixture was evaporated under reduced pressure. Water (37 mL) was added to the residue, and the precipitate was collected by filtration and washed with water (100 mL). The collected precipitate was dissolved in a saturated aqueous sodium hydrogen carbonate solution and extracted with dichloromethane (15 mL×2). Concentrated hydrochloric acid was added to the aqueous layer, while cooled in an ice bath, to make it acidic. The resultant precipitate was collected by filtration and washed with water (100 mL) to give (E)-3-[(1α,3α,4α)-3,4-difluorocyclopentyl]-2-[4-(methylsulfonyl)phenyl]acrylic acid (3.26 g).

$^1$H NMR (400 MHz, CDCl$_3$) δ 1.88-2.21 (m, 4H), 2.47-2.62 (m, 1H), 3.09 (s, 3H), 4.73-4.97 (m, 2H), 7.24 (d, J=10.4 Hz, 1H), 7.34-7.39 (m, 2H), 7.94-7.99 (m, 2H).

MS (EI) m/z: 330 (M$^+$).

EXAMPLE 5

(E)-3-[(1α,3α,4α)-3,4-difluorocyclopentyl]-2-[4-(methylsulfonyl)phenyl]-N-(thiazol-2-yl)acrylamide (compound 1A of the present invention)

[Chemical formula 12]

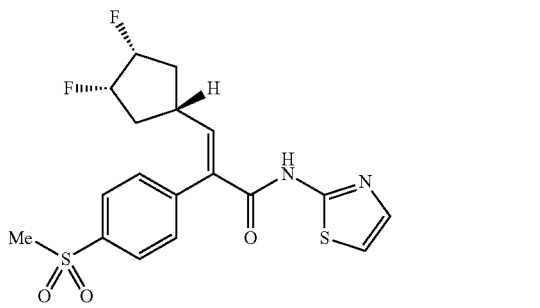

Thionyl chloride (3.43 mL) was added to (E)-3-[(1α,3α,4α)-3,4-difluorocyclopentyl]-2-[4-(methylsulfonyl)phenyl]acrylic acid (343 mg), and the mixture was heated to reflux for 45 minutes. After the mixture was cooled to room temperature, thionyl chloride was removed by evaporation. Toluene (3 mL×3) was added to the mixture, and the resultant mixture was evaporated under reduced pressure. A solution of 2-aminothiazole (104 mg) in pyridine (1.37 mL) was added to the resultant residue in a salted ice bath, and the mixture was stirred at room temperature for 1 hour. The reaction mixture was diluted with ethyl acetate (30 mL) and washed sequentially with 1 mol/L hydrochloric acid (30 mL×2), a saturated aqueous sodium hydrogen carbonate solution (30 mL×2) and saturated brine (30 mL), dried over anhydrous sodium sulfate, and filtrated, and the solvent was evaporated under reduced pressure. The obtained residue was purified by silica gel column chromatography (eluent; chloroform:methanol=50:1), and the obtained compound was washed with diethyl ether to give (E)-3-[(1α,3α,4α)-3,4-difluorocyclopentyl]-2-[4-(methylsulfonyl)phenyl]-N-(thiazol-2-yl)acrylamide (154 mg).

MS (ESI$^+$) m/z: 413 (MH$^+$).

HRMS (ESI$^+$) for C$_{18}$H$_{19}$F$_2$N$_2$O$_3$S$_2$ (MH$^+$): calcd., 413.08051; found, 413.08048.

$^1$H NMR (400 MHz, CDCl$_3$) δ 1.82-2.01 (m, 2H), 2.07-2.25 (m, 2H), 2.48-2.60 (m, 1H), 3.25 (s, 3H), 4.84-5.08 (m, 2H), 7.83 (d, J=10.4 Hz, 1H), 7.21 (brs, 1H), 7.47 (d, J=8.6 Hz, 2H), 7.51 (d, J=3.1 Hz, 1H), 7.94 (d, J=8.6 Hz, 2H), 12.4 (brs, 1H).

EXAMPLE 6

Compounds 2A to 62A of the present invention were produced according to the same procedure as in Example 5.

In the following Tables, the optical rotations of the compounds 7A, 8A, 40A, 41A, 53A, and 54A of the present invention were measured using methanol as a solvent, and the optical rotations of the compounds 51A and 52A of the present invention were measured using dichloromethane. The optical rotations of the rest of the compounds of the present invention were measured using chloroform.

[Chemical formula 13]

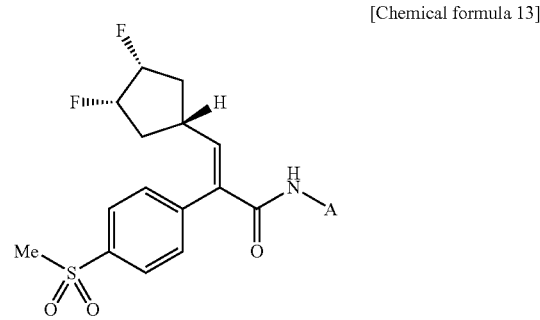

TABLE 1

| Compound No. | Structure (A) | 1H NMR (400 MHz) | MS (m/z) | Optical rotation |
|---|---|---|---|---|
| 2A | (thiazole with F) | (CDCl3) δ 1.93-2.15 (m, 4H), 2.38-2.48 (m, 1H), 3.17 (s, 3H), 4.75-4.80 (m, 1H), 4.88-4.93 (m, 1H), 6.99 (d, J = 2.5 Hz, 1H), 7.25 (d, J = 9.2 Hz, 1H), 7.45 (d, J = 8.6 Hz, 2H), 8.08 (d, J = 8.6 Hz, 2H), 8.13 (s, 1H). | (ESI+) 431.1 (MH+) | |
| 3A | (thiazole with Cl) | (DMSO-d6) δ 1.80-2.00 (m, 2H), 2.04-2.25 (m, 2H), 2.47-2.70 (m, 1H), 3.25 (s, 3H), 4.78-5.12 (m, 2H), 6.88 (d, J = 10.4 Hz, 1H), 7.47 (d, J = 8.6 Hz, 2H), 7.56 (s, 1H), 7.94 (d, J = 8.6 Hz, 2H), 12.7 (s, 1H). | (ESI+) 447.1 (MH+) | |
| 4A | (thiazole with Me) | (CDCl3) δ 1.71-2.18 (m, 4H), 2.30 (s, 3H), 2.35-2.48 (m, 1H), 3.18 (s, 3H), 4.71-4.95 (m, 2H), 6.57 (d, J = 1.2 Hz, 1H), 7.27 (d, J = 10.4 Hz, 1H), 7.43-7.48 (m, 2H), 8.05-8.10 (m, 2H), 8.36 (brs, 1H). | (ESI+) 427.1 (MH+) | |

TABLE 1-continued

| Compound No. | Structure (A) | 1H NMR (400 MHz) | MS (m/z) | Optical rotation |
|---|---|---|---|---|
| 5A | (2-methylthiazole with Me at 5-position) | (CDCl3) δ 1.92-2.19 (m, 4H), 2.35-2.48 (m, 1H), 2.41 (d, J = 1.2 Hz, 3H), 3.17 (s, 3H), 4.72-4.95 (m, 2H), 7.04 (d, J = 1.2 Hz, 1H), 7.25 (d, J = 11.0 Hz, 1H), 7.44-7.47 (m, 2H), 8.04-8.10 (m, 2H), 8.30 (brs, 1H). | (ESI+) 427.1 (MH+) | |
| 6A | (2-methylthiazole with dioxolane-dimethyl substituent) | (CDCl3) δ 1.43 (s, 3H), 1.47 (s, 3H), 1.96-2.20 (m, 4H), 2.37-2.49 (m, 1H), 3.19 (s, 3H), 3.93 (dd, J = 7.9, 6.7 Hz, 1H), 4.27 (dd, J = 7.9, 6.7 Hz, 1H), 4.74-4.80 (m, 1H), 4.87-4.93 (m, 1H), 5.07 (t, J = 6.7 Hz, 1H), 6.94 (s, 1H), 7.26 (d, J = 11.0 Hz, 1H), 7.46 (d, J = 8.0 Hz, 2H), 8.09 (d, J = 8.6 Hz, 2H), 8.39 (s, 1H). | (ESI+) 513.1 (MH+) | (+) |

TABLE 2

| Compound No. | Structure (A) | 1H NMR (400 MHz) | MS (m/z) | Optical rotation |
|---|---|---|---|---|
| 7A | (2-methylthiazole with dioxolane-dimethyl substituent) | (CDCl3) δ 1.43 (s, 3H), 1.47 (s, 3H), 1.96-2.20 (m, 4H), 2.37-2.49 (m, 1H), 3.19 (s, 3H), 3.93 (dd, J = 7.9, 6.7 Hz, 1H), 4.27 (dd, J = 7.9, 6.7 Hz, 1H), 4.74-4.80 (m, 1H), 4.87-4.93 (m, 1H), 5.07 (t, J = 6.7 Hz, 1H), 6.94 (s, 1H), 7.26 (d, J = 11.0 Hz, 1H), 7.46 (d, J = 8.0 Hz, 2H), 8.09 (d, J = 8.6 Hz, 2H), 8.40 (s, 1H). | (ESI+) 513.1 (MH+) | (−) |
| 8A | (2-methylthiazole with CH(OH)CH2OH substituent) | (CDCl3) δ 1.93-2.19 (m, 4H), 2.36 (brs, 1H), 2.40-2.52 (m, 1H), 3.07-3.14 (m, 1H), 3.18 (s, 3H), 3.69-3.84 (m, 2H), 4.67-4.74 (m, 1H), 4.74-4.82 (m, 1H), 4.86-4.96 (m, 1H), 6.91 (s, 1H), 7.24 (d, J = 11.2 Hz, 1H), 7.46 (d, J = 8.6 Hz, 1H), 8.08 (d, J = 8.6 Hz, 2H), 8.75 (s, 1H). | (ESI+) 437.1 (MH+) | (+) |
| 9A | (2-methylthiazole with CH(OH)CH2OH substituent) | (CDCl3) δ 1.93-2.19 (m, 4H), 2.36 (brs, 1H), 2.40-2.52 (m, 1H), 3.07-3.14 (m, 1H), 3.18 (s, 3H), 3.69-3.84 (m, 2H), 4.67-4.74 (m, 1H), 4.74-4.82 (m, 1H), 4.86-4.96 (m, 1H), 6.91 (s, 1H), 7.24 (d, J = 11.2 Hz, 1H), 7.46 (d, J = 8.6 Hz, 1H), 8.08 (d, J = 8.6 Hz, 2H), 8.75 (s, 1H). | (ESI+) 437.1 (MH+) | (−) |
| 10A | (2-methylthiazole with t-Bu substituent) | (CDCl3) δ 1.26 (s, 9H), 1.90-2.19 (m, 4H), 2.37-2.52 (m, 1H), 3.18 (s, 3H), 4.71-4.96 (m, 2H), 6.58 (s, 1H), 7.19 (d, J = 10.4 Hz, 1H), 7.44-7.49 (m, 2H), 8.05-8.11 (m, 2H), 8.46 (brs, 1H). | (ESI+) 469.1 (MH+) | |
| 11A | (2-methylthiazole with ethyl-O-tetrahydropyranyl substituent) | (CDCl3) δ 1.42-1.85 (m, 6H), 1.90-2.19 (m, 4H), 2.36-2.49 (m, 1H), 2.91 (t, J = 6.7 Hz, 2H), 3.18 (s, 3H), 3.41-3.50 (m, 1H), 3.65 (td, J = 9.8, 6.7 Hz, 1H), 3.71-3.81 (m, 1H), 3.97 (td, J = 9.8, 6.7 Hz, 1H), 4.57 (t, J = 4.3 Hz, 1H), 4.72-4.95 (m, 2H), 6.71 (s, 1H), 7.25 (d, J = 9.8 Hz, 1H), 7.44-7.48 (m, 2H), 8.08 (d, J = 7.9 Hz, 2H), 8.43 (brs, 1H). | (ESI+) 541.2 (MH+) | |

TABLE 3

| 12A | (2-methylthiazole with CH2CH2OH substituent) | (CDCl3) δ 1.91-2.19 (m, 4H), 2.36-2.50 (m, 1H), 2.55 (brs, 1H), 2.85 (t, J = 5.5 Hz, 2H), 3.18 (s, 3H), 3.85 (q, J = 5.5 Hz, 2H), 4.72-4.96 (m, 2H), 6.69 (s, 1H), 7.25 (d, J = 11.6 Hz, 1H), 7.44-7.49 (m, 2H), 8.06-8.11 (m, 2H), 8.48 (brs, 1H). | (ESI+) 457.1 (MH+) | |
|---|---|---|---|---|

TABLE 3-continued

| | | | |
|---|---|---|---|
| 13A | 2-methyl-thiazole-5-sulfonic acid dimethylamide | (CDCl3) δ 1.93-2.19 (m, 4H), 2.41-2.54 (m, 1H), 2.79 (s, 6H), 3.18 (s, 3H), 4.74-4.97 (m, 2H), 7.31 (d, J = 10.4 Hz, 1H), 7.45-7.49 (m, 2H), 7.83 (s, 1H), 8.07-8.12 (m, 2H), 8.67 (brs, 1H). | (ESI+) 520.1 (MH+) |
| 14A | 2-methyl-thiazol-5-yl 4-methylpiperazin-1-yl sulfone | (DMSO-d6) δ 1.82-1.99 (m, 2H), 2.10-2.20 (m, 2H), 2.39-2.41 (m, 4H), 2.51-2.65 (m, 1H), 2.90-3.00 (m, 4H), 3.26 (s, 3H), 4.86-4.95 (m, 1H), 5.00-5.07 (m, 1H), 6.95 (d, J = 10.4 Hz, 1H), 7.48 (d, J = 7.9 Hz, 2H), 7.95 (d, J = 8.6 Hz, 2H), 8.02 (s, 1H), 13.1 (s, 1H). | (ESI+) 575.1 (MH+) |
| 15A | 5-methyl-1,2,4-thiadiazole | (CDCl3) δ 1.93-2.22 (m, 4H), 2.42-2.56 (m, 1H), 3.19 (s, 3H), 4.75-4.97 (m, 2H), 7.32-7.38 (m, 1H), 7.46-7.50 (m, 2H), 8.11 (dd, J = 8.6, 1.8 Hz, 2H), 8.29 (d, J = 1.2 Hz, 1H), 8.91-9.05 (m, 1H). | (ESI+) 414.1 (MH+) |
| 16A | 3,5-dimethyl-1,2,4-thiadiazole | (CDCl3) δ 1.92-2.20 (m, 4H), 2.39-2.56 (m, 1H), 2.51 (s, 3H), 3.18 (s, 3H), 4.73-4.97 (m, 2H), 7.34 (d, J = 10.4 Hz, 1H), 7.44-7.50 (m, 2H), 8.08-8.12 (m, 2H), 8.76 (brs, 1H). | (ESI+) 428.1 (MH+) |
| 17A | 3-ethyl-5-methyl-1,2,4-thiadiazole | (CDCl3) δ 1.33 (t, J = 7.9 Hz, 3H), 1.94-2.20 (m, 4H), 2.42-2.55 (m, 1H), 2.85 (q, J = 7.9 Hz, 2H), 3.20 (s, 3H), 4.75-4.98 (m, 2H), 7.35 (d, J = 10.4 Hz, 1H), 7.45-7.51 (m, 2H), 8.09-8.14 (m, 2H), 8.76 (brs, 1H). | (ESI+) 442.1 (MH+) |
| 18A | 3-methoxy-5-methyl-1,2,4-thiadiazole | (CDCl3) δ 1.93-2.18 (m, 4H), 2.42-2.52 (m, 1H), 3.18 (s, 3H), 4.01 (s, 3H), 4.74-4.83 (m, 1H), 4.88-4.96 (m, 1H), 7.32 (d, J = 10.4 Hz, 1H), 7.46 (d, J = 7.9 Hz, 2H), 8.10 (d, J = 8.6 Hz, 2H), 8.74 (s, 1H). | (ESI+) 444.1 (MH+) |

TABLE 4

| | | | |
|---|---|---|---|
| 19A | 2-methylpyridine | (CDCl3) δ 1.90-2.20 (m, 4H), 2.37-2.46 (m, 1H), 3.16 (s, 3H), 4.70-4.82 (m, 1H), 4.88-4.93 (m, 1H), 7.06 (dd, J = 7.6, 4.9 Hz, 1H), 7.13 (d, J = 10.4 Hz, 1H), 7.48 (d, J = 7.9 Hz, 2H), 7.64 (s, 1H), 7.74 (t, J = 7.9 Hz, 1H), 8.06 (d, J = 8.6 Hz, 2H), 8.21 (d, J = 3.7 Hz, 1H), 8.30 (d, J = 7.9 Hz, 1H). | (ESI+) 407.2 (MH+) |
| 20A | 5-fluoro-2-methylpyridine | (CDCl3) δ 1.91-2.19 (m, 4H), 2.35-2.50 (m, 1H), 3.16 (s, 3H), 4.72-4.95 (m, 2H), 7.13 (d, J = 10.4 Hz, 1H), 7.43-7.51 (m, 3H), 7.64 (brs, 1H), 8.04-8.10 (m, 3H), 8.32 (dd, J = 9.2, 4.3 Hz, 1H). | (ESI+) 425.1 (MH+) |
| 21A | 5-chloro-2-methylpyridine | (CDCl3) δ 1.92-2.20 (m, 4H), 2.36-2.50 (m, 1H), 3.16 (s, 3H), 4.72-4.95 (m, 2H), 7.13 (d, J = 11.0 Hz, 1H), 7.44-7.51 (m, 2H), 7.64 (brs, 1H), 7.70 (dd, J = 8.6, 2.4 Hz, 1H), 8.04-8.10 (m, 2H), 8.16 (d, J = 1.8 Hz, 1H), 8.29 (d, J = 9.8 Hz, 1H). | (ESI+) 441.1 (MH+) |
| 22A | 2-methyl-5-(methylthio)pyridine | (CDCl3) δ 1.92-2.19 (m, 4H), 2.35-2.47 (m, 1H), 2.47 (s, 3H), 3.16 (s, 3H), 4.72-4.95 (m, 2H), 7.12 (d, J = 10.4 Hz, 1H), 7.45-7.50 (m, 2H), 7.62 (brs, 1H), 7.66 (dd, J = 8.6, 2.4 Hz, 1H), 8.04-8.09 (m, 2H), 8.13 (d, J = 1.8 Hz, 1H), 8.25 (d, J = 8.6 Hz, 1H). | (ESI+) 453.2 (MH+) |
| 23A | 5-cyclopropyl-2-methylpyridine | (CDCl3) δ 0.61-0.71 (m, 2H), 0.94-1.04 (m, 2H), 1.77-1.90 (m, 1H), 1.91-2.19 (m, 4H), 2.33-2.48 (m, 1H), 3.16 (s, 3H), 4.70-4.95 (m, 2H), 7.11 (d, J = 10.4 Hz, 1H), 7.35 (dd, J = 8.6, 2.4 Hz, 1H), 7.44-7.50 (m, 2H), 7.59 (brs, 1H), 8.01 (d, J = 2.4 Hz, 1H), 8.03-8.08 (m, 2H), 8.18 (d, J = 8.6 Hz, 1H). | (ESI+) 447.1 (MH+) |

TABLE 4-continued

| | | | |
|---|---|---|---|
| 24A | 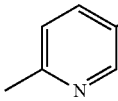 | (CDCl3) δ 1.70 (t, J = 5.8 Hz, 1H), 1.90-2.30 (m, 4H), 2.40-2.47 (m, 1H), 3.16 (s, 3H), 4.69 (d, J = 5.8 Hz, 2H), 4.74-4.80 (m, 1H), 4.87-4.93 (m, 1H), 7.13 (d, J = 10.4 Hz, 1H), 7.48 (d, J = 8.6 Hz, 1H), 7.68 (s, 1H), 7.76 (dd, J = 8.6 Hz, 2.4 Hz, 1H), 8.06 (d, J = 8.6 Hz, 2H), 8.20 (d, J = 2.4 Hz, 1H), 8.30 (d, J = 8.6 Hz, 1H). | (ESI+) 437.1 (MH+) |

TABLE 5

| | | | |
|---|---|---|---|
| 25A | 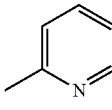 | (CDCl3) δ 1.90-2.17 (m, 4H), 2.40-2.50 (m, 1H), 2.73 (s, 6H), 3.17 (s, 3H), 4.75-4.81 (m, 1H), 4.90-4.95 (m, 1H), 7.17 (d, J = 10.4 Hz, 1H), 7.49 (d, J = 8.0 Hz, 2H), 7.87 (s, 1H), 8.06-8.10 (m, 3H), 8.47 (d, J = 9.8 Hz, 1H), 8.59 (d, J = 2.4 Hz, 1H). | (ESI+) 514.1 (MH+) |
| 26A | 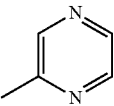 | (CDCl3) δ 1.95-2.14 (m, 4H), 2.39-2.50 (m, 1H), 3.16 (s, 3H), 4.75-4.95 (m, 2H), 7.18 (d, J = 10.4 Hz, 1H), 7.49 (d, J = 8.0 Hz, 2H), 7.57 (brs, 1H), 8.08 (d, J = 8.0 Hz, 2H), 8.19 (d, J = 1.8 Hz, 1H), 8.37 (d, J = 2.5 Hz, 1H), 9.63 (d, J = 1.2 Hz, 1H). | (ESI+) 408.1 (MH+) |
| 27A | 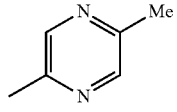 | (CDCl3) δ 1.94-2.18 (m, 4H), 2.37-2.50 (m, 1H), 2.53 (s, 3H), 3.16 (s, 3H), 4.73-4.94 (m, 1H), 7.16 (d, J = 10.4 Hz, 1H), 7.49 (d, J = 8.6 Hz, 2H), 7.50 (brs, 1H), 8.05 (d, J = 1.2 Hz, 2H), 8.08 (d, J = 8.7 Hz, 2H), 9.49 (d, J = 1.2 Hz, 1H). | (ESI+) 422.1 (MH+) |
| 28A | 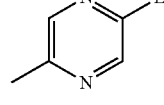 | (CDCl3) δ 1.31 (t, J = 7.3 Hz, 3H), 1.83-2.20 (m, 4H), 2.37-2.51 (m, 1H), 2.82 (q, J = 7.3 Hz, 2H), 3.16 (s, 3H), 4.71-4.96 (m, 2H), 7.16 (d, J = 11.0 Hz, 1H), 7.46-7.51 (m, 2H), 7.52 (brs, 1H), 8.04-8.10 (m, 3H), 9.51 (d, J = 1.2 Hz, 1H). | (ESI+) 436.2 (MH+) |
| 29A | 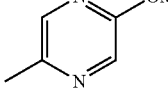 | (CDCl3) δ 1.92-2.20 (m, 4H), 2.37-2.48 (m, 1H), 3.15 (s, 3H), 4.00 (s, 3H), 4.74-4.80 (m, 1H), 4.89-4.93 (m, 1H), 7.15 (d, J = 10.4 Hz, 1H), 7.42 (s, 1H), 7.48 (d, J = 8.6 Hz, 2H), 7.85 (d, J = 1.8 Hz, 1H), 8.07 (d, J = 8.6 Hz, 2H), 9.11 (d, J = 1.8 Hz, 1H). | (ESI+) 438.1 (MH+) |
| 30A | 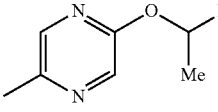 | (CDCl3) δ 1.35 (d, J = 6.1 Hz, 6H), 1.98-2.15 (m, 4H), 2.36-2.47 (m, 1H), 3.16 (s, 3H), 4.74-4.79 (m, 1H), 4.87-4.92 (m, 1H), 5.26 (sep, J = 6.1 Hz, 1H), 7.15 (d, J = 10.4 Hz, 1H), 7.38 (s, 1H), 7.48 (d, J = 8.6 Hz, 2H), 7.77 (d, J = 1.2 Hz, 1H), 8.07 (d, J = 8.6 Hz, 2H), 9.08 (d, J = 1.2 Hz, 1H). | (ESI+) 466.2 (MH+) |

TABLE 6

| | | | |
|---|---|---|---|
| 31A | 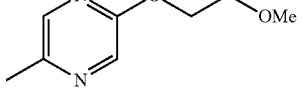 | (CDCl3) δ 1.93-2.18 (m, 4H), 2.36-2.48 (m, 1H), 3.15 (s, 3H), 3.43 (s, 3H), 3.73-3.76 (m, 2H), 4.48-4.50 (m, 2H), 4.74-4.93 (m, 2H), 7.15 (d, J = 11.4 Hz, 1H), 7.42 (brs, 1H), 7.48 (dt, J = 8.6, 1.8 Hz, 2H), 7.91 (d, J = 1.2 Hz, 1H), 8.08 (dt, J = 8.6, 1.8 Hz, 2H), 9.09 (d, J = 1.8 Hz, 1H). | (ESI+) 482.2 (MH+) |
| 32A | 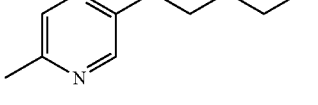 | (CDCl3) δ 1.92-2.19 (m, 6H), 2.35-2.48 (m, 1H), 3.16 (s, 3H), 3.35 (s, 3H), 3.53 (t, J = 6.7 Hz, 2H), 4.40 (t, J = 6.7 Hz, 2H), 4.71-4.95 (m, 2H), 7.15 (d, J = 11.0 Hz, 1H), 7.41 (brs, 1H), 7.45-7.51 (m, 2H), 7.83 (d, J = 1.8 Hz, 1H), 8.05-8.10 (m, 2H), 9.09 (d, J = 1.2 Hz, 1H). | (ESI+) 496.2 (MH+) |
| 33A | 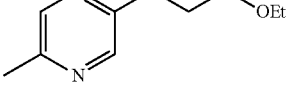 | (CDCl3) δ 1.23 (t, J = 7.3 Hz, 3H), 1.92-2.19 (m, 4H), 2.35-2.48 (m, 1H), 3.15 (s, 3H), 3.58 (q, J = 7.3 Hz, 2H), 3.75-3.81 (m, 2H), 4.44-4.51 (m, 2H), 4.72-4.94 (m, 2H), 7.15 (d, J = 10.4 Hz, 1H), 7.41 (brs, 1H), 7.46-7.50 (m, 2H), 7.90 (d, J = 1.2 Hz, 1H), 8.05-8.09 (m, 2H), 9.08 (d, J = 1.2 Hz, 1H). | (ESI+) 496.2 (MH+) |

TABLE 6-continued

| | | | |
|---|---|---|---|
| 34A | [pyrazine with OCH2CH2SMe and Me substituents] | (CDCl3) δ 1.94-2.17 (m, 4H), 2.20 (s, 3H), 2.37-2.48 (m, 1H), 2.88 (t, J = 6.7 Hz, 2H), 3.16 (s, 3H), 4.51 (t, J = 6.7 Hz, 2H), 4.73-4.81 (m, 1H), 4.86-4.94 (m, 1H), 7.15 (d, J = 10.4 Hz, 1H), 7.42 (s, 1H), 7.48 (d, J = 8.6 Hz, 2H), 7.86 (d, J = 1.2 Hz, 1H), 8.07 (d, J = 8.0 Hz, 2H), 9.09 (d, J = 1.2 Hz, 1H). | (ESI+) 498.1 (MH+) |
| 35A | [pyrazine with SCH2CH2OH and Me substituents] | (CDCl3) δ 1.92-2.20 (m, 4H), 2.37-2.51 (m, 1H), 3.07 (t, J = 5.5 Hz, 1H), 3.16 (s, 3H), 3.36 (t, J = 5.5 Hz, 2H), 3.92 (q, J = 5.5 Hz, 2H), 4.72-4.96 (m, 2H), 7.16 (d, J = 10.4 Hz, 1H), 7.44-7.52 (m, 3H), 8.08 (d, J = 7.9 Hz, 2H), 8.15 (d, J = 1.8 Hz, 1H), 9.40 (d, J = 1.2 Hz, 1H). | (ESI+) 484.1 (MH+) |

TABLE 7

| | | | |
|---|---|---|---|
| 36A | [pyrazine with O-CH2CH2-O-tetrahydropyranyl and Me] | (CDCl3) δ 1.51-1.62 (m, 4H), 1.70-1.83 (m, 2H), 2.00-2.13 (m, 4H), 2.37-2.47 (m, 1H), 3.16 (s, 3H), 3.49-3.53 (m, 1H), 3.78-3.82 (m, 1H), 3.82-3.91 (m, 1H), 4.03-4.09 (m, 1H), 4.45-4.56 (m, 1H), 4.68 (t, J = 3.7 Hz, 1H), 4.70-4.80 (m, 1H), 4.87-4.92 (m, 1H), 7.15 (d, J = 10.4 Hz, 1H), 7.42 (s, 1H), 7.48 (d, J = 8.0 Hz, 2H), 7.89 (d, J = 1.8 Hz, 1H), 8.07 (d, J = 8.6 Hz, 2H), 9.09 (d, J = 1.8 Hz, 1H). | (ESI+) 552.2 (MH+) |
| 37A | [pyrazine with OCH2CH2OH and Me] | (DMSO-d6) δ 1.85-2.00 (m, 2H), 2.05-2.25 (m, 2H), 2.52-2.56 (m, 1H), 3.24 (s, 3H), 3.70 (dd, J = 5.5 Hz, 4.9 Hz, 2H), 4.28 (t, J = 4.9 Hz, 2H), 4.85 (t, J = 5.5 Hz, 1H), 4.83-4.95 (m, 1H), 4.96-5.06 (m, 1H), 6.70 (d, J = 10.4 Hz, 1H), 7.49 (d, J = 8.6 Hz, 2H), 7.79 (d, J = 8.6 Hz, 2H), 8.24 (d, J = 1.8 Hz, 1H), 8.75 (d, J = 1.8 Hz, 1H), 10.6 (s, 1H). | (ESI+) 468.1 (MH+) |
| 38A | [pyrazine with (R)-dimethyldioxolane and Me] | (CDCl3) δ 1.49 (s, 3H), 1.52 (s, 3H), 1.92-2.21 (m, 4H), 2.38-2.52 (m, 1H), 3.16 (s, 3H), 4.01 (dd, J = 8.6, 6.1 Hz, 1H), 4.45 (dd, J = 8.6, 6.7 Hz, 1H), 4.73-4.96 (m, 2H), 5.21 (t, J = 6.7 Hz, 1H), 7.18 (d, J = 10.4 Hz, 1H), 7.49 (d, J = 7.9 Hz, 2H), 7.61 (brs, 1H), 8.08 (d, J = 7.9 Hz, 2H), 8.38 (d, J = 1.2 Hz, 1H), 9.53 (d, J = 1.2 Hz, 1H). | (ESI+) 508.2 (MH+) (−) |
| 39A | [pyrazine with (S)-dimethyldioxolane and Me] | (CDCl3) δ 1.49 (s, 3H), 1.51 (s, 3H), 1.92-2.21 (m, 4H), 2.38-2.52 (m, 1H), 3.16 (s, 3H), 4.01 (dd, J = 8.6, 6.7 Hz, 1H), 4.45 (dd, J = 8.6, 6.7 Hz, 1H), 4.73-4.97 (m, 2H), 5.21 (t, J = 6.7 Hz, 1H), 7.18 (d, J = 10.4 Hz, 1H), 7.46-7.51 (m, 2H), 7.60 (brs, 1H), 8.06-8.10 (m, 2H), 8.38 (s, 1H), 9.53 (d, J = 1.2 Hz, 1H). | (ESI+) 508.2 (MH+) (+) |
| 40A | [pyrazine with (R)-CH(OH)CH2OH and Me] | (CD3OD) δ 1.85-2.05 (m, 2H), 2.08-2.28 (m, 2H), 2.56-2.70 (m, 1H), 3.16 (s, 3H), 3.74 (dd, J = 11.6, 5.5 Hz, 1H), 3.85 (dd, J = 11.6, 4.9 Hz, 1H), 4.73-4.97 (m, 3H), 6.85 (d, J = 10.4 Hz, 1H), 7.53-7.58 (m, 2H), 8.00-8.05 (m, 2H), 8.48 (d, J = 1.2 Hz, 1H), 9.30 (d, J = 1.8 Hz, 1H). | (ESI+) 468.1 (MH+) (−) |

TABLE 8

| | | | |
|---|---|---|---|
| 41A | [pyrazine with (S)-CH(OH)CH2OH and Me] | (CD3OD) δ 1.86-2.06 (m, 2H), 2.09-2.29 (m, 2H), 2.56-2.71 (m, 1H), 3.16 (s, 3H), 3.74 (dd, J = 11.6, 6.1 Hz, 1H), 3.85 (dd, J = 11.6, 4.9 Hz, 1H), 4.74-5.01 (m, 3H), 6.86 (d, J = 10.4 Hz, 1H), 7.54-7.58 (m, 2H), 8.00-8.06 (m, 2H), 8.48 (d, J = 1.2 Hz, 1H), 9.30 (d, J = 1.8 Hz, 1H). | (ESI+) 468.1 (MH+) (+) |

TABLE 8-continued

| | | | |
|---|---|---|---|
| 42A | 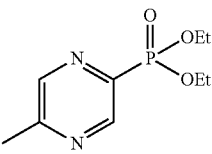 | (CDCl3) δ 1.36 (t, J = 7.3 Hz, 6H), 1.93-2.22 (m, 4H), 2.39-2.53 (m, 1H), 3.17 (s, 3H), 4.15-4.33 (m, 4H), 4.74-4.97 (m, 2H), 7.21 (d, J = 10.4 Hz, 1H), 7.45-7.51 (m, 2H), 7.74 (brs, 1H), 8.08-8.12 (m, 2H), 8.71-8.73 (m, 1H), 9.78 (d, J = 1.2 Hz, 1H). | (ESI+) 544.2 (MH+) |
| 43A | 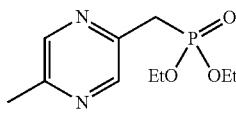 | (CDCl3) δ 1.85 (t, J = 7.3 Hz, 6H), 1.98-2.17 (m, 4H), 2.39-2.50 (m, 1H), 3.16 (s, 3H), 3.39 (d, J = 21.4 Hz, 2H), 4.06-4.13 (m, 4H), 4.75-4.80 (m, 1H), 4.88-4.94 (m, 1H), 7.18 (d, J = 10.4 Hz, 1H), 7.49 (d, J = 8.0 Hz, 2H), 7.57 (s, 1H), 8.08 (d, J =8.0 Hz, 2H), 8.23 (t, J = 2.4 Hz, 1H), 9.54 (s, 1H). | (ESI+) 558.2 (MH+) |
| 44A | 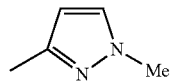 | (CDCl3) δ 1.91-2.14 (m, 4H), 2.32-2.43 (m, 1H), 3.15 (s, 3H), 3.76 (s, 3H), 4.71-4.92 (m, 2H), 6.76 (d, J = 2.5 Hz, 1H), 7.13 (d, J = 10.4 Hz, 1H), 7.26 (d, J = 3.7 Hz, 1H), 7.44 (brs, 1H), 7.45 (dt, J = 8.6, 1.8 Hz, 2H), 8.03 (dt, J = 8.6, 1.8 Hz, 2H). | (ESI+) 410.1 (MH+) |
| 45A | 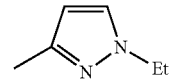 | (CDCl3) δ 1.41 (t, J = 7.3 Hz, 3H), 1.88-2.18 (m, 4H), 2.30-2.45 (m, 1H), 3.16 (s, 3H), 4.01 (q, J = 7.3 Hz, 2H), 4.69-4.94 (m, 2H), 6.76 (d, J = 1.8 Hz, 1H), 7.12 (d, J = 10.4 Hz, 1H), 7.30 (d, J = 2.4 Hz, 1H), 7.43-7.50 (m, 3H), 8.04 (d, J = 8.6 Hz, 1H). | (ESI+) 424.2 (MH+) |
| 46A | 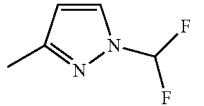 | (CDCl3) δ 1.93-2.17 (m, 4H), 2.35-2.46 (m, 1H), 3.16 (s, 3H), 4.72-4.92 (m, 2H), 7.05 (d, J = 3.0 Hz, 1H), 7.10 (brs, 1H), 7.15 (d, J = 10.4 Hz, 1H), 7.46 (dt, J = 8.0, 1.8 Hz, 21H), 7.71 (d, J = 2.9 Hz, 1H), 8.06 (dt, J = 8.6, 1.8 Hz, 2H). | (ESI+) 446.1 (MH+) |

TABLE 9

| | | | |
|---|---|---|---|
| 47A | 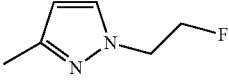 | (CDCl3) δ 1.93-2.15 (m, 4H), 2.34-2.42 (m, 1H), 3.19 (s, 3H), 4.21 (t, J = 4.9 Hz, 1H), 4.28 (t, J = 4.9 Hz, 1H), 4.61 (t, J = 4.3 Hz, 1H), 4.72 (t, J = 4.3 Hz, 1H), 4.71-4.78 (m, 1H), 4.85-4.90 (m, 1H), 6.81 (d, J = 2.5 Hz, 1H), 7.12 (d, J = 10.4 Hz, 1H), 7.37 (d, J = 2.5 Hz, 1H), 7.45-7.47 (m, 1H), 7.46 (d, J = 8.0 Hz, 2H), 8.05 (d, J = 8.6 Hz, 2H). | (ESI+) 442.1 (MH+) |
| 48A | 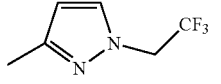 | (CDCl3) δ 1.92-2.13 (m, 4H), 2.33-2.46 (m, 2H), 3.10 (s, 3H), 4.52 (q, J = 8.6 Hz, 2H), 4.72-4.92 (m, 2H), 6.94 (d, J = 2.5 Hz, 1H), 7.12 (d, J = 10.4 Hz, 1H), 7.41 (d, J = 2.5 Hz, 1H), 7.46 (dt, J = 8.0, 1.8 Hz, 2H), 7.51 (brs, 1H), 8.05 (dt, J = 9.0, 1.8 Hz, 2H). | (ESI+) 478.1 (MH+) |
| 49A | 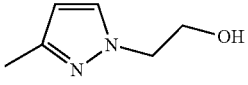 | (CDCl3) δ 1.91-2.16 (m, 4H), 2.33-2.45 (m, 1H), 2.47 (t, J = 5.5 Hz, 1H), 3.16 (s, 3H), 3.90 (q, J = 4.89 Hz, 2H), 4.10 (dd, J = 4.9, 1.6 Hz, 2H), 4.72-4.93 (m, 2H), 6.80 (d, J = 2.5 Hz, 1H), 7.12 (d, J = 10.4 Hz, 1H), 7.35 (d, J = 2.5 Hz, 1H), 7.45 (brs, 1H), 7.46 (dt, J = 8.6, 1.8 Hz, 2H), 8.05 (dt, J = 8.0, 1.8 Hz, 2H). | (ESI+) 440.1 (MH+) |
| 50A | 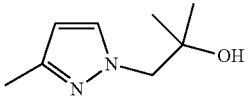 | (CDCl3) δ 1.13 (s, 6H), 1.92-2.16 (m, 4H), 2.32-2.42 (m, 1H), 3.16 (s, 3H), 3.28 (brs, 1H), 3.91 (s, 2H), 4.72-4.80 (m, 1H), 4.84-4.92 (m, 1H), 6.82 (d, J = 2.4 Hz, 1H), 7.12 (d, J = 11.0 Hz, 1H), 7.32 (d, J = 2.4 Hz, 1H), 7.46 (m, 2H), 8.06 (d, J = 7.9 Hz, 1H). | (ESI+) 468.2 (MH+) |
| 51A | 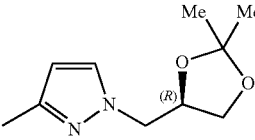 | (CDCl3) δ 1.32 (s, 3H), 1.36 (s, 3H), 1.96-2.11 (m, 2H), 2.33-2.44 (m, 1H), 3.16 (s, 3H), 3.68 (dd, J = 8.6 Hz, 6.1 Hz, 1H), 4.01 (dd, J = 8.6 Hz, 6.1 Hz, 1H), 4.06-4.08 (m, 2H), 4.32-4.38 (m, 1H), 4.71-4.79 (m, 1H), 4.84-4.93 (m, 1H), 6.79 (d, J = 2.4 Hz, 1H), 7.11 (d, J = 10.4 Hz, 1H), 7.37 (d, J = 2.4 Hz, 1H), 7.44 (m, 3H), 8.05 (d, J =6.1 Hz, 2H). | (ESI+) 510.2 (MH+) (+) |

TABLE 10

| No. | Structure (A) | 1H NMR (400 MHz) | MS (m/z) | |
|---|---|---|---|---|
| 52A | 3-methylpyrazole-CH2-[(S)-2,2-dimethyl-1,3-dioxolan-4-yl] | (CDCl3) δ 1.32 (s, 3H), 1.36 (s, 3H), 1.91-2.16 (m, 4H), 2.31-2.46 (m, 1H), 3.16 (s, 3H), 3.68 (dd, J = 8.6, 6.1 Hz, 1H), 4.01 (dd, J = 8.6, 6.1 Hz, 1H), 4.05-4.09 (m, 2H), 4.31-4.40 (m, 1H), 4.70-4.94 (m, 2H), 6.79 (d, J = 2.4 Hz, 1H), 7.11 (d, J = 10.4 Hz, 1H), 7.37 (d, J = 1.8 Hz, 1H), 7.42-7.49 (m, 3H), 8.02-8.07 (m, 2H). | (ESI+) 397.1 (MH+) | (+) |
| 53A | 3-methylpyrazole-CH2-[(R)-CH(OH)-CH2OH] | (CD3OD) δ 1.83-2.01 (m, 2H), 2.09-2.24 (m, 2H), 2.54-2.66 (m, 1H), 3.15 (s, 3H), 3.45 (d, J = 5.5 Hz, 2H), 3.89-3.94 (m, 1H), 4.00 (dd, J = 13.4, 7.4 Hz, 1H), 4.16 (dd, J = 13.4, 4.0 Hz, 1H), 4.73-4.95 (m, 2H), 6.52 (d, J = 2.4 Hz, 1H), 6.78 (d, J = 10.4 Hz, 1H), 7.51 (d, J = 2.4 Hz, 1H), 7.52 (d, J = 8.6 Hz, 2H), 8.02 (d, J = 8.6 Hz, 2H). | (ESI+) 470.2 (MH+) | (+) |
| 54A | 3-methylpyrazole-CH2-[(S)-CH(OH)-CH2OH] | (CD3OD) δ 1.81-2.01 (m, 2H), 2.08-2.26 (m, 2H), 2.52-2.67 (m, 1H), 3.15 (s, 3H), 3.45 (d, J = 5.5 Hz, 2H), 3.88-3.95 (m, 1H), 4.00 (dd, J = 14.1, 6.7 Hz, 1H), 4.16 (dd, J = 14.1, 4.3 Hz, 1H), 4.73-4.96 (m, 2H), 6.52 (d, J = 2.4 Hz, 1H), 6.78 (d, J = 10.4 Hz, 1H), 7.49-7.55 (m, 3H), 7.99-8.05 (m, 2H). | (ESI+) (MH+) | (−) |
| 55A | 3-methylisoxazole | (CDCl3) δ 1.92-2.20 (m, 4H), 2.36-2.50 (m, 1H), 3.16 (s, 3H), 4.72-4.95 (m, 2H), 7.14 (d, J = 1.8 Hz, 1H), 7.17 (d, J = 10.4 Hz, 1H), 7.44-7.49 (m, 2H), 7.88-7.99 (m, 1H), 8.07 (d, J = 8.6 Hz, 2H), 8.31 (d, J = 1.8 Hz, 1H). | (ESI+) 397.1 (MH+) | |
| 56A | 2-methyl-6-methoxybenzothiazole | (DMSO-d6) δ 1.85-2.02 (m, 2H), 2.10-2.25 (m, 2H), 2.50-2.60 (m, 1H), 3.26 (s, 3H), 4.87-4.93 (m, 1H), 5.00-5.05 (m, 1H), 6.92 (d, J = 10.4 Hz, 1H), 7.03 (dd, J = 9.2, 2.4 Hz, 1H), 7.50 (d, J = 8.6 Hz, 1H), 7.56 (d, J = 2.4 Hz, 1H), 7.64 (d, J = 9.2 Hz, 1H), 7.96 (d, J = 8.6 Hz, 2H), 12.6 (s, 1H). | (ESI+) 493.1 (MH+) | |

TABLE 11

| No. | Structure (A) | 1H NMR (400 MHz) | MS (m/z) |
|---|---|---|---|
| 57A | 2-methyl-6-(OCHF2)benzothiazole | (DMSO-d6) δ 1.82-2.15 (m, 2H), 2.15-2.25 (m, 2H), 2.53-2.60 (m, 1H), 3.26 (s, 3H), 4.85-4.95 (m, 1H), 5.00-5.07 (m, 1H), 6.96 (d, J = 10.4 Hz, 1H), 7.21 (t, J = 86.2 Hz, 1H), 7.27 (dd, J = 8.6, 2.4 Hz, 1H), 7.50 (d, J = 7.9 Hz, 1H), 7.77 (d, J = 7.9 Hz, 1H), 7.88 (s, 1H), 7.96 (d, J = 8.6 Hz, 2H), 12.7 (s, 1H). | (ESI+) 529.1 (MH+) |
| 58A | 2-methylthiazolo[5,4-b]pyridine-5-O-CH2CH2-OMe | (DMSO-d6) δ 1.95-2.17 (m, 4H), 2.39-2.51 (m, 1H), 3.19 (s, 3H), 3.45 (s, 3H), 3.77-3.79 (m, 2H), 4.54-4.67 (m, 2H), 4.75-4.95 (m, 2H), 6.88 (d, J = 8.6 Hz, 1H), 7.32 (d, J = 10.4 Hz, 1H), 7.49 (q, J = 8.6 Hz, 2H), 7.79 (d, J = 9.2 Hz, 1H), 8.10 (d, J = 1.8 Hz, 2H), 8.41 (brs, 1H). | (ESI+) 538.1 (MH+) |
| 59A | 2-methylthiazolo[5,4-b]pyridine-5-O-CH2-CO2Et | (CDCl3) δ 1.30 (t, J = 7.3 Hz, 3H), 1.91-2.20 (m, 4H), 2.38-2.52 (m, 1H), 3.19 (s, 3H), 4.26 (q, J = 7.3 Hz, 2H), 4.74-4.99 (m, 2H), 4.96 (s, 2H), 6.95 (d, J = 8.6 Hz, 1H), 7.32 (d, J = 10.4 Hz, 1H), 7.49 (d, J = 8.6 Hz, 1H), 7.84 (d, J = 8.6 Hz, 1H), 8.10 (d, J = 8.6 Hz, 2H), 8.42 (brs, 1H). | (ESI+) 566.1 (MH+) |

TABLE 12

| No. | Structure (A) | 1H NMR (400 MHz) | MS (m/z) |
|---|---|---|---|
| 60A | 2-methyl-5-phenyl-1,3,4-thiadiazole | (CDCl3) δ 1.16-1.22 (m, 2H), 1.46-1.50 (m, 2H), 1.98-2.20 (m, 4H), 2.44-2.54 (m, 1H), 2.57-2.63 (m, 1H), 4.77-4.83 (m, 1H), 4.90-4.93 (m, 1H), 7.36 (d, J = 11.0 Hz, 1H), 7.42-7.45 (m, 3H), 7.48 (d, J = 8.0 Hz, 2H), 8.09 (d, J = 8.0 Hz, 2H), 8.11-8.14 (m, 2H), 8.88 (s, 1H). | (ESI+) 516.2 (MH+) |

TABLE 12-continued

| No. | Structure (A) | 1H NMR (400 MHz) | MS (m/z) |
|---|---|---|---|
| 61A | [structure with OEt, pyridine, methyl] | (CDCl3) δ 1.41 (t, J = 7.3 Hz, 3H), 1.91-2.19 (m, 4H), 2.33-2.48 (m, 1H), 3.15 (s, 3H), 4.04 (q, J = 7.3 Hz, 2H), 4.71-4.94 (m, 2H), 7.11 (d, J = 10.4 Hz, 1H), 7.27 (dd, J = 9.2, 3.1 Hz, 1H), 7.45-7.50 (m, 2H), 7.54 (brs, 1H), 7.88 (d, J = 3.1 Hz, 1H), 8.03-8.08 (m, 2H), 8.22 (d, J = 9.2 Hz, 1H). | (ESI+) 451.2 (MH+) |
| 62A | [thiazolopyridine structure with NMe2] | (CDCl3) δ 1.93-2.20 (m, 4H), 2.29-2.53 (m, 1H), 2.35 (s, 6H), 2.74 (t, J = 5.5 Hz, 2H), 3.19 (s, 3H), 4.48 (t, J = 5.5 Hz, 2H), 4.73-4.96 (m, 2H), 6.86 (d, J = 9.2 Hz, 1H), 7.32 (d, J = 10.4 Hz, 1H), 7.49 (d, J = 8.6 Hz, 2H), 7.78 (d, J = 9.2 Hz, 1H), 8.10 (d, J = 8.6 Hz, 2H). | (ESI+) 551.2 (MH+) |

EXAMPLE 7

(E)-2-[4-(cyclopropylthio)phenyl]-3-[(1α,3α,4α)-3,4-difluorocyclopentyl]acrylic acid ethyl ester

[Chemical formula 14]

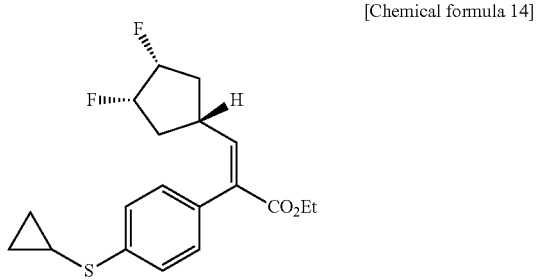 [SMILES: CCOC(=O)/C(=C/[C@H]1C[C@@H](F)[C@@H](F)C1)c1ccc(SC2CC2)cc1]

(1α,3α,4α)-(3,4-Difluorocyclopentyl)methyltriphenylphosphonium iodide (60.9 g) was suspended in tetrahydrofuran (186 mL). Lithium bis(trimethylsilyl)amide (a 1 mol/L tetrahydrofuran solution, 120 mL) was added to the suspension cooled in an ice bath, and the mixture was stirred for 1 hour while cooled in the ice bath. A solution of [(4-cyclopropylthio)phenyl]oxoacetic acid ethyl ester (25.0 g) in tetrahydrofuran (120 mL) was added dropwise to the reaction mixture cooled in an ice bath, and the resultant mixture was stirred for 1 hour while cooled in the ice bath and further stirred at room temperature for 5 hours. Water (230 mL) was added to the reaction mixture, and the pH of the mixture was adjusted to 6 with 1 mol/L hydrochloric acid. Then, tetrahydrofuran was evaporated under reduced pressure, and the residue was extracted with ethyl acetate (2×540 mL). The ethyl acetate extracts were combined, washed with saturated brine (180 mL), dried over anhydrous sodium sulfate, filtrated, and concentrated under reduced pressure. The residue was purified by silica gel column chromatography (eluent; hexane:ethyl acetate=4:1) to give (E)-2-[4-(cyclopropylthio)phenyl]-3-[(1α,3α,4α)-3,4-difluorocyclopentyl]acrylic acid ethyl ester (12.2 g), (Z)-2-[4-(cyclopropylthio)phenyl]-3-[(1α,3α,4α)-3,4-difluorocyclopentyl]acrylic acid ethyl ester (7.71 g), and 2-[4-(cyclopropylthio)phenyl]-3-[(1α,3α,4α)-3,4-difluorocyclopentyl]acrylic acid ethyl ester (14.5 g) (a mixture of E-form and Z-form). Of these, only the title compound was used in the next step.

MS (EI) m/z: 352 (M+)

HRMS (EI) for $C_{19}H_{22}F_2N_2O_2S$ (M+): calcd., 352.1309; found, 352.1302.

$^1$H NMR (400 MHz, CDCl$_3$) δ 0.69-0.73 (m, 2H), 1.04-1.11 (m, 2H), 1.28 (t, J=7.3 Hz, 3H), 1.89-2.03 (m, 2H), 2.06-2.21 (m, 3H), 2.58-2.69 (m, 1H), 4.22 (q, J=7.3 Hz, 2H), 4.73-4.92 (m, 2H), 6.97 (d, J=10.4 Hz, 1H), 7.03-7.37 (m, 2H).

EXAMPLE 8

(E)-2-[4-(cyclopropylsulfonyl)phenyl]-3-[(1α,3α,4α)-3,4-difluorocyclopentyl]acrylic acid ethyl ester

[Chemical formula 15]

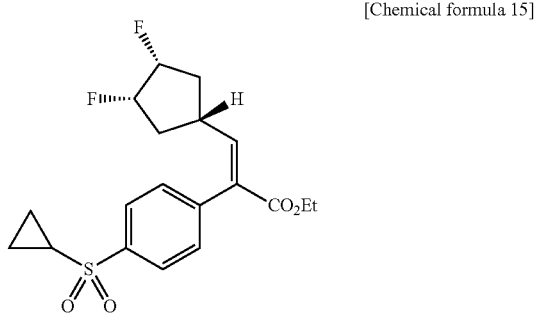 [SMILES: CCOC(=O)/C(=C/[C@H]1C[C@@H](F)[C@@H](F)C1)c1ccc(S(=O)(=O)C2CC2)cc1]

(E)-2-[4-(cyclopropylthio)phenyl]-3-[(1α,3α,4α)-3,4-difluorocyclopentyl]acrylic acid ethyl ester (8.81 g) was dissolved in dichloromethane (90 mL). m-Chloroperoxybenzoic acid (14.6 g) was added to the prepared solution cooled in an ice bath, and the mixture was stirred for 1 hour while cooled in the ice bath and further stirred at room temperature for 1 hour. Insoluble materials in the reaction mixture were removed by filtration, and the filtrate was diluted with dichloromethane (150 mL). The obtained dichloromethane solution was washed with a 10% aqueous sodium sulfite solution (2×35 mL), a saturated aqueous sodium hydrogen carbonate solution (2×35 mL), and water (35 mL), dried over anhydrous sodium sulfate, filtrated, and concentrated under reduced pressure. The residue was purified by silica gel column chromatography (eluent; hexane:ethyl acetate=1:1) to give (E)-2-[4-(cyclopropylsulfonyl)phenyl]-3-[(1α,3α,4α)-3,4-difluorocyclopentyl]acrylic acid ethyl ester (9.54 g).

MS (EI) m/z: 384 (M+)

HRMS (EI) for $C_{19}H_{22}F_2N_2O_4S$ (M+): calcd, 384.1207; found, 384.1163.

$^1$H NMR (400 MHz, CDCl$_3$) δ 1.03-1.10 (m, 2H), 1.30 (t, J=7.3 Hz, 3H), 1.34-1.41 (m, 2H), 1.91-2.17 (m, 4H), 2.47-2.58 (m, 2H), 4.24 (q, J=7.3 Hz, 2H), 4.74-4.94 (m, 2H), 7.08 (d, J=10.4 Hz, 1H), 7.32-7.35 (m, 2H), 7.87-7.92 (m, 2H).

EXAMPLE 9

(E)-2-[4-(cyclopropylsulfonyl)phenyl]-3-[(1α,3α,4α)-3,4-difluorocyclopentyl]acrylic acid

[Chemical formula 16]

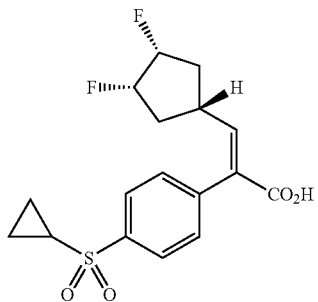

A mixed solution of concentrated sulfuric acid (15.0 mL), acetic acid (80.0 mL) and water (48.0 mL) was added to (E)-2-[4-(cyclopropylsulfonyl)phenyl]-3-[(1α,3α,4α)-3,4-difluorocyclopentyl]acrylic acid ethyl ester (9.54 g), and the mixture was stirred under heating at 98° C. (internal temperature) for 6 hours. After allowed to cool, the reaction mixture was evaporated under reduced pressure. Water (80 mL) was added to the residue, and the precipitate was collected by filtration and washed with water. The collected precipitate was dissolved in a saturated aqueous sodium hydrogen carbonate solution (200 mL) and washed with dichloromethane (50 mL×2). Concentrated hydrochloric acid was added to the aqueous layer, while cooled in an ice bath, to make it acidic (pH=1), and the precipitate was collected by filtration. The collected precipitate was washed with water (100 mL) to give (E)-2-[4-(cyclopropylsulfonyl)phenyl]-3-[(1α,3α,4α)-3,4-difluorocyclopentyl]acrylic acid (7.79 g).

MS (EI) m/z: 356 (M$^+$).

HRMS (EI) for $C_{17}H_{18}F_2N_2O_4S$ (M$^+$): calcd., 356.0894; found, 356.0870.

$^1$H NMR (400 MHz, CDCl$_3$) δ 1.05-1.10 (m, 2H), 1.30-1.41 (m, 2H), 1.91-2.19 (m, 4H), 2.46-2.62 (m, 2H), 4.76-4.94 (m, 2H), 7.24 (d, J=11.0 Hz, 1H), 7.34-7.36 (m, 2H), 7.91-7.93 (m, 2H).

EXAMPLE 10

(E)-2-[4-(cyclopropylsulfonyl)phenyl]-3-[(1α,3α,4α)-3,4-difluorocyclopentyl]-N-(thiazol-2-yl)acrylamide (compound 1B of the present invention)

[Chemical formula 17]

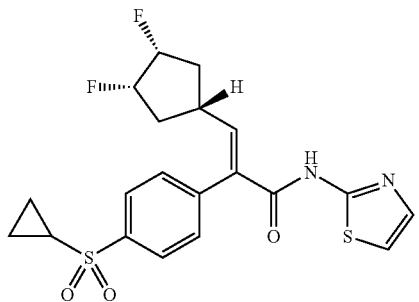

Thionyl chloride (1.00 mL) was added to (E)-2-[4-(cyclopropylsulfonyl)phenyl]-3-[(1α,3α,4α)-3,4-difluorocyclopentyl]acrylic acid (108 mg), and the mixture was heated to reflux for 1.5 hours. After the mixture was cooled to room temperature, thionyl chloride was removed by evaporation. Toluene (0.5 mL) was added to the mixture, and the resultant mixture was evaporated under reduced pressure. The obtained residue was dissolved in anhydrous tetrahydrofuran (0.4 mL). A solution of 2-aminothiazole (30.3 mg) in pyridine (0.40 mL) was added to the prepared solution cooled in a salted ice bath, and the mixture was stirred at room temperature for 1 hour. The reaction mixture was diluted with ethyl acetate (5 mL) and washed sequentially with 1 mol/L hydrochloric acid (8 mL×2), a saturated aqueous sodium hydrogen carbonate solution (3 mL), and saturated brine (3 mL), dried over anhydrous sodium sulfate, and filtrated, and the solvent was evaporated under reduced pressure. The obtained residue was purified by silica gel column chromatography (eluent; chloroform:acetone=20:1), and the obtained compound was washed with diethyl ether to give (E)-2-[4-(cyclopropylsulfonyl)phenyl]-3-[(1α,3α,4α)-3,4-difluorocyclopentyl]-N-(thiazol-2-yl)acrylamide (66.5 mg).

MS (ESI$^+$) m/z: 439.1 (MH$^+$).

HRMS (ESI$^+$) for $C_{20}H_{21}F_2N_2O_3S_2$ (MH$^+$): calcd., 439.09616; found, 439.09701.

$^1$H NMR (400 MHz, CDCl$_3$) δ 1.17 (ddd, J=13.4, 6.7, 2.5 Hz, 2H), 1.45 (ddd, J=10.4, 6.1, 1.8 Hz, 2H), 1.93-2.17 (m, 4H), 2.37-2.17 (m, 1H), 2.57 (tt, J=8.0, 4.9 Hz, 1H), 4.73-4.94 (m, 2H), 7.03 (d, J=3.7 Hz, 1H), 7.27 (d, J=9.4 Hz, 1H), 7.41 (d J=3.67 Hz, 1H), 7.45 (dt, J=8.6, 1.8 Hz, 2H), 8.03 (dt, J=8.5, 1.8 Hz, 2H), 8.51 (brs, 1H)

EXAMPLE 11

Compounds 2B to 109B of the present invention were produced according to the same procedure as in Example 10.

In the following Tables, the optical rotations of the compounds 6B and 7B of the present invention were measured using methanol as a solvent, and the optical rotations of the rest of the compounds of the present invention were measured using chloroform.

[Chemical formula 18]

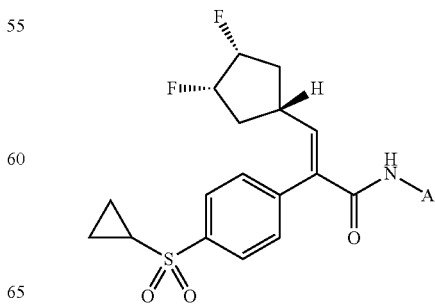

TABLE 13

| Compound No. | Structure (A) | 1H NMR (400 MHz) | MS (m/z) | Optical rotation |
|---|---|---|---|---|
| 2B | 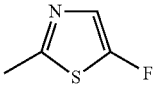 | (CDCl3) δ 1.13-1.20 (m, 2H), 1.42-1.48 (m, 2H), 1.89-2.18 (m, 4H), 2.34-2.48 (m, 1H), 2.52-2.61 (m, 1H), 4.72-4.94 (m, 2H), 7.00 (d, J = 2.4 Hz, 1H), 7.26 (d, J = 10.4 Hz, 1H), 7.40-7.45 (m, 2H), 8.01-8.06 (m, 2H), 8.15 (s, 1H). | (ESI+) 457.1 (MH+) | |
| 3B | 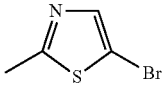 | (CDCl3) δ 1.13-1.21 (m, 2H), 1.42-1.48 (m, 2H), 1.92-2.18 (m, 4H), 2.36-2.48 (m, 1H), 2.52-2.61 (m, 1H), 4.72-4.95 (m, 2H), 7.26-7.30 (m, 1H), 7.33 (s, 1H), 7.41-7.45 (m, 2H), 8.01-8.06 (m, 2H), 8.42 (s, 1H). | (ESI+) 517.0 (MH+) | |
| 4B | 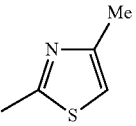 | (CDCl3) δ 1.12-1.21 (m, 2H), 1.42-1.49 (m, 2H), 1.90-2.16 (m, 4H), 2.29 (s, 3H), 2.37-2.47 (m, 1H), 2.53-2.62 (m, 1H), 4.69-4.94 (m, 2H), 6.57 (d, J = 1.2 Hz, 1H), 7.27 (d, J = 10.4 Hz, 1H), 7.40-7.54 (m, 2H), 7.99-8.05 (m, 2H), 8.40 (brs, 1H). | (ESI+) (453.1 MH+) | |
| 5B | 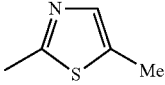 | (DMSO-d6) δ 0.99-1.20 (m, 4H), 1.81-2.00 (m, 2H), 2.07-2.55 (m, 2H), 2.33 (d, J = 1.2 Hz, 3H), 2.42-2.60 (m, 1H), 2.85-2.94 (m, 1H), 4.83-5.09 (m, 2H), 6.80 (d, J = 10.4 Hz, 1H), 7.18 (d, J = 1.2 Hz, 1H), 7.43-7.48 (m, 2H), 7.88-7.93 (m, 2H). | (ESI+) 453.1 (MH+) | |
| 6B | 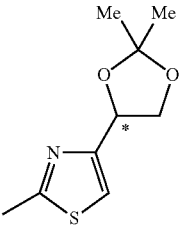 | (CDCl3) δ 1.14-1.20 (m, 2H), 1.43 (s, 3H), 1.45-1.47 (m, 2H), 1.47 (s, 3H), 1.93-2.16 (m, 4H), 2.36-2.47 (m, 1H), 2.55-2.62 (m, 1H), 3.93 (dd, J = 8.0, 6.7 Hz, 1H), 4.27 (dd, J = 8.0, 6.7 Hz, 1H), 4.73-4.81 (m, 1H), 4.84-4.94 (m, 1H), 5.08 (t, J = 6.7 Hz, 1H), 6.94 (s, 1H), 7.27 (d, J = 10.4 Hz, 1H), 7.43 (d, J = 8.6 Hz, 2H), 8.04 (d, J = 8.6 Hz, 2H), 8.45 (s, 1H). | (ESI+) 539.1 (MH+) | (+) |

TABLE 14

| 7B | 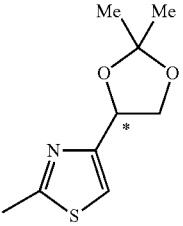 | (CDCl3) δ 1.14-1.20 (m, 2H), 1.43 (s, 3H), 1.45-1.47 (m, 2H), 1.47 (s, 3H), 1.93-2.16 (m, 4H), 2.36-2.47 (m, 1H), 2.55-2.62 (m, 1H), 3.93 (dd, J = 8.0, 6.7 Hz, 1H), 4.27 (dd, J = 8.0, 6.7 Hz, 1H), 4.73-4.81 (m, 1H), 4.84-4.94 (m, 1H), 5.08 (t, J = 6.7 Hz, 1H), 6.94 (s, 1H), 7.27 (d, J = 10.4 Hz, 1H), 7.43 (d, J = 8.6 Hz, 2H), 8.04 (d, J = 8.6 Hz, 2H), 8.45 (s, 1H). | (ESI+) 539.1 (MH+) | (−) |
|---|---|---|---|---|
| 8B | 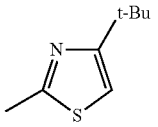 | (CDCl3) δ 1.13-1.20 (m, 2H), 1.26 (s, 9H), 1.41-1.49 (m, 2H), 1.91-2.19 (m, 4H), 2.37-2.50 (m, 1H), 2.53-2.63 (m, 1H), 4.71-4.95 (m, 2H), 6.59 (s, 1H), 7.20 (d, J = 10.4 Hz, 1H), 7.42-7.47 (m, 2H), 8.01-8.06 (m, 2H), 8.44 (brs, 1H). | (ESI+) 495.2 (MH+) | |
| 9B | 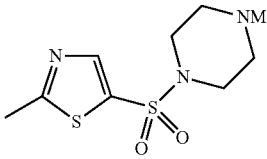 | (CDCl3) δ 1.12-1.20 (m, 2H), 1.44-1.48 (m, 2H), 1.95-2.17 (m, 4H), 2.30 (s, 3H), 2.43-2.54 (m, 6H), 3.07-3.16 (m, 4H), 4.74-4.97 (m, 2H), 7.30 (d, J = 10.4 Hz, 1H), 7.44 (d, J = 8.6 Hz, 2H), 7.81 (s, 1H), 8.05 (d, J = 8.6 Hz, 2H). | (ESI+) 601.1 (MH+) | |
| 10B | 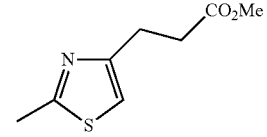 | (CDCl3) δ 1.14-1.21 (m, 2H), 1.43-1.49 (m, 2H), 1.91-2.17 (m, 4H), 2.35-2.49 (m, 1H), 2.54-2.68 (m, 3H), 2.94 (t, J = 7.6 Hz, 2H), 3.65 (s, 3H), 4.71-4.94 (m, 2H), 6.63 (s, 1H), 7.23-7.26 (m, 1H), 7.41-7.45 (m, 2H), 8.01-8.06 (m, 2H), 8.41 (s, 1H). | (ESI+) 525.2 (MH+) | |

TABLE 14-continued

| | | | |
|---|---|---|---|
| 11B | 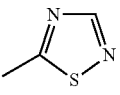 | (DMSO-d6) δ 1.01-1.19 (m, 4H), 1.82-2.26 (m, 4H), 2.42-2.69 (m, 1H), 2.86-2.95 (m, 1H), 4.84-5.10 (m, 2H), 7.06 (d, J = 10.4 Hz, 1H), 7.50 (d, J = 8.6 Hz, 2H), 7.90-7.94 (m, 2H), 8.51 (s, 1H), 13.3 (brs, 1H). | (ESI+) 440.1 (MH+) |
| 12B | 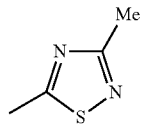 | (CDCl3) δ 1.12-1.22 (m, 2H), 1.41-1.50 (m, 2H), 1.93-2.18 (m, 4H), 2.40-2.51 (m, 1H), 2.51 (s, 3H), 2.53-2.62 (m, 1H), 4.73-4.96 (m, 2H), 7.34 (d, J = 10.4 Hz, 1H), 7.42-7.46 (m, 2H), 8.03-8.07 (m, 2H), 8.72 (brs, 1H). | (ESI+) 454.1 (MH+) |

TABLE 15

| | | | |
|---|---|---|---|
| 13B | 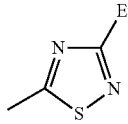 | (CDCl3) δ 1.15-1.22 (m, 2H), 1.31 (t, J =7.9 Hz, 3H), 1.43-1.50 (m, 2H), 1.91-2.19 (m, 4H), 2.39-2.52 (m, 1H), 2.53-2.63 (m, 1H), 2.83 (q, J = 7.9 Hz, 2H), 4.72-4.96 (m, 2H), 7.34 (d, J = 10.4 Hz, 1H), 7.42-7.47 (m, 2H), 8.03-8.08 (m, 2H), 8.73 (brs, 1H). | (ESI+) 468.1 (MH+) |
| 14B | 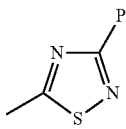 | (CDCl3) δ 1.16-1.22 (m, 2H), 1.46-1.50 (m, 2H), 1.98-2.20 (m, 4H), 2.44-2.54 (m, 1H), 2.57-2.63 (m, 1H), 4.77-4.83 (m, 1H), 4.90-4.93 (m, 1H), 7.36 (d, J = 11.0 Hz, 1H), 7.42-7.45 (m, 3H), 7.48 (d, J = 8.0 Hz, 2H), 8.09 (d, J = 8.0 Hz, 2H), 8.11-8.14 (m, 2H), 8.88 (s, 1H). | (ESI+) 516.2 (MH+) |
| 15B | 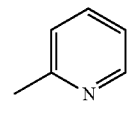 | (CDCl3) δ 1.09-1.18 (m, 2H), 1.40-1.47 (m, 2H), 1.92-2.18 (m, 4H), 2.34-2.48 (m, 1H), 2.51-2.60 (m, 1H), 4.71-4.94 (m, 2H), 7.05 (ddd, J = 8.3, 4.9, 1.2 Hz, 1H), 7.13 (d, J = 10.4 Hz, 1H), 7.43-7.48 (m, 2H), 7.66 (s, 1H), 7.70-7.77 (m, 1H), 7.99-8.04 (m, 2H), 8.21 (dd, J = 4.9, 1.2 Hz, 1H), 8.30 (d, J = 8.6 Hz, 1H). | (ESI+) 433.2 (MH+) |
| 16B | 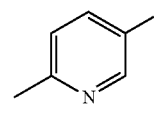 | (CDCl3) δ 1.08-1.21 (m, 2H), 1.37-1.48 (m, 2H), 1.91-2.19 (m, 4H), 2.35-2.49 (m, 1H), 2.47 (s, 3H), 2.50-2.60 (m, 1H), 4.69-4.96 (m, 2H), 7.12 (d, J = 10.4 Hz, 1H), 7.43-7.47 (m, 2H), 7.64 (brs, 1H), 7.66 (dd, J = 8.6, 2.4 Hz, 1H), 7.98-8.04 (m, 2H), 8.13 (d, J = 2.4 Hz, 1H), 8.26 (d, J = 8.6 Hz, 1H). | (ESI+) 479.2 (MH+) |
| 17B | 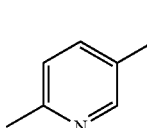 | (CDCl3) δ 0.60-0.73 (m, 2H), 0.93-1.04 (m, 2H), 1.08-1.20 (m, 2H), 1.39-1.47 (m, 2H), 1.79-1.90 (m, 1H), 1.91-2.18 (m, 4H), 2.33-2.47 (m, 1H), 2.50-2.60 (m, 1H), 4.70-4.94 (m, 2H), 7.10 (d, J = 10.4 Hz, 1H), 7.35 (dd, J = 8.6, 2.4 Hz, 1H), 7.42-7.46 (m, 2H), 7.62 (brs, 1H), 7.98-8.03 (m, 3H), 8.18 (d, J = 8.6 Hz, 1H). | (ESI+) 473.2 (MH+) |

TABLE 16

| | | | |
|---|---|---|---|
| 18B | 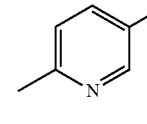 | (DMSO-d6) δ 1.03-1.16 (m, 4H), 1.87-2.01 (m, 2H), 2.08-2.22 (m, 2H), 2.50-2.57 (m, 1H), 2.86-2.93 (m, 1H), 4.47 (d, J = 5.5 Hz, 2H), 4.85-5.05 (m, 2H), 5.24 (t, J = 5.8 Hz, 1H), 6.67 (d, J = 10.4 Hz, 1H), 7.49 (d, J = 8.6 Hz, 2H), 7.71 (dd, J = 8.6, 2.4 Hz, 1H), 7.91 (d, J = 8.6 Hz, 2H), 8.00 (d, J = 8.6 Hz, 1H), 8.27 (d, J = 1.8 Hz, 1H), 10.5 (s, 1H). | (ESI+) 463.2 (MH+) |
| 19B | 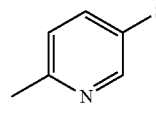 | (CDCl3) δ 1.12-1.18 (m, 2H), 1.43-1.47 (m, 2H), 1.96-2.17 (m, 4H), 2.41-2.50 (m, 1H), 2.53-2.59 (m, 1H), 2.73 (s, 6H), 4.75-4.96 (m, 2H), 7.17 (d, J = 10.4 Hz, 1H), 7.46 (d, J = 8.6 Hz, 2H), 7.90 (s, 1H), 8.04 (d, J = 8.6 Hz, 2H), 8.08 (dd, J = 8.6, 2.4 Hz, 1H), 8.48 (d, J = 9.2 Hz, 1H), 8.59 (d, J = 2.4 Hz, 1H). | (ESI+) 540.1 (MH+) |
| 20B | 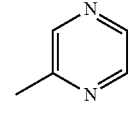 | (CDCl3) δ 1.11-1.18 (m, 2H), 1.42-1.47 (m, 2H), 1.93-2.20 (m, 4H), 2.37-2.60 (m, 2H), 4.73-4.95 (m, 2H), 7.18 (d, J = 10.4 Hz, 1H), 7.45-7.49 (m, 2H), 7.60 (s, 1H), 8.02-8.06 (m, 2H), 8.18-8.20 (m, 1H), 8.37 (d, J = 2.4 Hz, 1H), 9.63 (d, J = 1.8 Hz, 1H). | (ESI+) 434.2 (MH+) |

TABLE 16-continued

| | | | |
|---|---|---|---|
| 21B | 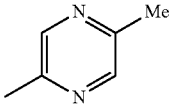 | (CDCl3) δ 1.14 (ddd, J = 14.1, 6.1, 2.3 Hz, 2H), 1.45 (dd, J = 11.0, 6.1, 1.8 Hz, 2H), 1.94-2.18 (m, 4H), 2.39-2.50 (m, 1H), 2.53 (s, 3H), 2.52-2.59 (m, 1H), 4.74-4.94 (m, 2H), 7.16 (d, J = 10.4 Hz, 1H), 7.46 (d, J = 8.0 Hz, 2H), 7.52 (brs, 1H), 8.03 (d, J = 8.6 Hz, 2H), 8.05 (s, 1H), 9.50 (d, J = 1.2 Hz, 1H). | (ESI+) 448.2 (MH+) |
| 22B | 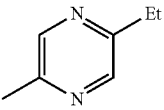 | (CDCl3) δ 1.10-1.18 (m, 2H), 1.31 (t, J = 7.9 Hz, 3H), 1.41-1.47 (m, 2H), 1.91-2.19 (m, 4H), 2.37-2.50 (m, 1H), 2.51-2.60 (m, 1H), 2.82 (q, J = 7.9 Hz, 2H), 4.71-4.95 (m, 2H), 7.16 (d, J = 10.4 Hz, 1H), 7.44-7.48 (m, 2H), 7.54 (brs, 1H), 8.00-8.07 (m, 3H), 9.52 (d, J = 1.8 Hz, 1H). | (ESI+) 462.2 (MH+) |

TABLE 17

| | | | |
|---|---|---|---|
| 23B | 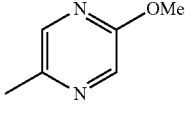 | (CDCl3) δ 1.11-1.17 (m, 2H), 1.42-1.46 (m, 2H), 1.94-2.17 (m, 4H), 2.37-2.48 (m, 1H), 2.52-2.59 (m, 1H), 3.97 (s, 3H), 4.73-4.93 (m, 2H), 7.15 (d, J = 10.4 Hz, 1H), 7.47-7.44 (m, 3H), 7.85 (d, J = 1.2 Hz, 1H), 8.02 (d, J = 8.6 Hz, 2H), 9.12 (d, J = 1.2 Hz, 1H). | (ESI+) 464.2 (MH+) |
| 24B | 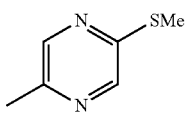 | (CDCl3) δ 1.10-1.17 (m, 2H), 1.41-1.48 (m, 2H), 1.91-2.19 (m, 4H), 2.36-2.49 (m, 1H), 2.51-2.65 (m, 4H), 4.71-4.95 (m, 2H), 7.16 (d, J = 10.3 Hz, 1H), 7.43-7.49 (m, 3H), 8.01-8.09 (m, 3H), 9.44 (d, J = 1.2 Hz, 1H). | (ESI+) 480.1 (MH+) |
| 25B | 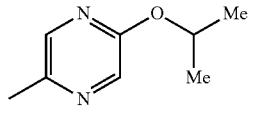 | (CDCl3) δ 1.11-1.18 (m, 2H), 1.35 (d, J = 6.1 Hz, 6H), 1.41-1.48 (m, 2H), 1.91-2.18 (m, 4H), 2.35-2.48 (m, 1H), 2.51-2.60 (m, 1H), 4.71-4.94 (m, 2H), 5.26 (seq, J = 6.1 Hz, 1H), 7.15 (d, J = 10.4, Hz, 1H), 7.40 (s, 1H), 7.43 (m, 2H), 7.77 (d, J = 1.2 Hz, 1H), 7.99-8.04 (m, 2H), 9.09 (d, J = 1.2 Hz, 1H). | (ESI+) 492.2 (MH+) |
| 26B | 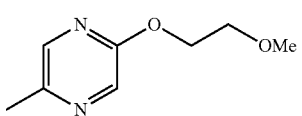 | (CDCl3) δ 1.14 (ddd, J = 14.1, 6.1, 1.2 Hz, 2H), 1.44 (ddd, J = 9.8, 6.7, 1.8 Hz, 2H), 1.94-2.18 (m, 4H), 2.36-2.47 (m, 1H), 2.52-2.59 (m, 1H), 3.43 (s, 3H), 3.73-3.77 (m, 2H), 4.47-4.51 (m, 2H), 4.72-4.91 (m, 2H), 7.15 (d, J = 10.4 Hz, 1H), 7.44 (brs, 1H), 7.46 (dt, J = 1.8 Hz, 2H), 7.91 (d, J = 1.2 Hz, 1H), 8.02 (dt, J = 8.6 Hz, 1.8 Hz, 2H), 9.09 (d, J = 1.2 Hz, 1H). | (ESI+) 508.2 (MH+) |
| 27B | 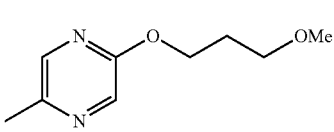 | (CDCl3) δ 1.08-1.18 (m, 2H), 1.37-1.48 (m, 2H), 1.92-2.18 (m, 6H), 2.35-2.48 (m, 1H), 2.50-2.60 (m, 1H), 3.35 (s, 3H), 3.53 (t, J = 6.7 Hz, 2H), 4.41 (t, J = 6.7 Hz, 2H), 4.72-4.94 (m, 2H), 7.15 (d, J = 10.4 Hz, 1H), 7.43 (brs, 1H), 7.44-7.48 (m, 2H), 7.83 (d, J = 1.8 Hz, 1H), 8.00-8.04 (m, 2H), 9.10 (d, J = 1.2 Hz, 1H). | (ESI+) 522.2 (MH+) |

TABLE 18

| | | | |
|---|---|---|---|
| 28B | 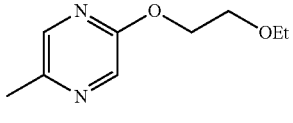 | (CDCl3) δ 1.11-1.17 (m, 2H), 1.24 (t, J = 7.3 Hz, 3H), 1.41-1.47 (m, 2H), 1.91-2.19 (m, 4H), 2.34-2.48 (m, 1H), 2.50-2.60 (m, 1H), 3.58 (q, J = 7.3 Hz, 2H), 3.76-3.81 (m, 2H), 4.44-4.51 (m, 2H), 4.72-4.94 (m, 2H), 7.15 (d, J = 10.4 Hz, 1H), 7.41-7.48 (m, 3H), 7.90 (d, J = 1.8 Hz, 1H), 8.00-8.05 (m, 2H), 9.09 (d, J = 1.2 Hz, 1H). | (ESI+) 522.2 (MH+) |
| 29B | 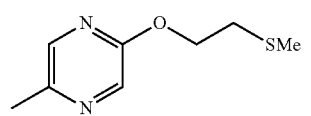 | (CDCl3) δ 1.12-1.17 (m, 2H), 1.42-1.46 (m, 2H), 1.94-2.17 (m, 4H), 2.20 (s, 3H), 2.37-2.48 (m, 1H), 2.52-2.59 (m, 1H), 2.88 (t, J = 7.0 Hz, 2H), 4.51 (t, J = 6.7 Hz, 2H), 4.72-4.93 (m, 2H), 7.15 (d, J = 10.4 Hz, 1H), 7.47-7.45 (m, 3H), 7.86 (d, J = 1.2 Hz, 1H), 8.02 (d, J = 8.6 Hz, 2H), 9.10 (d, J = 1.2 Hz, 1H). | (ESI+) 524.1 (MH+) |

TABLE 18-continued

| No. | Structure | NMR | MS |
|---|---|---|---|
| 30B | (pyrazine-O-CH2CH2-O-tetrahydropyran with 5-methyl) | (CDCl3) δ 1.09-1.18 (m, 2H), 1.37-1.48 (m, 2H), 1.48-1.67 (m, 4H), 1.68-1.89 (m, 2H), 1.91-2.21 (m, 4H), 2.35-2.48 (m, 1H), 2.51-2.59 (m, 1H), 3.46-3.56 (m, 1H), 3.75-3.94 (m, 2H), 4.02-4.10 (m, 1H), 4.45-4.56 (m, 2H), 4.68 (t, J = 3.3 Hz, 1H), 4.71-4.95 (m, 2H), 7.15 (d, J = 10.4 Hz, 1H), 7.14-7.48 (m, 3H), 7.89 (d, J = 1.2 Hz, 1H), 8.02 (d, J = 8.6 Hz, 2H), 9.09 (d, J = 1.2 Hz, 1H). | (ESI+) 578.2 (MH+) |
| 31B | (pyrazine-O-CH2CH2-OH with 5-methyl) | (CDCl3) δ 1.09-1.18 (m, 2H), 1.40-1.48 (m, 2H), 1.92-12.19 (m, 4H), 2.32 (t, J = 6.1 Hz, 1H), 2.36-2.50 (m, 1H), 2.51-2.60 (m, 1H), 3.94-4.02 (m, 2H), 4.44-4.51 (m, 2H), 4.71-4.95 (m, 2H), 7.15 (d, J = 10.4 Hz, 1H), 7.41-7.50 (m, 3H), 7.91 (d, J = 1.2 Hz, 1H), 8.03 (d, J = 8.8 Hz, 2H), 9.10 (d, J = 1.8 Hz, 1H). | (ESI+) 494.2 (MH+) |

TABLE 19

| No. | Structure | NMR | MS | |
|---|---|---|---|---|
| 32B | (pyrazine-(R)-dioxolane-dimethyl with 5-methyl) | (DMSO-d6) δ 1.03-1.10 (m, 3H), 1.12-1.16 (m, 2H), 1.40 (s, 3H), 1.44 (s, 3H), 1.86-2.01 (m, 2H), 2.10-2.23 (m, 2H), 2.52-2.59 (m, 1H), 2.87-2.93 (m, 1H), 3.95 (dd, J = 7.9, 6.7 Hz, 1H), 4.35 (dd, J = 7.9, 6.7 Hz, 1H), 4.86-5.05 (m, 2H), 5.18 (t, J = 6.7 Hz, 1H), 6.76 (d, J = 10.4 Hz, 1H), 7.49 (d, J = 8.6 Hz, 2H), 7.91 (d, J = 8.6 Hz, 2H), 8.49 (d, J = 1.2 Hz, 1H), 9.22 (d, J = 1.2 Hz, 1H), 11.0 (s, 1H). | (ESI+) 534.2 (MH+) | (−) |
| 33B | (pyrazine-(S)-dioxolane-dimethyl with 5-methyl) | (DMSO-d6) δ 1.03-1.16 (m, 5H), 1.40 (s, 3H), 1.44 (s, 3H), 1.86-2.01 (m, 2H), 2.10-2.22 (m, 2H), 2.53-2.60 (m, 1H), 2.87-2.93 (m, 1H), 3.95 (dd, J = 7.9, 6.7 Hz, 1H), 4.35 (dd, J = 7.9, 6.7 Hz, 1H), 4.85-5.06 (m, 2H), 5.18 (t, J = 6.4 Hz, 1H), 6.76 (d, J = 10.4 Hz, 1H), 7.49 (d, J = 8.6 Hz, 2H), 7.91 (d, J = 8.6 Hz, 2H), 8.49 (d, J = 1.8 Hz, 1H), 9.22 (d, J = 1.8 Hz, 1H), 11.0 (s, 1H). | (ESI+) 534.2 (MH+) | (+) |
| 34B | (pyrazine-(S)-CH(OH)CH2OH with 5-methyl) | (DMSO-d6) δ 1.03-1.16 (m, 4H), 1.89-2.01 (m, 2H), 2.09-2.20 (m, 2H), 2.52-2.60 (m, 1H), 2.87-2.93 (m, 1H), 3.53-3.59 (m, 1H), 3.65-3.71 (m, 1H), 4.63 (q, J = 5.1 Hz, 1H), 4.72 (t, J = 5.8 Hz, 1H), 4.86-5.06 (m, 2H), 5.54 (d, J = 4.9 Hz, 1H), 6.75 (d, J = 10.4 Hz, 1H), 7.49 (d, J = 8.6 Hz, 2H), 7.91 (d, J = 8.6 Hz, 2H), 8.46 (d, J = 1.2 Hz, 1H), 9.17 (d, J = 1.8 Hz, 1H), 10.9 (s, 1H). | (ESI+) 494.2 (MH+) | (−) |
| 35B | (pyrazine-(S)-CH(OH)CH2OH with 5-methyl) | (DMSO-d6) δ 1.03-1.16 (m, 4H), 1.85-2.01 (m, 2H), 2.10-2.23 (m, 2H), 2.53-2.60 (m, 1H), 2.86-2.93 (m, 1H), 3.53-3.59 (m, 1H), 3.65-3.71 (m, 1H), 4.63 (q, J = 5.1 Hz, 1H), 4.72 (t, J = 5.8 Hz, 1H), 4.85-5.07 (m, 2H), 5.53 (d, J = 4.9 Hz, 1H), 6.75 (d, J = 10.4 Hz, 1H), 7.49 (d, J = 8.6 Hz, 2H), 7.91 (d, J = 8.6 Hz, 2H), 8.46 (d, J = 1.2 Hz, 1H), 9.17 (d, J = 1.8 Hz, 1H), 10.9 (s, 1H). | (ESI+) 494.2 (MH+) | (+) |

TABLE 20

| No. | Structure | NMR | MS |
|---|---|---|---|
| 36B | (pyrazine-P(=O)(OEt)2 with 5-methyl) | (CDCl3) δ 1.11-1.19 (m, 2H), 1.36 (t, J = 7.3 Hz, 6H), 1.42-1.48 (m, 2H), 1.90-2.21 (m, 4H), 2.37-2.62 (m, 2H), 4.13-4.34 (m, 4H), 4.73-4.97 (m, 2H), 7.21 (d, J = 10.4 Hz, 1H), 7.46 (d, J = 8.6 Hz, 2H), 7.77 (brs, 1H), 8.05 (d, J = 8.6 Hz, 2H), 8.72 (s, 1H), 9.78 (s, 1H). | (ESI+) 570.2 (MH+) |
| 37B | (pyrazine-CH2-P(=O)(OEt)2 with 5-methyl) | (CDCl3) δ 1.10-1.18 (m, 2H), 1.29 (t, J = 7.3 Hz, 6H), 1.41-1.48 (m, 2H), 1.92-2.20 (m, 4H), 2.37-2.61 (m, 2H), 3.36 (s, 1H), 3.42 (s, 1H), 4.04-4.16 (m, 4H), 4.71-4.96 (m, 2H), 7.17 (d, J = 10.4 Hz, 1H), 7.46 (d, J = 7.9 Hz, 2H), 7.60 (brs, 1H), 8.03 (d, J = 8.6 Hz, 2H), 8.23 (d, J = 1.8 Hz, 1H), 9.35 (s, 1H). | (ESI+) 584.2 (MH+) |

TABLE 20-continued

| | | | |
|---|---|---|---|
| 38B | 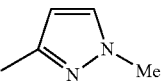 | (CDCl3) δ 1.15 (ddd, J = 13.4, 5.5, 1.2 Hz, 2H), 1.44 (ddd, J = 11.4, 5.5, 1.2 Hz, 2H), 1.91-2.14 (m, 4H), 2.31-2.42 (m, 1H), 2.52-2.59 (m, 1H), 3.76 (s, 3H), 4.70-4.91 (m, 2H), 6.77 (d, J = 2.5 Hz, 1H), 7.13 (d, J = 10.4 Hz, 1H), 7.26 (d, J = 2.4 Hz, 1H), 7.43 (d, J = 8.6 Hz, 2H), 7.47 (brs, 1H), 7.99 (d, J = 8.0 Hz, 2H). | (ESI+) 436.2 (MH+) |
| 39B | 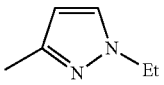 | (CDCl3) δ 1.12-1.18 (m, 2H), 1.39-1.46 (m, 5H), 1.91-2.14 (m, 4H), 2.32-2.43 (m, 1H), 2.53-2.59 (m, 1H), 4.01 (q, J = 7.1 Hz, 2H), 4.70-4.92 (m, 2H), 6.77 (d, J = 1.8 Hz, 1H), 7.12 (d, J = 10.4 Hz, 1H), 7.30 (d, J = 1.8 Hz, 1H), 7.43 (d, J = 8.6 Hz, 1H), 7.51 (s, 1H), 7.99 (d, J = 8.6 Hz, 2H). | (ESI+) 450.2 (MH+) |
| 40B | 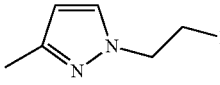 | (CDCl3) δ 1.12-1.17 (m, 2H), 1.42-1.46 (m, 2H), 1.92-2.14 (m, 4H), 2.33-2.44 (m, 1H), 2.52-2.59 (m, 1H), 4.25 (dt, J = 26.5, 4.7 Hz, 2H), 4.67 (dt, J = 47.1, 4.9 Hz, 2H), 4.71-4.92 (m, 2H), 6.82 (d, J = 2.4 Hz, 1H), 7.12 (d, J = 10.4 Hz, 1H), 7.37 (d, J = 2.4 Hz, 1H), 7.44 (d, J = 8.6 Hz, 1H), 7.49 (s, 1H), 8.00 (d, J = 8.6 Hz, 2H). | (ESI+) 468.2 (MH+) |

TABLE 21

| | | | | |
|---|---|---|---|---|
| 41B | 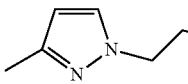 | (DMSO-d6) δ 1.01-1.17 (m, 4H), 1.81-1.97 (m, 2H), 2.07-2.21 (m, 2H), 2.48-2.57 (m, 1H), 2.85-2.91 (m, 1H), 3.70 (q, J = 5.5 Hz, 2H), 4.03 (t, J = 5.5 Hz, 2H), 4.84-5.05 (m, 3H), 6.44 (d, J = 2.4 Hz, 1H), 6.57 (d, J = 10.4 Hz, 1H), 7.44 (d, J = 8.6 Hz, 2H), 7.56 (d, J = 2.4 Hz, 1H), 7.89 (d, J = 8.6 Hz, 2H), 10.6 (s, 1H). | (ESI+) 466.2 (MH+) | |
| 42B | 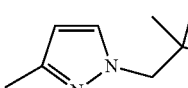 | (CDCl3) δ 1.09-1.17 (m, 8H), 1.41-1.46 (m, 2H), 1.92-2.15 (m, 4H), 2.33-2.44 (m, 1H), 2.53-2.60 (m, 1H), 3.27 (s, 1H), 3.91 (s, 2H), 4.72-4.92 (m, 2H), 6.83 (d, J = 2.4 Hz, 1H), 7.12 (d, J = 10.4 Hz, 1H), 7.33 (d, J = 2.4 Hz, 1H), 7.44 (d, J = 7.9 Hz, 1H), 7.51 (s, 1H), 8.01 (d, J = 7.9 Hz, 2H). | (ESI+) 494.2 (MH+) | |
| 43B | 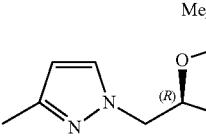 | (CDCl3) δ 1.12-1.17 (m, 2H), 1.32 (s, 3H), 1.37 (s, 3H), 1.42-1.47 (m, 2H), 1.91-2.13 (m, 4H), 2.32-2.41 (m, 1H), 2.52-2.59 (m, 1H), 3.68 (dd, J = 8.9, 6.4 Hz, 1H), 4.01 (dd, J = 8.6, 6.4 Hz, 1H), 4.06-4.08 (m, 2H), 4.33-4.39 (m, 1H), 4.72-4.92 (m, 2H), 6.80 (d, J = 2.4 Hz, 1H), 7.11 (d, J = 11.0 Hz, 1H), 7.37 (d, J = 2.4 Hz, 1H), 7.43 (d, J = 8.6 Hz, 1H), 7.47 (s, 1H), 8.00 (d, J = 7.9 Hz, 2H). | (ESI+) 536.2 (MH+) | (+) |
| 44B | 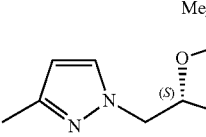 | (CDCl3) δ 1.12-1.17 (m, 2H), 1.32 (s, 3H), 1.36 (s, 3H), 1.42-1.47 (m, 2H), 1.91-2.15 (m, 4H), 2.33-2.43 (m, 1H), 2.52-2.59 (m, 1H), 3.68 (dd, J = 8.6, 6.1 Hz, 1H), 4.01 (dd, J = 8.6, 6.1 Hz, 1H), 4.06-4.08 (m, 2H), 4.33-4.39 (m, 1H), 4.72-4.91 (m, 2H), 6.80 (d, J = 2.4 Hz, 1H), 7.11 (d, J = 10.4 Hz, 1H), 7.37 (d, J = 2.4 Hz, 1H), 7.43 (d, J = 8.6 Hz, 1H), 7.47 (s, 1H), 8.00 (d, J = 7.9 Hz, 2H). | (ESI+) 536.2 (MH+) | (−) |

TABLE 22

| | | | | |
|---|---|---|---|---|
| 45B | 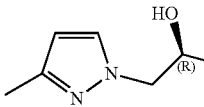 | (DMS0-d6) δ 1.03-1.16 (m, 4H), 1.81-1.98 (m, 2H), 2.06-2.21 (m, 2H), 2.51-2.55 (m, 1H), (2.85-2.91 (m, 1H), 3.25-3.35 (m, 2H), 3.73-3.80 (m, 1H), 3.87 (dd, J = 13.4, 7.9 Hz 1H), 4.09 (dd, J = 13.8, 4.0 Hz 1H), 4.69 (t, J = 5.5 Hz, 1H), 4.85-5.05 (m, 3H), 6.44 (d, J = 1.8 Hz, 1H), 6.58 (d, J = 10.4 Hz, 1H), 7.44 (d, J = 8.6 Hz, 2H), 7.53 (d, J = 2.4 Hz, 1H), 7.89 (d, J = 8.6 Hz, 2H), 10.6 (s, 1H). | (ESI+) 496.2 (MH+) | (+) |
| 46B | 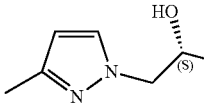 | (DMS0-d6) δ 1.03-1.16 (m, 4H), 1.81-1.98 (m, 2H), 2.08-2.23 (m, 2H), 2.48-2.56 (m, 1H), 2.85-2.92 (m, 1H), 3.24-3.35 (m, 2H), 3.73-3.81 (m, 1H), 3.87 (dd, J = 13.4, 7.9 Hz 1H), 4.09 (dd, J = 13.8, 4.0 Hz 1H), 4.69 (t, J = 5.8 Hz, 1H), 4.85-5.05 (m, 3H), 6.44 (d, J = 2.4 Hz, 1H), 6.58 (d, J = 10.41 Hz, 1H), 7.44 (d, J = 8.6 Hz, 2H), 7.53 (d, J = 2.4 Hz, 1H), 7.89 (d, J = 8.6 Hz, 2H), 10.6 (s, 1H). | (ESI+) 496.2 (MH+) | (−) |

TABLE 22-continued

| | | | |
|---|---|---|---|
| 47B | 3-methylisoxazole | (CDCl3) δ 1.13-1.19 (m, 2H), 1.42-1.47 (m, 2H), 1.91-2.15 (m, 4H), 2.36-2.47 (m, 1H), 2.53-2.60 (m, 1H), 4.73-4.94 (m, 2H), 7.14 (d, J = 1.8 Hz, 1H), 7.18 (d, J = 10.4 Hz, 1H), 7.43 (d, J = 8.6 Hz, 2H), 7.80 (s, 1H), 8.02 (d, J = 7.6 Hz, 1H), 8.31 (d, J = 1.8 Hz, 2H). | (ESI+) 423.1 (MH+) |
| 48B | 2-methylbenzothiazole | (CDCl3) δ 1.17-1.22 (m, 2H), 1.45-1.50 (m, 2H), 1.95-2.17 (m, 4H), 2.39-2.50 (m, 1H), 4.74-4.95 (m, 2H), 7.32-7.36 (m, 2H), 7.43 (dd, J = 7.9 Hz, 1.2 Hz, 1H), 7.47 (d, J = 8.6 Hz, 2H), 7.69 (d, J = 8.6 Hz, 1H), 7.85 (d, J = 7.9 Hz, 1H), 8.06 (d, J = 8.6 Hz, 2H), 8.60 (s, 1H). | (ESI+) 489.1 (MH+) |
| 49B | 6-methoxy-2-methylbenzothiazole | (CDCl3) δ 1.16-1.22 (m, 2H), 1.45-1.49 (m, 2H), 1.95-2.17 (m, 4H), 2.38-2.49 (m, 1H), 2.56-2.62 (m, 1H), 3.87 (s, 3H), 4.74-4.94 (m, 2H), 7.03 (dd, J = 9.2, 2.4 Hz, 1H), 7.33-7.30 (m, 2H), 7.46 (d, J = 7.9 Hz, 2H), 7.57 (d, J = 8.6 Hz, 1H), 8.05 (d, J = 7.9 Hz, 2H), 8.53 (s, 1H). | (ESI+) 519.1 (MH+) |

TABLE 23

| | | | |
|---|---|---|---|
| 50B | 6-(difluoromethoxy)-2-methylbenzothiazole | (CDCl3) δ 1.16-1.22 (m, 2H), 1.45-1.50 (m, 2H), 1.95-2.17 (m, 4H), 2.40-2.50 (m, 1H), 2.56-2.63 (m, 1H), 3.87 (s, 3H), 4.74-4.94 (m, 2H) 6.54 (t, J = 73.7 Hz, 1H), 7.23 (dd, J = 8.6, 2.4 Hz, 1H), 7.34 (d, J = 10.4 Hz, 1H), 7.47 (d, J = 8.6 Hz, 2H), 7.62 (d, J = 2.4 Hz, 1H), 7.65 (d, J = 9.2 Hz, 1H), 8.06 (d, J = 8.6 Hz, 2H), 8.56 (s, 1H). | (ESI+) 555.1 (MH+) |
| 51B | 6-fluoro-2-methylbenzothiazole | (CDCl3) δ 1.16-1.22 (m, 2H), 1.45-1.50 (m, 2H), 1.97-2.13 (m, 4H), 2.39-2.50 (m, 1H), 2.56-2.62 (m, 1H), 4.75-4.95 (m, 2H), 7.16 (td, J = 9.0, 2.6 Hz, 1H), 7.33 (d, J = 10.4 Hz, 1H), 7.47 (d, J = 7.9 Hz, 2H), 7.53 (dd, J = 7.9, 2.4 Hz, 1H), 7.62 (dd, J = 9.2, 4.3 Hz, 1H), 8.06 (d, J = 8.6 Hz, 2H), 8.56 (s, 1H). | (ESI+) 507.1 (MH+) |
| 52B | isopropyl 2-methylbenzothiazole-6-carboxylate | (CDCl3) δ 1.17-1.22 (m, 2H), 1.40 (d, J = 6.1 Hz, 6H), 1.45-1.50 (m, 2H), 1.96-2.20 (m, 4H), 2.40-2.51 (m, 1H), 2.56-2.60 (m, 1H), 4.76-4.81 (m, 1H), 4.89-4.95 (m, 1H), 5.28 (sep, J = 6.1 Hz, 1H), 7.36 (d, J = 11.0 Hz, 1H), 7.48 (d, J = 8.0 Hz, 2H), 7.70 (d, J = 8.6 Hz, 1H), 8.07 (d, J = 8.0 Hz, 2H), 8.12 (dd, J = 8.3, 1.5 Hz, 1H), 8.56 (d, J = 1.5 Hz, 1H), 8.62 (s, 1H). | (ESI+) 575.2 (MH+) |
| 53B | 2-methylthiazolo[5,4-b]pyridine | (CDCl3) δ 1.14-1.22 (m, 2H), 1.44-1.50 (m, 2H), 1.94-2.20 (m, 4H), 2.39-2.53 (m, 1H), 2.55-2.63 (m, 1H), 4.73-4.96 (m, 2H), 7.32-7.40 (m, 2H) 7.45-7.50 (m, 2H), 7.92 (d, J = 7.9, 1.5 Hz, 1H) 8.04-8.08 (m, 2H), 8.46-8.54 (m, 2H). | (ESI+) 490.1 (MH+) |
| 54B | 6-butoxy-2-methylthiazolo[5,4-b]pyridine | (CD3OD) δ 0.99 (t, J = 7.3 Hz, 3H), 1.03-1.17 (m, 2H), 1 20-1.33 (m, 2H), 1 42-1.57 (m, 2H), 1.69-1.84 (m, 2H), 1.89-2.07 (m, 2H), 2.12-2.28 (m, 2H), 2.61-2.77 (m, 2H), 4.33 (t, J = 6.7 Hz, 2H), 4.77-4.97 (m, 2H), 6.82 (d, J = 8.6 Hz, 1H), 6.92 (d, J = 10.4 Hz, 1H), 7.51-7.58 (m, 2H), 7.92 (d, J = 8.6 Hz, 1H), 7.92-8.02 (m, 2H). | (ESI+) 562.2 (MH+) |

TABLE 24

| | | | |
|---|---|---|---|
| 55B | 6-(2-methoxyethoxy)-2-methylthiazolo[5,4-b]pyridine | (CDCl3) δ 1.15-1.22 (m, 2H), 1.43-1.50 (m, 2H), 1.92-2.19 (m, 4H), 2.37-2.50 (m, 1H), 2.54-2.63 (m, 1H), 3.45 (s, 3H), 3.76-3.80 (m, 2H), 4.52-4.58 (m, 2H), 4.73-4.95 (m, 2H), 6.88 (d, J = 9.2 Hz, 1H), 7.32 (d, J = 10.4 Hz, 1H), 7.44-7.49 (m, 2H), 7.79 (d, J = 9.2 Hz, 1H), 8.03-8.08 (m, 2H), 8.39 (brs, 1H). | (ESI+) 564.2 (MH+) |

TABLE 24-continued

| 56B | [structure: 2-methyl-thiazolo[5,4-b]pyridine with -O-CH2-CO2Et substituent] | (CDCl3) δ 1.15-1.22 (m, 2H), 1.30 (t, J = 7.3 Hz, 3H), 1.44-1.50 (m, 2H), 1.92-2.19 (m, 4H) 2.36-2.50 (m, 1H), 2.55-2.63 (m, 1H), 4.26 (q, J = 7.3 Hz, 2H), 4.73-4.98 (m, 4H), 6.95 (d, J = 8.6 Hz, 1H), 7.32 (d, J = 10.4 Hz, 1H), 7.45-7.49 (m, 2H), 7.84 (d, J = 8.6 Hz, 1H), 8.03-8.08 (m, 2H), 8.39 (brs, 1H). | (ESI+) 592.1 (MH+) | |

TABLE 25

| Compound No. | Structure (A) | 1H NMR (400 MHz) | MS (m/z) | Optical rotation |
|---|---|---|---|---|
| 57B | [structure: 2-methylthiazole with CH(OH)-CH2OH side chain, * chiral] | (DMSO-d6) δ 1.04-1.09 (m, 2H), 1.13-1.18 (m, 2H), 1.84-2.00 (m, 2H), 2.09-2.24 (m, 2H), 2.50-2.60 (m, 1H), 2.88-2.93 (m, 1H), 13.42-3.51 (m, 1H), 3.62-3.71 (m, 1H), 4.54-4.58 (m, 1H), 4.65 (t, J = 5.8 Hz, 1H), 4.86-4.94 (m, 1H), 4.98-5.07 (m, 1H), 5.26 (d, J = 4.9 Hz, 1H), 6.81 (d, J = 10.4 Hz, 1H), 6.95 (s, 1H), 7.46 (d, J = 8.6 Hz, 2H), 7.90 (d, J = 8.6 Hz, 2H). | (ESI+) 499.1 (MH+) | (+) |
| 58B | [structure: 2-methylthiazole with CH(OH)-CH2OH side chain, * chiral] | (DMSO-d6) δ 1.04-1.09 (m, 2H), 1.13-1.18 (m, 2H), 1.84-2.00 (m, 2H), 2.09-2.24 (m, 2H), 2.50-2.60 (m, 1H), 2.88-2.93 (m, 1H), 3.42-3.51 (m, 1H), 3.62-3.71 (m, 1H), 4.54-4.58 (m, 1 H), 4.65 (t, J = 5.8 Hz, 1H), 4.86-4.94 (m, 1H), 4.98-5.07 (m, 1 H), 5.26 (d, J = 4.9 Hz, 1H), 6.81 (d, J = 10.4 Hz, 1H), 6.95 (s, 1H), 7.46 (d, J = 8.6 Hz, 2H), 7.90 (d, J = 8.6 Hz, 2H). | (ESI+) 499.1 (MH+) | (−) |
| 59B | [structure: 2-methylthiazole with 2,2-dimethyl-1,3-dioxane substituent] | (CDCl3) δ 1.13-1.19 (m, 2H), 1.45 (s, 3H), 1.45-1.47 (m, 2H), 1.47 (s, 3H), 1.93-2.17 (m, 4H), 2.38-2.50 (m, 1H), 2.54-2.61 (m, 1H), 3.04-3.12 (m, 1H), 4.02 (dd, J = 22.0, 10.4 Hz, 2H), 4.04 (dd, J = 22.0, 10.4 Hz, 2H), 4.73-4.83 (m, 1H), 4.86-4.95 (m, 1H), 6.79 (s, 1H), 7.24 (d, J = 10.4 Hz, 1 H), 7.44 (d, J = 7.9 Hz, 2H), 8.05 (d, J = 7.9 Hz, 2H), 8.40 (s, 1H). | (ESI+) 553.2 (MH+) | |

TABLE 26

| 60B | [structure: 2-methylthiazole with CH(CH2OH)2 substituent] | (CDCl3) δ 1.12-1.19 (m, 2H), 1.42-1.48 (m, 2H), 1.94-2.18 (m, 4H), 2.39-2.52 (m, 1H), 2.54-2.62 (m, 1H), 3.02-3.10 (m, 1H), 3.94 (s, 2H), 3.95 (s, 2H), 4.74-4.82 (m, 1H), 4.87-4.96 (m, 1H), 6.79 (s, 1H), 7.24 (d, J = 10.4 Hz, 1 H), 7.45 (d, J = 7.9 Hz, 2H), 8.05 (d, J = 8.6 Hz, 2H), 8.52 (s, 1H). | (ESI+) 513.1 (MH+) | |
| 61B | [structure: 2-methylthiazole with -CH2CH2-OTHP substituent] | (CDCl3) δ 1.15-1.20 (m, 2H), 1.44-1.81 (m, 10H), 1.96-2.17 (m, 4H), 2.36-2.48 (m, 1H), 2.55-2.61 (m, 1H), 2.91 (t, J = 6.7 Hz, 2H), 3.43-3.48 (1H, m), 3.62-3.68 (m, 1H), 3.73-3.79 (m, 1H), 3.94-4.00 (1H, m), 4.57 (t, J = 3.7 Hz, 1H), 4.73-4.94 (m, 2H), 6.71 (s, 1H), 7.25 (d, J = 9.2 Hz, 1H), 7.44 (d, J = 8.6 Hz, 2H), 8.03 (d, J = 8.6 Hz, 2H), 8.51 (1H, S). | (ESI+) 567.2 (MH+) | |
| 62B | [structure: 2-methylthiazole with -CH2CH2-OH substituent] | (DMSO-d6) δ 1.04-1.10 (m, 2H), 1.12-1.16 (m, 2H), 1.90-1.98 (m, 2H), 2.53-2.62 (m, 1H), 2.75 (t, J = 6.7 Hz, 2H), 2.86-2.93 (1H, m), 3.67 (q, J = 6.5 Hz, 2H), 4.62 (t, J = 5.1 Hz, 1H), 4.85-5.08 (m, 2H), 6.83-6.79 (m, 2H), 7.46 (d, J = 8.5 Hz. 1H), 7.90 (d, J = 8.5 Hz, 2H), 12.4 (s, 1H). | (ESI+) 483.1 (MH+) | |

TABLE 26-continued

| | Structure | NMR | MS |
|---|---|---|---|
| 63B | 2-methylthiazole-4-S(O)₂NMe₂ | (CDCl3) δ 1.15-1.20 (m, 2H), 1.44-1.48 (m, 2H), 1.94-2.17 (m, 4H), 2.41-2.50 (m, 1H), 2.54-2.61 (m, 1H), 2.79 (s, 6H), 4.75-4.96 (m, 2H), 7.31 (d, J = 10.4 Hz, 1H), 7.44 (d, J = 8.6 Hz, 2H), 7.84 (s, 1H), 8.06 (d, J = 8.6 Hz, 2H), 8.69 (s, 1H). | (ESI+) 546.1 (MH+) |
| 64B | 2-methylthiazol-4-yl-P(O)(OEt)₂ | (CDCl3) δ 1.17-1.26 (m, 2H), 1.31 (t, J = 6.7 Hz, 6H), 1.44-1.51 (m, 2H), 1.89-2.17 (m, 4H), 2.33-2.48 (m, 1H), 2.57-2.68 (m, 1H), 4.04-4.24 (m, 4H), 4.71-4.96 (m, 2H), 7.32 (d, J = 10.4 Hz, 1H), 7.40-7.45 (m, 2H), 7.76 (d, J = 4.9 Hz, 1H), 8.03-8.08 (m, 2H), 8.57 (brs, 1H). | (ESI+) 575.1 (MH+) |

TABLE 27

| | Structure | NMR | MS |
|---|---|---|---|
| 65B | 2-methylthiazol-5-yl-P(O)(OEt)₂ | (CDCl3) δ 1.13-1.21 (m, 2H), 1.35 (t, J = 7.3 Hz, 6H), 1.42-1.49 (m, 2H), 1.89-2.21 (m, 4H), 2.37-2.52 (m, 1H), 2.52-2.64 (m, 1H), 4.06-4.25 (m, 4H), 4.71-4.97 (m, 2H), 7.29 (d, J = 10.4 Hz, 1H), 7.44 (d, J = 7.9 Hz, 2H), 7.91 (d, J = 4.9 Hz, 1H), 8.04 (d, J = 7.9 Hz, 2H), 8.79 (brs, 1H). | (ESI+) 575.1 (MH+) |
| 66B | 2-methyl-5-chlorothiazole | (DMSO-d6) δ 1.02-1.18 (m, 4H), 1.79-2.01 (m, 2H), 2.06-2.27 (m, 2H), 2.38-2.64 (m, 1H), 2.83-2.95 (m, 1H), 4.83-5.09 (m, 2H), 6.88 (d, J = 10.4 Hz, 1H), 7.47 (d, J = 8.6 Hz, 2H), 7.55 (d, J = 4.9 Hz, 1H), 7.91 (d, J = 7.9 Hz, 2H), 12.7 (brs, 1H). | (ESI+) 473.1 (MH+) |
| 67B | 2-methylthiazol-5-yl-CH₂CH₂OH | (CDCl3) δ 1.14-1.19 (m, 2H), 1.42-1.48 (m, 2H), 1.92-2.16 (m, 4H), 2.36-2.48 (m, 1H), 2.53-2.61 (m, 1H), 3.02 (t, J = 6.1 Hz, 2H), 3.86 (q, J = 5.5 Hz, 2H), 4.73-4.94 (m, 2H), 7.17 (s, 1H), 7.24 (m, 1H), 7.43 (d, J = 8.6 Hz, 2H), 8.03 (d, J = 8.6 Hz, 2H), 8.42 (s, 1H). | (ESI+) 483.1 (MH+) |
| 68B | 2-methylthiazol-5-yl-CH₂P(O)(OEt)₂ | (CDCl3) δ 1.15-1.20 (m, 2H), 1.32 (t, J = 7.0 Hz, 6H), 1.42-1.48 (m, 2H), 1.92-2.16 (m, 4H), 2.34-2.48 (m, 1H), 2.52-2.61 (m, 1H), 3.27 (d, J = 20.8 Hz, 2H), 4.10 (dd, J = 7.0 Hz, 2H), 4.13 (dd, J = 7.0 Hz, 2H), 4.73-4.82 (m, 1H), 4.85-4.95 (m, 1H), 7.26 (d, J = 10.4 Hz, 1H), 7.43 (d, J = 7.9 Hz, 2H), 8.03 (d, J = 8.6 Hz, 2H), 8.43 (s, 1H). | (ESI+) 589.1 (MH+) |
| 69B | 2-methylthiazol-5-yl-CH₂-(4-methylpiperazin-1-yl) | (DMSO-d6) δ 1.15-1.18 (m, 2H), 1.43-1.47 (m, 2H), 1.92-2.17 (m, 4H), 2.29 (s, 3H), 2.33-2.70 (m, 8H), 3.67 (s, 2H), 4.73-4.81 (m, 1H), 4.85-4.95 (m, 1H), 7.19 (s, 1H), 7.25 (d, J = 8.0 Hz, 1H), 7.43 (d, J = 8.6 Hz, 2H), 8.02 (d, J = 8.6 Hz, 2H). | (ESI+) 551.2 (MH+) |

TABLE 28

| | Structure | NMR | MS |
|---|---|---|---|
| 70B | 2-methylthiazol-5-yl-S-CH₂CH₂-NHBoc | (CDCl3) δ 1.16-1.19 (m, 2H), 1.44-1.48 (m, 11H), 1.92-2.19 (m, 4H), 2.34-2.50 (m, 1H), 2.53-2.62 (m, 1H), 2.84 (t, J = 6.1 Hz, 2H), 3.30 (t, J = 6.1 Hz, 2H), 4.73-4.96 (m, 3H), 7.26-7.28 (m, 1H), 7.41 (s, 1H), 7.43 (d, J = 8.6 Hz, 2H), 8.04 (d, J = 8.6 Hz, 2H), 8.43 (s, 1H). | (ESI+) 558.1 (MH+) |
| 71B | 2-methylthiazol-5-yl-S-CH₂CH₂-NH₂ | (CDCl3) δ 1.17-1.18 (m, 2H), 1.44-1.46 (m, 2H), 1.91-2.18 (m, 4H), 2.37-2.49 (m, 1H), 2.52-2.61 (m, 1H), 2.78-2.91 (m, 4H), 4.73-4.96 (m, 2H), 7.27 (d, J = 10.4 Hz, 1H), 7.40 (s, 1H), 7.40 (d, J = 8.6 Hz, 2H), 8.03 (d, J = 8.6 Hz, 2H). | (ESI+) 513.1 (MH+) |
| 72B | 2-methylthiazol-5-yl-S-CH₂CH₂-NMe₂ | (CDCl3) δ 1.14-1.20 (m, 2H), 1.44-1.47 (m, 2H), 1.92-2.17 (m, 4H), 2.24 (s, 6H), 2.37-2.46 (m, 1H), 2.51-2.60 (m, 1H), 2.85 (t, J = 7.5 Hz, 2H), 4.73-4.81 (m, 1H), 4.86-4.94 (m, 1H), 7.27 (d, J = 9.8 Hz, 1H), 7.43 (d, J = 7.9 Hz, 2H), 8.03 (d, J = 7.9 Hz, 2H), 8.45 (s, 1H). | (ESI+) 542.1 (MH+) |

TABLE 28-continued

| | | | |
|---|---|---|---|
| 73B | [structure: 2-methylthiazole-S-CH2CH2-NEt2] | (CDCl3) δ 0.95-1.05 (m, 6H), 1.14-1.20 (m, 2H), 1.42-1.48 (m, 2H), 1.93-2.18 (m, 4H), 2.36-2.48 (m, 1H), 2.48-2.61 (m, 5H), 2.66-2.76 (m, 2H), 2.78-2.89 (m, 2H), 4.73-4.94 (m, 2H), 7.26-7.29 (m, 1H), 7.39 (s, 1H), 7.43 (d, J = 8.6 Hz, 2H), 8.03 (d, J = 8.6 Hz, 2H), 8.40 (s, 1H). | (ESI+) 570.2 (MH+) |
| 74B | [structure: 2-methylthiazole-S-CH2CH2-pyrrolidine] | (CDCl3) δ 1.13-1.21 (m, 2H), 1.43-1.49 (m, 2H), 1.79 (brs, 4H), 1.92-2.18 (m, 4H), 2.35-2.62 (m, 6H), 2.72 (s, 2H), 2.89 (s, 2H), 4.72-4.95 (m, 2H), 7.26-7.29 (m, 1H), 7.39 (s, 1H), 7.43 (d, J = 8.6 Hz, 2H), 8.03 (d, J = 8.6 Hz, 2H), 8.38 (s, 1H). | (ESI+) 568.2 (MH+) |

TABLE 29

| | | | | |
|---|---|---|---|---|
| 75B | [structure: 2-methylthiazole-S-CH2CH2-N-methylpiperazine] | (CDCl3) δ 1.14-1.20 (m, 2H), 1.42-1.48 (m, 2H), 1.93-2.18 (m, 4H), 2.30 (s, 3H), 2.36-2.66 (m, 12H), 2.86 (dd, J = 8.9, 6.4 Hz, 2H), 4.73-4.95 (m, 2H) 7.26-7.29 (m, 1H), 7.43 (d, J = 8.6 Hz, 2H), 8.03 (d, J = 8.6 Hz, 2H), 8.39 (s, 1H). | (ESI+) 597.2 (MH+) | |
| 76B | [structure: 2-methylthiazole-S-CH2CH2-(3-fluoropyrrolidine)] | (CDCl3) δ 1.14-1.20 (m, 2H), 1.43-1.48 (m, 2H), 1.92-2.21 (m, 6H), 2.36-2.52 (m, 2H), 2.53-2.61 (m, 1H), 2.71-2.91 (m, 7H), 4.73-4.94 (m, 2H), 5.06-5.25 (m, 1H), 7.26-7.29 (m, 1H), 7.40 (s, 1H), 7.43 (d, J = 8.6 Hz, 2H), 8.04 (d, J = 8.6 Hz, 2H), 8.38 (s, 1H). | (ESI+) 586.1 (MH+) | (−) |
| 77B | [structure: 2-methylthiazole-S-CH2CH2-(3-fluoropyrrolidine)] | (CDCl3) δ 1.14-1.20 (m, 2H), 1.43-1.48 (m, 2H), 1.92-2.21 (m, 6H), 2.36-2.52 (m, 2H), 2.53-2.61 (m, 1H), 2.71-2.91 (m, 7H), 4.73-4.94 (m, 2H), 5.06-5.25 (m, 1H), 7.26-7.29 (m, 1H), 7.40 (s, 1H), 7.43 (d, J = 8.6 Hz, 2H), 8.04 (d, J = 8.6 Hz, 2H), 8.38 (s, 1H). | (ESI+) 586.1 (MH+) | (+) |
| 78B | [structure: 2-methylthiazole-S-CH2CH2-morpholine] | (CDCl3) δ 1.14-1.20 (m, 2H), 1.42-1.48 (m, 2H), 1.91-2.18 (m, 4H), 2.40-2.48 (m, 5H), 2.53-2.63 (m, 3H), 2.87 (dd, J = 8.3, 6.4 Hz, 2H), 3.70 (t, J = 4.6 Hz, 4H), 4.73-4.95 (m, 2H), 7.26-7.29 (m, 1H), 7.39 s, 1H), 7.43 (d, J = 8.6 Hz, 2H), 8.03 (d, J = 8.6 Hz, 2H), 8.42 (s, 1H). | (ESI+) 584.2 (MH+) | |
| 79B | [structure: 2-methylthiazole-S-CH2CH2-piperidine] | (CDCl3) δ 1.13-1.21 (m, 2H), 1.41-1.49 (m, 4H), 1.53-1.57 (m, 4H), 1.92-2.22 (m, 4H), 2.37-2.49 (m, 5H), 2.50-2.60 (m, 3H), 2.87 (dd, J = 8.9, 6.4 Hz, 2H), 4.72-4.97 (m, 2H), 7.26-7.29 (m, 1H), 7.38 (s, 1H), 7.43 (d, J = 8.6 Hz, 2H), 8.03 (d, J = 8.6 Hz, 2H), 8.41 (s, 1H). | (ESI+) 582.2 (MH+) | |

TABLE 30

| | | | |
|---|---|---|---|
| 80B | [structure: 2-methylthiazole-S-CH2CH2-(4,4-difluoropiperidine)] | (CDCl3) δ 1.14-1.20 (m, 2H), 1.43-1.48 (m, 2H), 1.90-2.18 (m, 8H), 2.36-2.49 (m, 1H), 2.50-2.61 (m, 5H), 2.65 (t, J = 7.3 Hz, 2H), 2.86 (t, J = 7.3 Hz, 2H), 4.73-4.95 (m, 2H), 7.26-7.29 (m, 1H), 7.39 (s, 1H), 7.43 (d, J = 8.6 Hz, 2H), 8.04 (d, J = 8.6 Hz, 2H), 8.41 (s, 1H). | (ESI+) 618.2 (MH+) |

TABLE 30-continued

| 81B | (structure) | (CDCl3) δ 1.14-1.21 (m, 2H), 1.42-1.49 (m, 2H), 1.91-2.17 (m, 5H), 2.37-2.49 (m, 1H), 2.53-2.61 (m, 1H), 2.92 (t, J = 5.9 Hz, 2H), 3.75 (q, J = 5.9 Hz, 2H), 4.73-4.95 (m, 2H), 7.26-7.29 (m, 1H), 7.42 (s, 1H), 7.43 (d, J = 7.9 Hz, 2H), 8.03 (d, J = 7.9 Hz, 2H), 8.45 (s, 1H). | (ESI+) 515.1 (MH+) |
|---|---|---|---|
| 82B | (structure) | (CDCl3) δ 1.14-1.20 (m, 2H), 1.42-1.48 (m, 2H), 1.70-1.91 (m, 4H), 1.91-2.18 (m, 4H), 2.23-2.32 (m, 1H), 2.36-2.49 (m, 1H), 2.53-2.68 (m, 3H), 2.84-2.98 (m, 3H), 3.13-3.20 (m, 1H), 3.38 (dd, J = 11.0, 3.1 Hz, 1H), 3.60 (dd, J = 11.0, 3.7 Hz, 1H), 4.73-4.95 (m, 2H), 7.26-7.29 (m, 1H), 7.41 (s, 1H), 7.43 (d, J = 7.9 Hz, 2H), 8.03 (d, J = 8.6 Hz, 2H), 8.43 (s, 1H). | (ESI+) 598.2 (MH+) |
| 83B | (structure) | (CDCl3) δ 1.16-1.20 (m, 2H), 1.44-1.48 (m, 2H), 1.91-2.18 (m, 4H), 2.37-2.50 (m, 1H), 2.52-2.61 (m, 1H), 3.06 (t, J = 7.0 Hz, 2H), 4.14 (t, J = 7.0 Hz, 2H), 4.77-4.92 (m, 2H), 6.91 (t, J = 1.2 Hz, 1H), 7.06 (s, 1H), 7.26-7.30 (m, 1H), 7.39 (s, 1H), 7.44 (d, J = 6.7 Hz, 2H), 8.04 (d, J = 6.7 Hz, 2H), 8.60 (s, 1H). | (ESI+) 565.1 (MH+) |

TABLE 31

| 84B | (structure) | (CDCl3) δ 1.13-1.21 (m, 2H), 1.25 (t, J = 7.1 Hz, 3H), 1.42-1.48 (m, 2H), 1.67-1.79 (m, 2H), 1.83-1.83 (m, 2H), 1.92-2.18 (m, 6H), 2.20-2.30 (m, 1H), 2.35-2.48 (m, 1H), 2.53-2.61 (m, 3H), 2.78-2.89 (m, 4H), 4.12 (q, J = 7.1 Hz, 2H), 4.73-4.95 (m, 2H), 7.26-7.30 (m, 1H), 7.38 (s, 1H), 7.43 (d, J = 8.6 Hz, 2H), 8.03 (d, J = 8.6 Hz, 2H), 8.40 (s, 1H). | (ESI+) 654.2 (MH+) | |
|---|---|---|---|---|
| 85B | (structure) | (CDCl3) δ 1.14-1.20 (m, 2H), 1.42-1.49 (m, 2H), 1.76-2.19 (m, 8H), 2.36-2.48 (m, 1H), 2.57 (tt, J = 7.9, 3.7 Hz, 1H), 2.67-2.73 (m, 1H), 2.86 (t, J = 7.0 Hz, 2H), 2.92-2.98 (m, 1H), 3.72 (s, 3H), 4.73-4.95 (m, 2H), 7.27 (d, J = 10.4 Hz, 1H), 7.39 (s, 1H), 7.43 (d, J = 8.6 Hz, 2H), 8.03 (d, J = 8.6 Hz, 2H), 8.42 (s, 1H). | (ESI+) 626.2 (MH+) | (−) |
| 86B | (structure) | (CDCl3) δ 1.14-1.21 (m, 2H), 1.42-1.48 (m, 2H), 1.74 (tt, J = 6.7, 6.7 Hz, 2H), 1.92-2.17 (m, 4H), 2.19 (s, 6H), 2.34 (t, J = 7.3 Hz, 2H), 2.36-2.47 (m, 1H), 2.57 (tt, J = 7.9, 3.8 Hz, 1H), 2.78 (t, J = 7.3 Hz, 2H), 4.73-4.94 (m, 2H), 7.26-7.29 (m, 1H), 7.37 (s, 1H), 7.43 (d, J = 8.6 Hz, 2H), 8.03 (d, J = 8.6 Hz, 2H), 8.37 (s, 1H). | (ESI+) 556.2 (MH+) | |
| 87B | (structure) | (DMSO-d6) δ 1.00-1.18 (m, 4H), 1.62-1.78 (m, 1H), 1.79-2.01 (m, 4H), 2.06-2.25 (m, 3H), 2.84-3.04 (m, 4H), 4.82-5.10 (m, 2H), 6.86 (d, J = 10.4 Hz, 1H), 7.47 (d, J = 8.6 Hz, 2H), 7.63 (s, 1H), 7.91 (d, J = 8.6 Hz, 2H). | (ESI+) 612.1 (MH+) | (−) |

TABLE 32

| 88B | (structure) | (DMSO-d6) δ 1.01-1.20 (m, 4H), 1.42-1.52 (m, 2H), 1.73 (dd, J = 13.1, 3.4 Hz, 2H), 1.82-2.01 (m, 4H), 2.08-2.24 (m, 3H), 2.73 (d, J = 11.0 Hz, 2H), 2.83 (t, J = 7.3 Hz, 2H), 2.85-2.94 (m, 1H), 4.84-5.08 (m, 2H), 6.85 (d, J = 10.4 Hz, 1H), 7.46 (d, J = 8.6 Hz, 2H), 7.54 (s, 1H), 7.90 (d, J = 8.6 Hz, 2H). | (ESI+) 648.1 (MH+) |
|---|---|---|---|

TABLE 32-continued

| | Structure | NMR | MS |
|---|---|---|---|
| 89B | (thiazole-S-CH2CH2-N-pyrrolidine with 3,3-difluoro) | (CDCl3) δ 1.15-1.20 (m, 2H), 1.43-1.48 (m, 2H), 1.91-2.19 (m, 6H), 2.35-2.50 (m, 1H), 2.53-2.60 (m, 1H), 2.74-2.92 (m, 6H), 3.04-3.12 (m, 2H), 4.71-5.11 (m, 4H), 5.06-5.25 (m, 1H), 7.26-7.29 (m, 1H), 7.39 (s, 1H), 7.43 (d, J = 7.9 Hz, 2H), 8.04 (d, J = 8.6 Hz, 2H), 8.42 (s, 1H). | (ESI+) 604.1 (MH+) |
| 90B | (thiazole-S-CH2CH2-N-pyrrolidine fused dioxolane with dimethyl) | (CDCl3) δ 1.14-1.20 (m, 2H), 1.31 (s, 3H), 1.42-1.48 (m, 2H), 1.51 (s, 3H), 1.92-2.19 (m, 6H), 2.36-2.48 (m, 1H), 2.53-2.61 (m, 1H), 2.66 (dd, J = 8.9, 6.4 Hz, 2H), 2.85 (dd, J = 8.9, 6.4 Hz, 2H), 3.05 (d, J = 11.6 Hz, 2H), 4.63 (q, J = 1.4 Hz, 2H), 4.73-4.94 (m, 2H), 7.26-7.29 (m, 1H), 7.39 (s, 1H), 7.43 (d, J = 8.6 Hz, 2H), 8.03 (d, J = 8.6 Hz, 2H), 8.40 (s, 1H). | (ESI+) 640.2 (MH+) |
| 91B | (thiazole-S-CH2CH2-NMeBoc) | (CDCl3) δ 1.14-1.20 (m, 2H), 1.37-1.49 (m, 11H), 1.92-2.17 (m, 4H), 2.36-2.49 (m, 1H), 2.54-2.60 (m, 1H), 2.83-2.86 (m, 5H), 3.33-3.46 (m, 2H), 4.73-4.95 (m, 2H), 7.26-7.29 (m, 1H), 7.41 (s, 1H), 7.43 (d, J = 8.6 Hz, 2H), 8.04 (d, J = 8.6 Hz, 2H), 8.41 (s, 1H). | (ESI+) 572.1 (MH+) |
| 92B | (thiazole-S-CH2CH2-N-pyrrolidine-3,4-diol) | (CDCl3) δ 1.13-1.20 (m, 2H), 1.42-1.48 (m, 2H), 1.91-2.17 (m, 4H), 2.36-2.50 (m, 1H), 2.50-2.62 (m, 3H), 2.63-2.75 (m, 6H), 2.83 (dd, J = 7.6, 5.8 Hz, 2H), 4.19 (s, 2H), 4.73-4.95 (m, 2H), 7.26-7.29 (m, 1H), 7.39 (s, 1H), 7.43 (d, J = 7.9 Hz, 2H), 8.03 (d, J = 7.9 Hz, 2H), 8.45 (s, 1H). | (ESI+) 600.1 (MH+) |

TABLE 33

| | Structure | NMR | MS | |
|---|---|---|---|---|
| 93B | (thiazole-S-CH2CH2CH2-OH) | (CDCl3) δ 1.13-1.21 (m, 2H), 1.34 (s, 1H), 1.42-1.49 (m, 2H), 1.82-1.89 (m, 2H), 1.91-2.18 (m, 4H), 2.34-2.50 (m, 1H), 2.52-2.61 (m, 1H), 2.86 (t, J = 7.3 Hz, 2H), 3.76 (q, J = 4.9 Hz, 2H), 4.73-4.95 (m, 2H), 7.26-7.29 (m, 1H), 7.42 (s, 1H), 7.43 (d, J = 7.9 Hz, 2H), 8.03 (d, J = 7.9 Hz, 2H), 8.43 (s, 1H). | (ESI+) 529.1 (MH+) | |
| 94B | (thiazole-S-CH2CH2-N-pyrrolidine-CO2Et) | (CDCl3) δ 1.14-1.21 (m, 2H), 1.25 (t, J = 7.1 Hz, 3H), 1.42-1.48 (m, 2H), 1.74-2.19 (m, 8H), 2.36-2.49 (m, 2H), 2.52-2.62 (m, 1H), 2.66-2.75 (m, 1H), 2.87 (t, J = 7.3 Hz, 2H), 2.92-2.99 (m, 1H), 3.15 (td, J = 8.3, 3.6 Hz, 1H), 3.22 (td, J = 9.4, 5.2 Hz, 1H), 4.17, (qd, J = 7.1, 1.8 Hz, 1H), 4.73-4.94 (m, 2H), 7.26 (d, J = 11.0 Hz, 1H), 7.39 (s, 1H), 7.43 (d, J = 8.5 Hz, 2H), 8.04 (d, J = 8.5 Hz, 2H), 8.39 (s, 1H). | (ESI+) 534.2 (MH+) | (−) |
| 95B | (thiazole-S-CH2CH2-NHMe) | (CDCl3) δ 1.14-1.20 (m, 2H), 1.42-1.49 (m, 2H), 1.92-2.19 (m, 4H), 2.38-2.51 (m, 1H), 2.38 (s, 3H), 2.53-2.61 (m, 1H), 2.79 (t, J = 6.1 Hz, 2H), 2.89 (t, J = 6.1 Hz, 2H), 4.73-4.95 (m, 2H), 7.26-7.30 (m, 1H), 7.39 (s, 1H), 7.43 (d, J = 8.6 Hz, 2H), 8.03 (d, J = 8.6 Hz, 2H). | (ESI+) 528.1 (MH+) | |
| 96B | (thiazole-S-CH2CH2-N-pyrrolidine-CO2Et · HCl) | (CDCl3) δ 1.14-1.21 (m, 2H), 1.25 (t, J = 7.1 Hz, 3H), 1.42-1.48 (m, 2H), 1.74-2.19 (m, 8H), 2.36-2.49 (m, 2H), 2.52-2.62 (m, 1H), 2.66-2.75 (m, 1H), 2.87 (t, J = 7.3 Hz, 2H), 2.92-2.99 (m, 1H), 3.15 (td, J = 8.3, 3.6 Hz, 1H), 3.22 (td, J = 9.4, 5.2 Hz, 1H), 4.17 (qd, J = 7.1, 1.8 Hz, 1H), 4.73-4.94 (m, 2H), 7.26 (d, J = 11.0 Hz, 1H), 7.39 (s, 1H), 7.43 (d, J = 8.5 Hz, 2H), 8.04 (d, J = 8.5 Hz, 2H), 8.39 (s, 1H). | (ESI+) 640.2 (MH+) | (−) |

TABLE 34

| 97B | 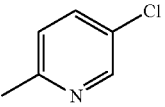 | (CDCl3) δ 1.10-1.18 (m, 2H), 1.41-1.48 (m, 2H), 1.91-2.19 (m, 4H), 2.35-2.49 (m, 1H), 2.51-2.61 (m, 1H), 4.70-4.96 (m, 2H), 7.13 (d, J = 10.4 Hz, 1H), 7.42-7.48 (m, 2H), 7.67 (brs, 1H), 7.70 (dd, J = 8.6, 2.4 Hz, 1H), 8.00-8.05 (m, 2H), 8.16 (d, J = 2.4 Hz, 1H), 8.30 (d, J = 8.6 Hz, 1H). | (ESI+) 467.1 (MH+) |
| --- | --- | --- | --- |
| 98B | 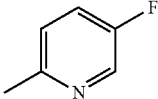 | (CDCl3) δ 1.09-1.19 (m, 2H), 1.40-1.48 (m, 2H), 1.89-2.20 (m, 4H), 2.35-2.49 (m, 1H), 2.50-2.61 (m, (1H), 4.71-4.95 (m, 2H), 7.13 (d, J = 10.4 Hz, 1H), 7.43-7.51 (m, 3H), 7.67 (brs, 1H), 7.99-8.05 (m, 2H), 8.06 (d, J = 3.1 Hz, 1H), 8.33 (dd, J = 9.2, 4.3 Hz, 1H). | (ESI+) 451.1 (MH+) |
| 99B | 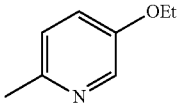 | (CDCl3) δ 1.41 (t, J = 7.3 Hz, 3H), 1.91-2.19 (m, 4H), 2.33-2.48 (m, 1H), 3.15 (s, 3H), 4.04 (q, J = 7.3 Hz, 2H), 4.71-4.94 (m, 2H), 7.11 (d, J = 10.4 Hz, 1H), 7.27 (dd, J = 9.2, 3.1 Hz, 1H), 7.45-7.50 (m, 2H), 7.54 (brs, 1H), 7.88 (d, J = 3.1 Hz, 1H), 8.03-8.08 (m, 2H), 8.22 (d, J = 9.2 Hz, 1H). | (ESI+) 451.2 (MH+) |
| 100B | 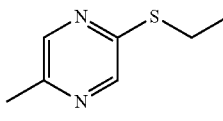 | (CDCl3) δ 1.09-1.19 (m, 2H), 1.40-1.48 (m, 2H), 1.91-2.19 (m, 4H), 2.36-2.50 (m, 1H), 2.50-2.60 (m, 1H), 3.08 (t, J = 6.1 Hz, 1H), 3.36 (t, J = 6.1 Hz, 2H), 3.92 (q, J = 6.1 Hz, 2H), 4.71-4.95 (m, 2H), 7.16 (d, J = 11.0 Hz, 1H), 7.43-7.48 (m, 2H), 7.51 (brs, 1H), 8.01-8.05 (m, 2H), 8.15 (d, J = 1.8 Hz, 1H), 9.41 (d, J = 1.8 Hz, 1H). | (ESI+) 510.1 (MH+) |
| 101B | 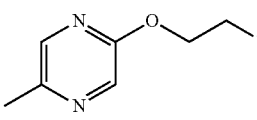 | (CDCl3) δ 1.07-1.17 (m, 2H), 1.41-1.47 (m, 2H), 1.93-2.17 (m, 4H), 2.33 (s, 6H), 2.33-2.46 (m, 1H), 2.51-2.59 (m, 1H), 2.71 (t, J = 5.5 Hz, 2H), 4.42 (t, J = 5.5 Hz, 2H), 4.72-4.94 (m, 2H), 7.15 (d, J = 10.4 Hz, 1H), 7.42 (s, 1H), 7.45 (d; J = 7.9 Hz, 2H), 7.90 (d, J = 1.2 Hz, 1H), 8.02 (d, J = 7.9 Hz, 2H), 9.09 (d, J = 1.2 Hz, 1H). | (ESI+) 521.2 (MH+) |

TABLE 35

| 102B | 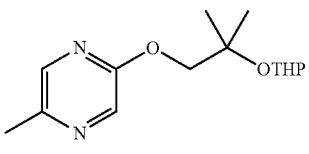 | (CDCl3) δ 1.11-1.17 (m, 2H), 1.34 (s, 3H), 1.35 (s, 3H), 1.42-1.54 (m, 6H), 1.59-1.68 (m, 1H), 1.82-1.93 (m, 1H), 1.93-2.18 (m, 4H), 2.36-2.48 (m, 1H), 2.51-2.60 (m, 1H), 3.37-3.95 (m, 1H), 3.88-3.95 (m, 1H), 4.26 (dd, J = 15.6, 10.7 Hz, 2H), 4.73-4.94 (m, 3H), 7.15 (d, J = 10.4 Hz, 1H), 7.44-7.47 (m, 3H), 7.89 (d, J = 1.2 Hz, 1H), 8.02 (d, J = 7.9 Hz, 2H), 9.09 (d, J = 1.2 Hz, 1H). | (ESI+) 606.2 (MH+) |
| --- | --- | --- | --- |
| 103B | 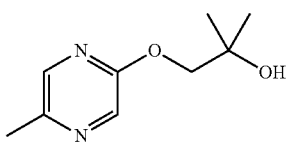 | (CDCl3) δ 1.11-1.18 (m, 2H), 1.33 (s, 6H),1.41-1.48 (m, 2H), 1.93-2.18 (m, 4H), 2.32 (s, 1H), 2.36-2.49 (m, 1H), 2.52-2.60 (m, 1H), 4.21 (s, 2H), 4.73-4.95 (m, 2H), 7.15 (d, J = 11.0 Hz, 1H), 7.49-7.47 (m, 3H), 7.92 (d, J = 1.2 Hz, 1H), 8.03 (d, J = 8.6 Hz, 2H), 9.10 (d, J = 1.2 Hz, 1H). | (ESI+) 521.2 (MH+) |
| 104B | 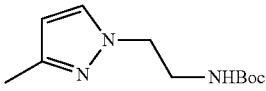 | (CDCl3) δ 1.09-1.19 (m, 2H), 1.34-1.49 (m, 2H), 1.42 (s, 9H), 1.89-2.18 (m, 4H), 2.31-2.46 (m, 1H), 2.50-2.60 (m, 1H), 3.45 (q, J = 5.5 Hz, 2H), 4.07 (t, J = 5.5 Hz, 2H), 4.65 (brs, 1H), 4.71-4.95 (m, 2H), 6.78 (d, J = 2.4 Hz, 1H), 7.11 (d, J = 10.4 Hz, 1H), 7.29 (d, J = 2.4 Hz, 1H), 7.42-7.46 (m, 2H), 7.50 (brs, 1H), 7.98-8.02 (m, 2H). | (ESI+) 565.2 (MH+) |
| 105B | 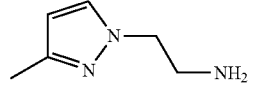 | (CDCl3) δ 1.09-1.20 (m, 2H), 1.37-1.48 (m, 2H), 1.89-2.18 (m, 4H), 2.30-2.46 (m, 1H), 2.50-2.61 (m, (1H), 3.07 (t, J = 5.5 Hz, 2H), 4.02 (t, J = 5.5 Hz, 2H), 4.69-4.94 (m, 2H), 6.79 (d, J = 2.4 Hz, 1H), 7.11 (d, J = 10.4 Hz, 1H), 7.35 (d, J = 2.4 Hz, 1H), 7.40-7.47 (m, 2H), 7.60 (brs, 1H), 7.96-8.03 (m, 2H). | (ESI+) 465.2 (MH+) |

TABLE 36

| 106B | 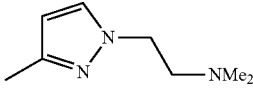 | (CDCl3) δ 1.12-1.18 (m, 2H), 1.42-1.47 (m, 2H), 1.91-2.15 (m, 4H), 2.23 (s, 6H), 2.31-2.43 (m, 1H), 2.52-2.60 (m, 1H), 2.65 (t, J = 6.7 Hz, 2H), 4.05 (t, J = 6.7 Hz, 2H), 4.71-4.79 (m, 1H), 4.84-4.92 (m, 1H), 6.77 (d, J = 2.4 Hz, 1H), 7.12 (d, J = 11.0 Hz, 1H), 7.36 (d, J = 2.4 Hz, 1H), 7.43 (d, J = 8.6 Hz, 2H), 7.51 (s, 1H), 7.99 (d, J = 8.6 Hz, 2H). | (ESI+) 493.2 (MH+) |
|---|---|---|---|
| 107B | 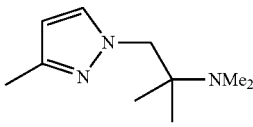 | (CDCl3) δ 1.12-1.17 (m, 2H), 1.42-1.46 (m, 2H), 1.49 (s, 6H), 1.91-2.16 (m, 4H), 1.97 (s, 6H), 2.34-2.43 (m, 1H), 2.47 (s, 2H), 2.53-2.60 (m, 1H), 4.72-4.80 (m, 1H), 4.85-4.93 (m, 1H), 6.75 (d, J = 2.4 Hz, 1H), 7.05 (d, J = 10.4 Hz, 1H), 7.05 (d, J = 8.6 Hz, 2H), 7.43 (s, 1H), 7.57 (s, 1H), 8.00 (d, J = 8.6 Hz, 2H). | (ESI+) 521.2 (MH+) |
| 108B | 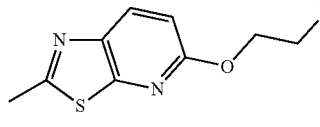 | (CDCl3) δ 1.11-1.23 (m, 2H), 1.40-1.51 (m, 2H), 1.91-2.20 (m, 5H), 2.29-2.53 (m, 1H), 2.35 (s, 6H), 2.74 (t, J = 5.5 Hz, 2H), 4.49 (t, J = 5.5 Hz, 2H), 4.72-4.96 (m, 2H), 6.87 (d, J = 8.6 Hz, 1H), 7.32 (d, J = 10.4 Hz, 1H), 7.47 (d, J = 8.6 Hz, 2H), 7.78 (d, J = 8.6 Hz, 1H), 8.05 (d, J = 7.9 Hz, 2H). | (ESI+) 577.2 (MH+) |
| 109B | 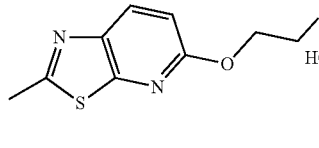 | (CDCl3) δ 1.15-1.22 (m, 2H), 1.44-1.50 (m, 2H), 1.95-2.20 (m, 4H), 2.40-2.52 (m, 1H), 2.55-2.62 (m, 1H), 2.92 (s, 6H), 3.44-3.54 (m, 2H), 4.75-4.96 (m, 4H), 6.90 (d, J = 8.6 Hz, 1H), 7.33 (d, J = 10.4 Hz, 1H), 7.48 (d, J = 8.6 Hz, 2H), 7.84 (d, J = 8.6 Hz, 1H), 8.06 (d, J = 8.6 Hz, 2H), 8.53 (s, 1H). | (ESI+) 577.2 (MH+) |

EXAMPLE 12

(E)-3-[(1α,3α,4α)-3,4-difluorocyclopentyl]-2-[4-(ethylthio)phenyl]acrylic acid ethyl ester

[Chemical formula 19]

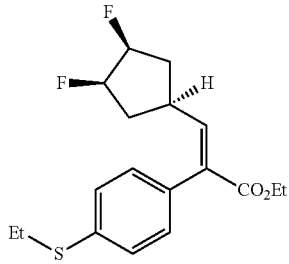

According to the method described in Example 1, (E)-3-[(1α,3α,4α)-3,4-difluorocyclopentyl]-2-[4-(ethylthio)phenyl]acrylic acid ethyl ester (773 mg), (Z)-3-[(1α,3α,4α)-3,4-difluorocyclopentyl]-2-[4-(ethylthio)phenyl]acrylic acid ethyl ester (498 mg), and 3-[(1α,3α,4α)-3,4-difluorocyclopentyl]-2-[4-(ethylthio)phenyl]acrylic acid ethyl ester (249 mg) (a mixture of E-form and Z-form) were obtained from (1α,3α,4α)-(3,4-difluorocyclopentyl)methyltriphenylphosphonium iodide (3.00 g) and 2-[(4-ethylthio)phenyl]oxoacetic acid ethyl ester (1.34 g). Of these compounds, only the title compound was used in the next step.

$^1$H NMR (400 MHz, CDCl$_3$) δ 1.28 (t, J=7.3 Hz, 3H), 1.35 (t, J=7.3 Hz, 3H), 1.88-2.18 (m, 4H), 2.55-2.68 (m, 1H), 2.97 (q, J=7.3 Hz, 2H), 4.22 (q, J=7.3 Hz, 2H), 4.70-4.96 (m, 2H), 6.97 (d, J=10.4 Hz, 1H), 7.05 (d, J=8.6 Hz, 2H), 7.29 (d, J=8.6 Hz, 2H).

MS (ESI$^+$) m/z: 341.1 (MH$^+$).

EXAMPLE 13

(E)-3-[(1α,3α,4α)-3,4-difluorocyclopentyl]-2-[4-(ethylsulfonyl)phenyl]acrylic acid ethyl ester

[Chemical formula 20]

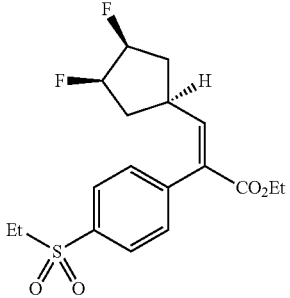

According to the method described in Example 2, (E)-3-[(1α,3α,4α)-3,4-difluorocyclopentyl]-2-[4-(ethylsulfonyl)phenyl]acrylic acid ethyl ester (665 mg) was obtained from (E)-3-[(1α,3α,4α)-3,4-difluorocyclopentyl]-2-[4-(ethylthio)phenyl]acrylic acid ethyl ester (730 mg) obtained in Example 12.

$^1$H NMR (400 MHz, CDCl$_3$) δ 1.18-1.40 (m, 6H), 1.90-2.20 (m, 4H), 2.45-2.58 (m, 1H), 3.16 (q, J=7.3 Hz, 2H), 4.24 (q, J=7.3 Hz, 2H), 4.71-4.95 (m, 2H), 7.09 (d, J=10.4 Hz, 1H), 7.35 (d, J=7.9 Hz, 2H), 7.92 (d, J=7.9 Hz, 2H).

MS (ESI$^+$) m/z: 373.1 (MH$^+$).

EXAMPLE 14

(E)-3-[(1α,3α,4α)-3,4-difluorocyclopentyl]-2-[4-(ethylsulfonyl)phenyl]acrylic acid

[Chemical formula 21]

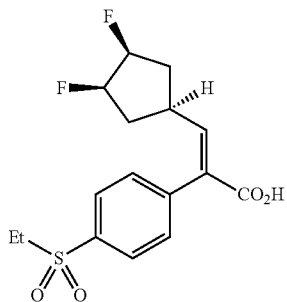

According to the method described in Example 4, (E)-3-[(1α,3α,4α)-3,4-difluorocyclopentyl]-2-[4-(ethylsulfonyl)phenyl]acrylic acid (420 mg) was obtained from (E)-3-[(1α,3α,4α)-3,4-difluorocyclopentyl]-2-[4-(ethylsulfonyl)phenyl]acrylic acid ethyl ester (634 mg) obtained in Example 13.

$^1$H NMR (400 MHz, CDCl$_3$) δ 1.33 (t, J=7.3 Hz, 3H), 1.88-2.21 (m, 4H), 2.47-2.62 (m, 1H), 3.15 (q, J=7.3 Hz, 2H), 4.71-4.99 (m, 2H), 7.24 (d, J=10.4 Hz, 1H), 7.36 (d, J=7.9 Hz, 2H), 7.93 (d, J=7.9 Hz, 2H).

MS (ESI$^+$) m/z: 345.1 (MH$^+$).

EXAMPLE 15

(E)-3-[(1α,3α,4α)-3,4-difluorocyclopentyl]-2-[4-(ethylsulfonyl)phenyl]-N-(thiazol-2-yl)acrylamide (compound 1C of the present invention)

[Chemical formula 22]

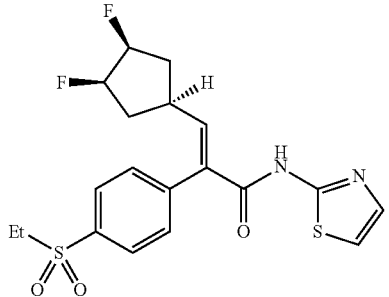

According to the method described in Example 5, (E)-3-[(1α,3α,4α)-3,4-difluorocyclopentyl]-2-[4-(ethylsulfonyl)phenyl]-N-(thiazol-2-yl)acrylamide (47.4 mg) was obtained from (E)-3-[(1α,3α,4α)-3,4-difluorocyclopentyl]-2-[4-(ethylsulfonyl)phenyl]acrylic acid (100 mg) obtained in Example 14 and 2-aminothiazole (29.0 mg).

$^1$H NMR (400 MHz, CDCl$_3$) δ 1.42 (t, J=7.3 Hz, 3H), 1.90-2.19 (m, 4H), 2.31-2.45 (m, 1H), 3.23 (q, J=7.3 Hz, 2H), 4.69-4.97 (m, 2H), 7.02 (d, J=3.3 Hz, 1H), 7.26 (d, J=10.4 Hz, 1H), 7.42 (d, J=3.3 Hz, 1H), 7.47 (d, J=8.6 Hz, 2H), 8.04 (d, J=8.6 Hz, 2H), 8.54 (brs, 1H).

MS (ESI$^+$) m/z: 427.1 (MH$^+$).

HRMS (ESI$^+$) for C$_{19}$H$_{21}$F$_2$N$_2$O$_3$S$_2$ (MH$^+$): calcd., 427.09616; found, 427.09624.

EXAMPLE 16

Compounds 2C and 3C of the present invention were produced according to the same procedure as in Example 15.

[Chemical formula 23]

TABLE 37

| Compound No. | Structure (A) | 1H NMR (400 MHz) | MS (m/z) |
|---|---|---|---|
| 2C | ![pyrazine with Me] | (CDCl3) δ 1.39 (t, J = 7.3 Hz, 3H), 1.91-2.21 (m, 4H), 2.35-2.49 (m, 1H), 2.53 (s, 3H), 3.21 (q, J = 7.3 Hz, 2H), 4.71-4.97 (m, 2H), 7.15 (d, J = 10.4 Hz, 1H), 7.49 (d, J = 7.9 Hz, 2H), 7.53 (s, 1H), 8.04 (d, J = 7.9 Hz, 2H), 8.05 (s, 1H), 9.49 (s, 1H). | (ESI+) 436.2 (MH+) |
| 3C | ![pyrazole with Me] | (CDCl3) δ 1.40 (t, J = 7.3 Hz, 3H), 1.85-2.17 (m, 4H), 2.29-2.44 (m, 1H), 3.20 (q, J = 7.3 Hz, 2H), 3.75 (s, 3H), 4.66-4.95 (m, 2H), 6.75 (d, J = 2.4 Hz, 1H), 7.11 (d, J = 10.4 Hz, 1H), 7.41-7.50 (m, 3H), 8.00 (d, J = 7.9 Hz, 2H). | (ESI+) 424.2 (MH+) |

EXAMPLE 17

2-[4-(2-Methoxyethylthio)phenyl]-2-oxoacetic acid ethyl ester

[Chemical formula 24]

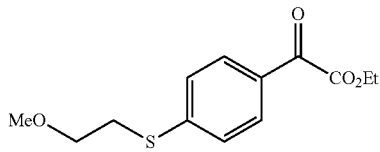

Ethyl chloroglyoxylate (8.76 mL) was added dropwise to a suspension of aluminum chloride (13.2 g, crushed) in methylene chloride (127 mL) under stirring and cooling with ice, and (2-methoxyethyl)phenylsulfide (12.0 g) was added dropwise thereto. The mixture was stirred at room temperature for 2 hours. The reaction mixture was poured into ice water (200 mL), and the mixture was stirred for 10 minutes. The organic layer was separated, washed with a saturated aqueous sodium hydrogen carbonate solution (40 mL×3), and washed with saturated brine (60 mL). The washed organic layer was dried over anhydrous sodium sulfate, filtrated, and evaporated under reduced pressure. The obtained residue was purified by column chromatography (silica gel, hexane:ethyl acetate=4:1) to give 2-[4-(2-methoxyethylthio)phenyl]-2-oxoacetic acid ethyl ester (1.98 g).

$^1$H NMR (400 MHz, CDCl$_3$) δ 1.42 (t, J=7.0 Hz, 3H), 3.23 (t, J=6.7 Hz, 2H), 3.39 (s, 3H), 3.65 (t, J=6.7 Hz, 2H), 4.44 (q, J=7.0 Hz, 2H), 7.36 (d, J=8.6 Hz, 2H), 7.92 (d, J=8.6 Hz, 2H).
MS (ESI$^+$) m/z: 269.1 (MH$^+$).

EXAMPLE 18

(E)-3-[(1α,3α,4α)-3,4-difluorocyclopentyl]-2-[4-(methoxyethylthio)phenyl]acrylic acid ethyl ester

[Chemical formula 25]

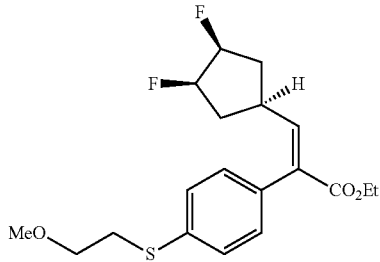

According to the method described in Example 1, (E)-3-[(1α,3α,4α)-3,4-difluorocyclopentyl]-2-[4-(methoxyethylthio)phenyl]acrylic acid ethyl ester (639 mg), (Z)-3-[(1α,3α,4α)-3,4-difluorocyclopentyl]-2-[4-(methoxyethylthio)phenyl]acrylic acid ethyl ester (67 mg), and 3-[(1α,3α,4α)-3,4-difluorocyclopentyl]-2-[4-(methoxyethylthio)phenyl]acrylic acid ethyl ester (1.01 g) (a mixture of E form and Z form) were obtained from (1α,3α,4α)-(3,4-difluorocyclopentyl)methylphosphonium iodide (3.00 g) and 2-[4-(2-methoxyethylthio)phenyl]-2-oxoacetic acid ethyl ester (1.51 g) obtained in Example 17. Of these compounds, only the title compound was used in the next step.

$^1$H NMR (400 MHz, CDCl$_3$) δ 1.28 (t, J=7.1 Hz, 3H), 1.86-2.19 (m, 4H), 2.54-2.67 (m, 1H), 3.14 (t, J=6.7 Hz, 2H), 3.38 (s, 3H), 3.61 (t, J=6.7 Hz, 2H), 4.22 (q, J=7.1 Hz, 2H), 4.71-4.94 (m, 2H), 6.97 (d, J=10.4 Hz, 1H), 7.06 (d, J=8.6 Hz, 2H), 7.34 (d, J=8.6 Hz, 2H).
MS (ESI$^+$) m/z: 339.1 (MH$^+$).

EXAMPLE 19

(E)-3-[(1α,3α,4α)-3,4-difluorocyclopentyl]-2-[4-(2-methoxyethylsulfonyl)phenyl]acrylic acid ethyl ester

[Chemical formula 26]

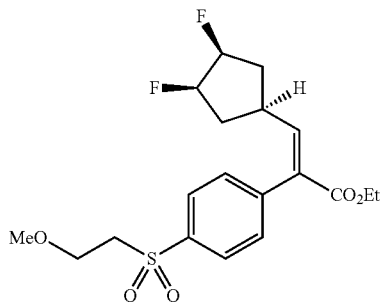

According to the method described in Example 2, (E)-3-[(1α,3α,4α)-3,4-difluorocyclopentyl]-2-[4-(2-methoxyethylsulfonyl)phenyl]acrylic acid ethyl ester (573 mg) was obtained from (E)-3-[(1α,3α,4α)-3,4-difluorocyclopentyl]-2-[4-(methoxyethylthio)phenyl]acrylic acid ethyl ester (600 mg) obtained in Example 18.

$^1$H NMR (400 MHz, CDCl$_3$) δ 1.29 (t, J=7.1 Hz, 3H), 1.90-2.18 (m, 4H), 2.45-2.57 (m, 1H), 3.26 (s, 3H), 3.42 (t, J=6.4 Hz, 2H), 3.79 (t, J=6.4 Hz, 2H), 4.23 (q, J=7.1 Hz, 2H), 4.73-4.95 (m, 2H), 7.09 (d, J=10.4 Hz, 1H), 7.34 (d, J=8.6 Hz, 2H), 7.92 (d, J=8.6 Hz, 2H).
MS (CI$^+$) m/z: 403.1 (MH$^+$).

EXAMPLE 20

(E)-3-[(1α,3α,4α)-3,4-difluorocyclopentyl]-2-[4-(2-methoxyethylsulfonyl)phenyl]acrylic acid

[Chemical formula 27]

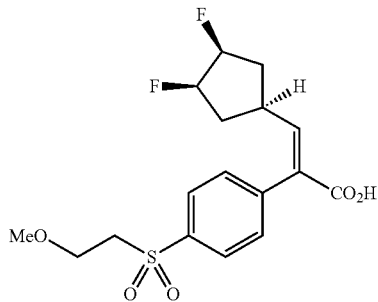

According to the method described in Example 4, (E)-3-[(1α,3α,4α)-3,4-difluorocyclopentyl]-2-[4-(2-methoxyethylsulfonyl)phenyl]acrylic acid (428 mg) was obtained from (E)-3-[(1α,3α,4α)-3,4-difluorocyclopentyl]-2-[4-(2-methoxyethylsulfonyl)phenyl]acrylic acid ethyl ester (550 mg) obtained in Example 19.

$^1$H NMR (400 MHz, CDCl$_3$) δ 1.91-2.19 (m, 4H), 2.49-2.61 (m, 1H), 3.26 (s, 3H), 3.42 (t, J=6.1 Hz, 2H), 3.79 (t, J=6.1 Hz, 2H), 4.74-4.96 (m, 2H), 7.23 (d, J=10.4 Hz, 1H), 7.35 (d, J=7.9 Hz, 2H), 7.93 (d, J=7.9 Hz, 2H).

MS (CI$^+$) m/z: 375.1 (MH$^+$).

EXAMPLE 21

(E)-3-[(1α,3α,4α)-3,4-difluorocyclopentyl]-2-[4-(2-methoxyethylsulfonyl)phenyl]-N-(thiazol-2-yl)acrylamide

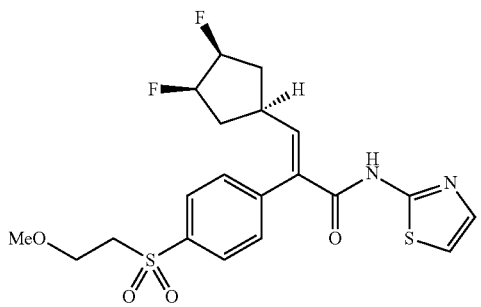

[Chemical formula 27]

According to the method described in Example 5, (E)-3-[(1α,3α,4α)-3,4-difluorocyclopentyl]-2-[4-(2-methoxyethylsulfonyl)phenyl]-N-(thiazol-2-yl)acrylamide (44.8 mg) was obtained from (E)-3-[(1α,3α,4α)-3,4-difluorocyclopentyl]-2-[4-(2-methoxyethylsulfonyl)phenyl]acrylic acid (100 mg) obtained in Example 20 and 2-aminothiazole (26.7 mg).

$^1$H NMR (400 MHz, CDCl$_3$) δ 1.90-2.20 (m, 4H), 2.38-2.52 (m, 1H), 3.31 (s, 3H), 3.48 (t, J=5.8 Hz, 2H), 3.87 (t, J=5.8 Hz, 2H), 4.72-4.95 (m, 2H), 7.01 (d, J=3.7 Hz, 1H), 7.26 (d, J=10.4 Hz, 1H), 7.40 (d, J=3.7 Hz, 1H), 7.45 (d, J=7.9 Hz, 2H), 8.05 (d, J=7.9 Hz, 2H), 8.63 (brs, 1H).

MS (ESI$^+$) m/z: 457.1 (MH$^+$).

HRMS (ESI$^+$) for C$_{20}$H$_{23}$F$_2$N$_2$O$_4$S$_2$ (MH$^+$): calcd., 457.10673; found, 457.10653.

EXAMPLE 22

Compounds 2D and 3D of the present invention were produced according to the same procedure as in Example 21.

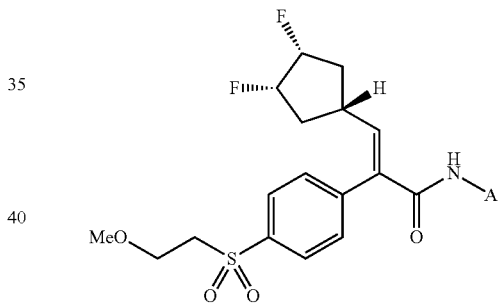

[Chemical formula 29]

TABLE 38

| Compound No. | Structure (A) | 1H NMR (400 MHz) | MS (m/z) |
|---|---|---|---|
| 2D | pyrazine-Me | (CDCl3) δ 1.90-2.22 (m, 4H), 2.36-2.50 (m, 1H), 2.52 (s, 3H), 3.27 (s, 3H), 3.47 (t, J = 5.8 Hz, 2H), 3.84 (t, J = 5.8 Hz, 2H), 4.70-4.95 (m, 2H), 7.17 (d, J = 10.4 Hz, 1H), 7.46 (d, J = 7.9 Hz, 1H), 7.50 (brs, 1H), 8.03 (brs, 1H), 8.05 (d, J = 7.9 Hz, 2H), 9.48 (s, 1H). | (ESI+) 466.2 (MH+) |
| 3D | pyrazole-Me, N-Me | (CDCl3) δ 1.88-2.16 (m, 4H), 2.30-2.46 (m, 1H), 3.31 (s, 3H), 3.46 (t, J = 5.8 Hz, 2H), 3.75 (s, 3H), 3.85 (t, J = 5.8 Hz, 2H), 4.66-4.96 (m, 2H), 6.74 (d, J = 2.4 Hz, 1H), 7.11 (d, J = 11.0 Hz, 1H), 7.25 (d, J = 2.4 Hz, 1H), 7.44 (d, J = 7.9 Hz, 2H), 7.47 (brs, 1H), 8.02 (d, J = 7.9 Hz, 2H). | (ESI+) 454.2 (MH+) |

EXAMPLE 23

Ethyl 2-(5-{(E)-2-[4-(cyclopropylsulfonyl)phenyl]-3-[(1α,3α,4α)-3,4-difluorocyclopentyl]acrylamide}pyrazin-2-yloxy)acetate First Step 5-(4-Methoxybenzyloxy)pyrazin-2-amine

[Chemical formula 30]

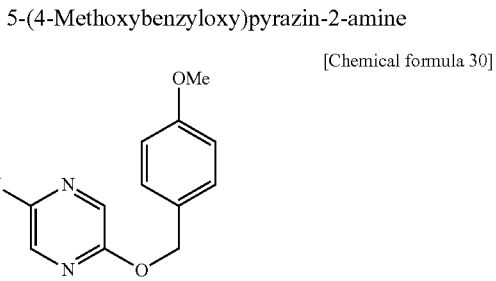

Sodium hydride (60% oily product) (78.8 mg) was added to 4-methoxybenzyl alcohol (2.14 mL) at a room temperature in an argon atmosphere, and the mixture was stirred for 30 minutes under the same conditions. Next, the reaction mixture was transferred to a metal seal tube. A copper powder (146 mg) and 2-amino-5-bromopyrazine (300 mg) were added, and the resultant mixture was heated and stirred at 160° C. for about 6 hours. After cooling, 25% aqueous ammonia and water were poured into the reaction solution. The reaction mixture was stirred for 1 hour at room temperature, and then filtrated through Celite. Water (20 mL) was added to the filtrate, and the resultant mixture was extracted with ethyl acetate (20 mL×3). The organic layer was washed with saturated brine (50 mL). The washed organic layer was dried over anhydrous sodium sulfate and filtrated, and then the solvent was removed under reduced pressure. The obtained residue was purified by silica gel column chromatography (elution solvent; hexane:ethyl acetate=3:1) to give 5-(4-methoxybenzyloxy)pyrazin-2-amine (104 mg).

$^1$H NMR (CHCl$_3$, 400 MHz) •3.81 (s, 3H), 4.12 (brs, 2H), 5.21 (s, 2H), 6.90 (d, J=8.5 Hz, 2H), 7.37 (d, J=8.5 Hz, 2H), 7.56 (d, J=1.2 Hz, 1H), 7.79 (d, J=1.2 Hz, 1H).

MS (EI) m/z: 231.1 (M$^+$).

HRMS (EI$^+$) for C$_{12}$H$_{13}$N$_3$O$_2$ (M$^+$): calcd., 231.1008; found, 231.0988.

Second Step (E)-2-[4-(cyclopropylsulfonyl)phenyl]-3-[(1α,3α,4α)-3,4-difluorocyclopentyl]-N-[5-(4-methoxybenzyloxy)pyrazin-2-yl]acrylamide

[Chmical formula 31]

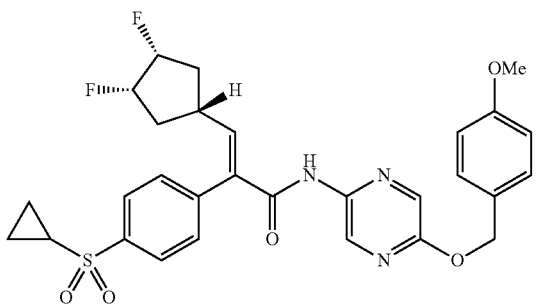

A solution of 5-(4-methoxybenzyloxy)pyrazin-2-amine (90 mg) in anhydrous pyridine (0.49 mL) was added dropwise at a room temperature in an argon atmosphere into a solution of an acid chloride (146 mg) of the (E)-2-[4-(cyclopropylsulfonyl)phenyl]-3-[(1α,3α,4α)-3,4-difluorocyclopentyl]acrylamide obtained in Example 10 in anhydrous tetrahydrofuran (0.49 mL), and the resultant mixture was stirred for about 2 hours at room temperature. Ethyl acetate was added to the reaction mixture, and the mixture was then washed with a 10% citric acid aqueous solution. The organic layer was washed with a saturated sodium hydrogen carbonate aqueous solution (10 mL×2), and then washed with saturated brine (10 mL). The washed organic layer was dried over anhydrous sodium sulfate and filtrated, and then the solvent was removed under reduced pressure. The obtained residue was purified by silica gel column chromatography (elution solvent; hexane:ethyl acetate=1:1) to give (E)-2-[4-(cyclopropylsulfonyl)phenyl]-3-[(1α,3α,4α)-3,4-difluorocyclopentyl]-N-[5-(4-methoxybenzyloxy)pyrazin-2-yl]acrylamide (160 mg).

$^1$H NMR (CHCl$_3$, 400 MHz) •1.10-1.17(m, 2H),1.40-1.48 (m, 2H),1.94-2.20 (m, 4H),2.36-2.49(m, 1H),2.51-2.59(m, 1H),3.81 (s, 3H),4.72-4.94 (m, 2H), 5.32 (s, 2H), 6.90 (d, J=8.5 Hz, 2H), 7.15 (d, J=10.3 Hz, 1H), 7.38 (d, J=8.5 Hz, 2H), 7.44 (brs, 1H), 7.46 (d, J=8.5 Hz, 2H), 7.86 (d, J=1.2 Hz, 1H), 8.02 (d, J=8.5 Hz, 2H), 9.13 (d, J=1.2 Hz, 1H).

MS (ESI$^+$) m/z: 570.2 (MH$^+$).

HRMS (ESI$^+$) for C$_{29}$H$_{30}$F$_2$N$_3$O$_5$S calcd., 570.18742; found, 570.18681.

Third Step (E)-2-[4-(cyclopropylsulfonyl)phenyl]-3-[(1α,3α,4α)-3,4-difluorocyclopentyl]-N-(5-hydroxypyrazin-2-yl)acrylamide

[Chemical formula 32]

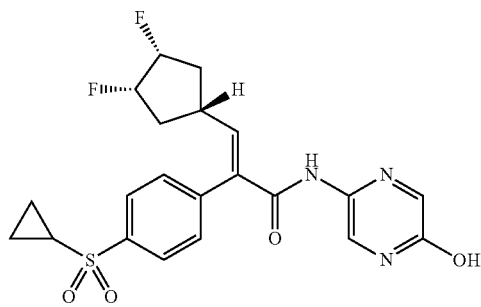

Trifluoroacetic acid (1 mL) was added at a room temperature in an argon atmosphere to a solution of (E)-2-[4-(cyclopropylsulfonyl)phenyl]-3-[(1α,3α,4α)-3,4-difluorocyclopentyl]-N-[5-(4-methoxybenzyloxy)pyrazin-2-yl] acrylamide (100 mg) in anhydrous dichloromethane (1 mL), and the resultant mixture was stirred for 5 minutes. A saturated sodium hydrogen carbonate aqueous solution was added to the reaction mixture to adjust the pH to 8. The reaction mixture was then extracted with chloroform (20 mL×2). The organic layer was washed with saturated brine (20 mL). The washed organic layer was then dried over anhydrous sodium sulfate and filtrated, and then the solvent was removed under reduced pressure. The obtained residue was purified by silica gel column chromatography (elution solvent; chloroform:acetone=5:1) to give (E)-2-[4-(cyclopropylsulfonyl)phenyl]-3-[(1α,3α,4α)-3,4-difluorocyclopentyl]-N-(5-hydroxypyrazin-2-yl)acrylamide (41 mg).

$^1$H NMR (CHCl$_3$, 400 MHz) •1.11-1.18(m, 2H),1.41-1.48 (m, 2H),1.92-2.18 (m, 4H), 2.36-2.49 (m, 1H), 2.52-2.60 (m, 1H), 4.74-4.95 (m, 2H), 7.11 (d, J=10.9 Hz, 1H), 7.28 (brs, 1H), 7.44 (d, J=8.5 Hz, 2H), 7.95 (d, J=1.2 Hz, 1H), 8.03 (d, J=8.5 Hz, 2H), 8.48 (d, J=1.2 Hz, 1H).

MS (ESI$^+$) m/z: 450.1 (MH$^+$)

HRMS (ESI+) for $C_{21}H_{22}F_2N_3O_4S$ (MH+): calcd., 450.12991; found, 450.12959.

Fourth Step

Ethyl 2-(5-{(E)-2-[4-(cyclopropylsulfonyl)phenyl]-3-[(1α,3α,4α)-3,4-difluorocyclopentyl]acrylamide}pyrazin-2-yloxy)acetate

[Chemical formula 33]

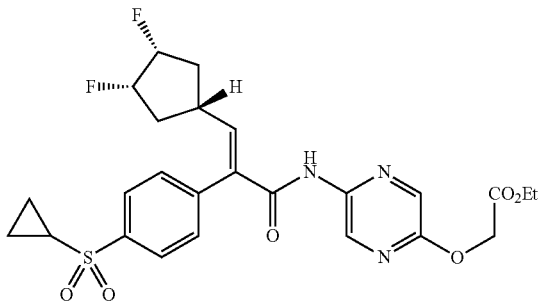

Ethyl bromoacetate (74 μL) and silver oxide (92.9 mg) were added at a room temperature in an argon atmosphere to a solution of (E)-2-[4-(cyclopropylsulfonyl)phenyl]-3-[(1α,3α,4α)-3,4-difluorocyclopentyl]-N-(5-hydroxypyrazin-2-yl)acrylamide (150 mg) in anhydrous toluene (5 mL), and the resultant mixture was heated and stirred for about 22 hours at 100° C. in an argon atmosphere. The reaction mixture was cooled, and then filtrated through Celite. After filtration, the solvent was removed under reduced pressure. The obtained residue was purified by silica gel column chromatography (elution solvent; chloroform:acetone=5:1) to give ethyl 2-(5-{(E)-2-[4-(cyclopropylsulfonyl)phenyl]-3-[(1α,3α,4α)-3,4-difluorocyclopentyl]acrylamide}pyrazin-2-yloxy)acetate (35 mg). IR (ATR) 3300, 2983, 1746, 1666, 1603, 1519, 1400, 1375, 1353, 1316, 1292, 1208, 1186, 1140, 1087, 1044, 1025, 994, 972 $cm^{-1}$.

$^1$H NMR (CHCl$_3$, 400 MHz) •1.11-1.18 (m, 2H), 1.29 (t, J=7.3 Hz, 3H), 1.41-1.48 (m, 2H), 1.92-2.20 (m, 4H), 2.35-2.48 (m, 1H), 2.52-2.60 (m, 1H), 4.24 (q, J=7.3 Hz, 2H), 4.73-4.95 (m, 2H), 4.90 (s, 2H), 7.15 (d, J=10.3 Hz, 1H), 7.45 (d, J=8.5 Hz, 2H), 7.47 (brs, 1H), 7.98 (d, J=1.2 Hz, 1H), 8.03 (d, J=8.5 Hz, 2H), 9.08 (d, J=1.2 Hz, 1H).

MS (ESI+) m/z: 536.2 (MH+).

HRMS (ESI+) for $C_{25}H_{28}F_2N_3O_6S$ (MH+): calcd., 536.16696; found, 536.16654.

EXAMPLE 24

2-(5-{(E)-2-[4-(cyclopropylsulfonyl)phenyl]-3-[(1α,3α,4α)-3,4-difluorocyclopentyl]acrylamide}pyrazin-2-yloxy)acetic acid

[Chemical formula 34]

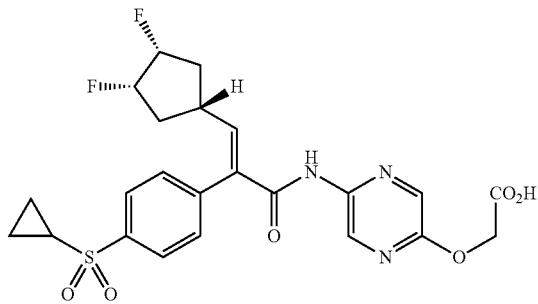

IR (ATR) 3304, 2942, 2535, 1729, 1665, 1609, 1520, 1469, 1437, 1360, 1314, 1288, 1239, 1200, 1177, 1141, 1071, 1048, 1028, 994, 973 $cm^{-1}$.

$^1$H NMR (DMSO, 400 MHz) •1.00-1.18(m, 4H),1.81-2.00 (m, 2H),2.06-2.25 (m, 2H),2.45-2.60(m, 1H),2.85-2.92(m, 1H),4.83(s, 2H),4.83-5.06 (m, 2H), 6.69 (d, J=10.3 Hz, 1H), 7.47 (d, J=8.5 Hz, 2H), 7.89 (d, J=8.5 Hz, 2H), 8.21 (d, J=1.2 Hz, 1H), 8.72 (d, J=1.2 Hz, 1H), 10.7 (s, 1H), 13.0 (brs, 1H).

MS (ESI+) m/z: 508.1 (MH+).

HRMS (ESI+) for $C_{23}H_{24}F_2N_3O_6S$ (MH+): calcd., 508.13539; found, 508.13523.

REFERENCE EXAMPLE 1

(1α,3α,4α)-3,4-Difluorocyclopentylmethyltriphenylphosphonium iodide

First Step

[(1α,3α, 4α)-3,4-Dihydroxycyclopentyl]methyl benzoate

[Chemical formula 35]

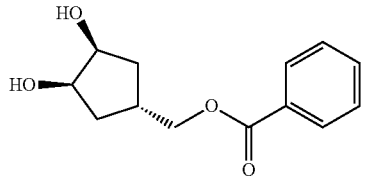

N-methylmorpholine N-oxide (a 50% aqueous solution, 22.0 mL) and osmium tetroxide (a 2.5% t-butanol solution, 1.90 mL) were dissolved in acetone (190 mL). A solution of (3-cyclopenten-1-yl)methyl benzoate (WO93/18009, Japanese Translation of PCT International Application No. Hei 7-506816) (20.2 g) in acetone (125 mL) was added dropwise to the prepared solution over 105 minutes under stirring, and the mixture was stirred at room temperature for 15 hours. Chloroform (310 mL) and water (190 mL) were added to the reaction mixture, and the organic layer was collected. The collected organic layer was washed sequentially with 1 mol/L hydrochloric acid (2×90 mL), water (90 mL), and a saturated aqueous sodium hydrogen carbonate solution (60 mL), dried over anhydrous sodium sulfate, and concentrated under reduced pressure. Toluene (120 mL) was added to the residue, and the precipitated crystals were collected by filtration to give [(1α, 3β,4β)-3,4-dihydroxycyclopentyl]methyl benzoate (16.9 g).

$^1$H NMR (CDCl$_3$) δ 1.71-1.78 (m, 2H), 1.95-2.02 (m, 2H), 2.27 (br, 2H), 2.75-2.87 (m, 1H), 4.19-4.23 (m, 4H), 7.43-7.47 (m, 2H), 7.55-7.59 (m, 1H), 8.01-8.04 (m, 2H).

The filtrate was concentrated under reduced pressure to give a mixture of [(1α,3β,4β)-3,4-dihydroxycyclopentyl]methyl benzoate and [(1β,3β,4β)-3,4-dihydroxycyclopentyl]methyl benzoate (4.23 g, a ratio of about 1:2 determined by the integration ratio of $^1$HNMR).

$^1$H NMR (CDCl$_3$) δ 1.58-1.65 (m, 1.3H), 1.71-1.78 (m, 0.7H), 1.96-2.17 (m, 2H), 2.75-2.85 (m, 1H), 4.09-4.32 (m, 4H), 7.42-7.46 (m, 2H), 7.54-7.59 (m, 1H), 8.01-8.06 (m, 2H).

Second Step (3aα,5α,6aα)-(Tetrahydro-4H-cyclopenta-1,3,2-dioxathiol-5-yl)methyl benzoate S,S-dioxide

[Chemical formula 36]

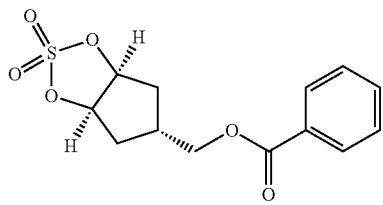

[(1α,3β,4β)-3,4-Dihydroxycyclopentyl]methylbenzoate (5.00 g) was suspended in carbon tetrachloride (75 mL). Thionyl chloride (1.90 mL) was added to the suspension, and the mixture was heated for reflux under stirring for 1.5 hours. Thionyl chloride (0.50 mL) was further added to the reaction mixture, and the mixture was heated for reflux under stirring for 1 hour. The reaction mixture was concentrated under reduced pressure, and toluene (25 mL) was added to the residue. The mixture was concentrated under reduced pressure and dried under reduced pressure to give (3aα,5α,6aα)-(tetrahydro-4H-cyclopenta-1,3,2-dioxathiol-5-yl)methyl benzoate S-oxide (6.09 g). The obtained (3aα,5α,6aα)-(tetrahydro-4H-cyclopenta-1,3,2-dioxathiol-5-yl)methyl benzoate S-oxide (4.27 g) was mixed with acetonitrile (30 mL) and carbon tetrachloride (30 mL). Sodium periodate (6.46 g), ruthenium chloride hydrate (31.3 mg), and then water (30 mL) were added to the mixture, and the resultant mixture was stirred at room temperature for 30 minutes. Dichloromethane (50 mL) was added to the reaction mixture, and insoluble materials were removed by filtration. Then, the organic layer of the filtrate was separated, and the aqueous layer was extracted with dichloromethane (50 mL). The organic layer and the dichloromethane extract were combined. The combined solution was washed with a 1 mol/L aqueous sodium thiosulfate solution (2×40 mL) and then with water (2×40 mL), dried over anhydrous sodium sulfate, and concentrated under reduced pressure. The residue was dried under reduced pressure to give (3aα,5α,6aα)-(tetrahydro-4H-cyclopenta-1,3,2-dioxathiol-5-yl)methyl benzoate S,S-dioxide (4.35 g).

MS (CI$^+$) m/z: 299 (MH$^+$).

HRMS (CI$^+$) for $C_{13}H_{15}O_6S$ (MH$^+$): calcd., 299.0589; found, 299.0593.

Third Step

[(1α,3α,3β)-3-Fluoro-4-hydroxycyclopentyl]methyl benzoate

[Chemical formula 37]

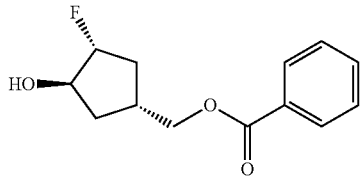

Tetrabutylammonium fluoride hydrate (571 mg) was dissolved in anhydrous acetonitrile (5 mL), and the prepared solution was concentrated under reduced pressure. The same procedure was repeated additional two times, and the residue was dried under reduced pressure at 40° C. for 45 minutes. The resultant residue was dissolved in dehydrated acetonitrile (5 mL). (3aα,5α,6aα)-(Ttetrahydro-4H-cyclopenta-1,3,2-dioxathiol-5-yl)methyl benzoate S,S-dioxide (500 mg) was added to the prepared solution, and the mixture was heated to reflux under stirring for 45 minutes. Then, the reaction mixture was concentrated under reduced pressure. The residue was dissolved in ethanol (5 mL), and sulfuric acid (0.15 mL) was added thereto. The mixture was heated to reflux under stirring for 10 minutes, and the reaction mixture was concentrated under reduced pressure. The residue was dissolved in ethyl acetate (40 mL). The resultant solution was washed with a saturated aqueous sodium hydrogen carbonate solution (5 mL) and then with saturated brine (5 mL), dried over anhydrous sodium sulfate, and concentrated under reduced pressure. The residue was purified by silica gel column chromatography (eluent:hexane/ethyl acetate=1:1) to give [(1α,3α,4β)-3-fluoro-4-hydroxycyclopentyl]methyl benzoate (342 mg).

MS (EI) m/z: 238 (M$^+$).

HRMS (EI) for $C_{13}H_{15}FO_3$(M$^+$): calcd., 238.1005; found, 238.1046.

Fourth Step

[(1α,3α,4α)-3,4-Difluorocyclopentyl]methyl benzoate

[Chemical formula 38]

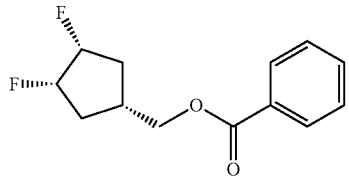

[(1α,3α,4β)-3-Fluoro-4-hydroxycyclopentyl]methyl benzoate (326 mg) was dissolved in anhydrous tetrahydrofuran (5 mL). A solution of bis(2-methoxyethyl)aminosulfur trifluoride (455 mg) in anhydrous tetrahydrofuran (2 mL) was added to the prepared mixture, and the mixture was heated to reflux under stirring for 1.5 hours. The reaction mixture was added to a saturated aqueous sodium hydrogen carbonate solution (10 mL), and the resultant solution was extracted with ethyl acetate (2×30 mL). The ethyl acetate extracts were combined, washed with saturated brine (2×10 mL), dried over anhydrous sodium sulfate, and concentrated under reduced pressure. The residue was purified by silica gel column chromatography (eluent:hexane/ethyl acetate=4:1) to give [(1α,3α,4α)-3,4-difluorocyclopentyl]methyl benzoate (233 mg).

MS (CI$^+$) m/z: 241 (MH$^+$).

HRMS (CI$^+$) for $C_{13}H_{15}F_2O_2$ (MH$^+$): calcd., 241.1040; found, 241.1043.

Fifth Step

[(1α,3α,4α)-3,4-difluorocyclopentyl]methanol

[Chemical formula 39]

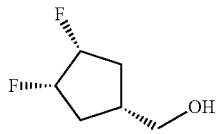

[(1α,3α,4α)-3,4-Difluorocyclopentyl]methyl benzoate (221 mg) was dissolved in ethanol (3 mL). A solution of potassium carbonate (191 mg) in water (1 mL) was added to the prepared solution, and the mixture was heated to reflux under stirring for 4 hours. The reaction mixture was concentrated under reduced pressure, and the residue was purified by silica gel column chromatography (eluent:hexane/ethyl acetate=1:2) to give [(1α,3α,4α)-3,4-difluorocyclopentyl]methanol (123 mg).

MS (CI$^+$) m/z: 137 (MH$^+$).
HRMS (CI$^+$) for C$_6$H$_{11}$F$_2$O (MH$^+$): calcd., 137.0778; found, 137.0801.

Sixth Step (1α,3α,4α)-3,4-Difluorocyclopentylmethyl iodide

[Chemical formula 40]

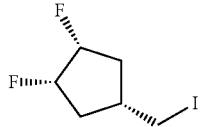

Iodine (120 mg) was added to a solution of imidazole (64.5 mg) and triphenylphosphine (124 mg) in dichloromethane (2.0 mL) under cooling with ice, and the mixture was stirred at room temperature for 30 minutes. Then, a solution of [(1α,3α,4α)-3,4-difluorocyclopentyl]methanol (43.0 mg) in dichloromethane (0.5 mL) was added to the resultant mixture, and the mixture was stirred at room temperature for 4 hours, and insoluble materials were removed by filtration. The residue obtained by concentrating the filtrate was purified by silica gel column chromatography to give (1α,3α,4α)-3,4-difluorocyclopentylmethyl iodide (28.0 mg).

MS (EI) m/z: 246 (M$^+$).
HRMS (EI) for C$_6$H$_9$F$_2$I (M$^+$): calcd., 245.9717; found, 245.9741.

Seventh Step (1α,3α,4α)-(3,4-Difluorocyclopentyl)methyltriphenylphosphonium iodide

[Chemical formula 41]

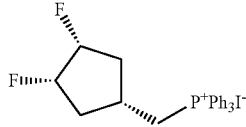

(1α,3α,4α)-(3,4-difluorocyclopentyl)methyl iodide (9.84 g), triphenylphosphine (12.6 g), and acetonitrile (3 mL) were mixed and stirred at 90 to 95° C. for 4 hours. Acetonitrile (2 mL) was further added to the reaction mixture, and the mixture was further stirred at 90 to 95° C. for 20 hours. After cooling, diethyl ether (50 mL) was added to the reaction mixture, and the precipitated crystals were collected by filtration. The collected crystals were suspended in diethyl ether (50 mL), and the suspension was filtrated to collect the crystals. The collected crystals were washed with an appropriate amount of diethyl ether and dried under reduced pressure to give the title compound (20 g).

$^1$H NMR (400 MHz, CDCl$_3$) δ 1.72-1.85 (m, 2H), 2.17-2.29 (m, 2H), 2.69-2.82 (m, 1H), 3.86 (dd, J=7.3, 2.4 Hz, 1H), 3.89 (dd, J=7.3, 2.4 Hz, 1H), 4.74-4.92 (m, 2H), 7.31-7.90 (m, 15H).

REFERENCE EXAMPLE 2

2-(5-Aminopyrazin-2-ylthio)ethanol

[Chemical formula 42]

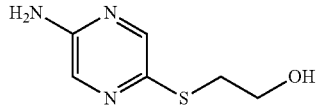

According to the method described in WO2004/052869, 2-hydroxy-1-ethanethiol (0.93 mL) and tetrakis(triphenylphosphine)palladium (3.39 g) were added to a solution of 2-amino-5-bromopyrazine (1.00 g, 5.75 mmol) in N,N-dimethylformamide (15.1 mL), and the mixture was heated and stirred at 120° C. in a sealed tube for about 3 hours. After cooling, the reaction mixture was diluted with water and extracted with a mixed solution (dichloromethane:ethanol=5:1) (100 mL×6). The organic layer was dried over anhydrous sodium sulfate and then filtrated, and the solvent was evaporated under reduced pressure. The residue was purified by column chromatography (hexane:ethyl acetate=1:1, then ethyl acetate, and then ethyl acetate:methanol=10:1) and was recrystallized (using chloroform) to give the title compound as yellow needle crystals (470 mg, yield: 44%).

MS (EI$^+$) m/z: 171 (M$^+$)
HRMS (EI$^+$) for C$_6$H$_9$N$_3$OS (M$^+$): calcd., 171.0466; found, 171.0451.

REFERENCE EXAMPLE 3

5-[2-(Methylthio)ethoxy]pyrazin-2-amine

[Chemical formula 43]

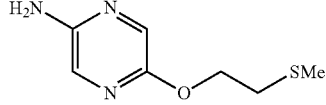

According to the method described in WO2007007886, sodium hydride (50% oily product) (314 mg) was added to methylthioethanol (7.88 mL) under cooling with ice and stirring, and then copper (490 mg) and 2-amino-5-bromopyrazine (1.00 g) were added thereto. The reaction mixture was placed in an autoclave and heated and stirred at 160° C. for about 5 hours. After cooling, the reaction mixture was diluted with water (50 mL) and ethyl acetate (50 mL), and 25% aqueous ammonia (2 mL) was added to the mixture to make it basic. The reaction mixture was filtrated through Celite, and the organic layer and the aqueous layer were separated. The aqueous layer was extracted with ethyl acetate (50 mL×2), and the extracts and the organic layer were combined, dried over anhydrous sodium sulfate, and filtrated. The solvent was evaporated under reduced pressure. The residue was purified by silica gel chromatography (hexane:ethyl acetate=1:1) and then by preparative TLC (chloroform:methanol=10:1, then NH silica gel, hexane:acetone=3:1) to give the title compound as white powder crystals (59.2 mg, yield: 6%).

MS (EI$^+$) m/z: 185 (M$^+$).

HRMS (EI$^+$) for $C_7H_{11}N_3OS$ (M$^+$): calcd., 185.0623; found, 185.0613.

REFERENCE EXAMPLE 4

5-(2-Ethoxyethoxy)pyrazin-2-amine

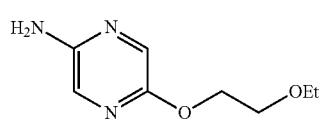

[Chemical formula 44]

According to the method described in Reference Example 3, the title compound was obtained as yellow crystals (1.50 g, yield: 41%) from 2-amino-5-bromopyrazine (3.48 g) and ethoxyethanol (36.0 g).

MS (EI$^+$) m/z: 183 (M$^+$)

HRMS (EI$^+$) for $C_8H_{13}N_3O_2$(M$^+$): calcd., 183.1008; found, 183.0996

REFERENCE EXAMPLE 5

5-(3-Methoxypropoxy)pyrazin-2-amine

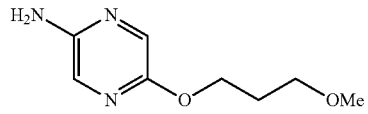

[Chemical formula 45]

According to the method described in Reference Example 3, the title compound was obtained as yellow crystals (644 mg, yield: 18%) from 2-amino-5-bromopyrazine (3.48 g) and methoxypropanol (18.0 g).

MS (EI$^+$) m/z: 183 (M$^+$).

HRMS (EI$^+$) for $C_8H_{13}N_3O_2$(M$^+$): calcd., 183.1008; found, 183.1011.

REFERENCE EXAMPLE 6

5-[2-(Dimethylamino)ethoxy]pyrazin-2-amine

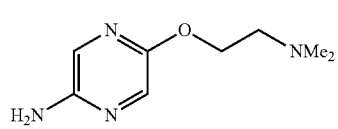

[Chemical formula 46]

According to the method described in Reference Example 3, the title compound was obtained as a yellow oil (121 mg, yield: 23%) from 2-amino-5-bromopyrazine (500 mg) and 2-(dimethylamino)ethanol (2.56 g).

MS (CI) m/z: 183 (MH$^+$).

HRMS (CI) for $C_8H_{15}N_4O$ (MH$^+$): calcd., 183.1246; found, 183.1242.

$^1$H NMR (400 MHz, CDCl$_3$) δ 2.33 (s, 6H), 2.70 (t, J=5.8 Hz, 2H), 4.12 (brs, 2H), 4.31 (t, J=5.8 Hz, 2H), 7.53 (d, J=1.2 Hz, 1H), 7.80 (d, J=1.2 Hz, 1H).

IR (ATR): 1280, 1630, 3330 cm$^{-1}$.

REFERENCE EXAMPLE 7

5-[2-Methyl-2-(tetrahydro-2H-pyran-2-yloxy)propoxy]pyrazin-2-amine

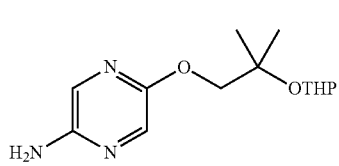

[Chemical formula 47]

According to the method described in Reference Example 3, the title compound was obtained as brown powder crystals (60 mg, yield: 13%) from 2-amino-5-bromopyrazine (299 mg) and 2-methyl-2-[(tetrahydro-2H-pyran-2-yl)oxy]-1-propanol (1.50 g).

MS (CI) m/z: 268 (MH$^+$).

HRMS (CI) for $C_{13}H_{22}N_3O_3$ (MH$^+$): calcd., 268.1661; found, 268.1645.

$^1$H NMR (400 MHz, CDCl$_3$) δ 1.35 (s, 6H), 1.46-1.52 (m, 4H), 1.59-1.72 (m, 1H), 1.76-1.88 (m, 1H), 3.43 (td, J=8.3, 4.3 Hz, 1H), 3.94 (ddd, J=11.6, 5.2, 3.7 Hz, 1H), 4.11 (d, J=10.4 Hz, 1H), 4.16 (d, J=10.4 Hz, 1H), 4.21 (s, 2H), 4.88 (q, J=2.9 Hz, 1H), 7.54 (d, J=1.8 Hz, 1H), 7.79 (d, J=1.8 Hz, 1H).

IR (ATR): 1620, 1487, 1379 cm$^{-1}$.

REFERENCE EXAMPLE 8

1-[2-(Dimethylamino)-2-methylpropyl]-1H-pyrazol-3-amine

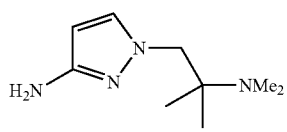

[Chemical formula 48]

Sodium hydride (156 mg) was added to a solution of 3-nitro-1H-pyrazole (196 mg) in anhydrous DMF (2 mL) under cooling with ice, and the mixture was stirred at room temperature for 15 minutes. A solution of 1-chloro-N,N,2-trimethylpropan-2-amine in DMF (0.52 mL) was added to the resultant mixture, and the mixture was stirred at room temperature for about 24 hours. A saturated aqueous ammonium chloride solution (25 mL) and ethyl acetate (25 mL) were added to the reaction mixture and stirred under cooling with ice. The organic layer was separated, washed with saturated brine (100 mL), dried over anhydrous sodium sulfate, and filtrated, and the filtrate was concentrated under reduced pressure. The obtained residue was purified by silica gel column chromatography (neutral spherical silica gel, ethyl acetate: hexane=1:1) to give N,N,2-trimethyl-1-(3-nitro-1H-pyrazol-1-yl)propan-2-amine as yellow powder crystals (90.9 mg, yield: 25%).

MS (CI) m/z: 213 (MH$^+$).

HRMS (CI) for C$_9$H$_{17}$N$_4$O$_2$ (MH$^+$): calcd, 213.1352; found, 213.1314.

N,N,2-trimethyl-1-(3-nitro-1H-pyrazol-1-yl)propan-2-amine (70.6 mg) was dissolved in a mixed solution (ethanol-ethyl acetate, 4:1, 5 mL). Then, 10% palladium-carbon (7 mg) was added to the prepared solution, and the solution was subjected to catalytic reduction at 101 kPa for about 2 hours. The reaction mixture was filtrated through Celite, and the filtrate was evaporated under reduced pressure. The obtained residue was purified by silica gel column chromatography (silica gel NH, ethyl acetate:hexane=1:1) to give the title compound as a yellow oil (56.8 mg, yield: 94%).

MS (CI) m/z: 183 (MH$^+$).

HRMS (CI) for C$_9$H$_{14}$N$_4$ (MH$^+$): calcd., 183.1610; found, 183.1615.

$^1$H NMR (400 MHz, CDCl$_3$) δ 1.50 (s, 6H), 2.03 (s, 6H), 2.53 (s, 2H), 3.59 (s, 2H), 5.56 (d, J=2.4 Hz, 1H), 7.28 (d, J=2.4 Hz, 1H).

IR (ATR): 1617, 1541, 1492 cm$^{-1}$.

REFERENCE EXAMPLE 9

5-(2-Bromoethylthio)thiazol-2-amine

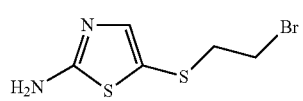

[Chemical formula 49]

Triphenylphosphine (12.1 g), imidazole (3.86 g), and carbon tetrabromide (4.44 g) were added to a suspension of 5-(2-hydroxyethylthio)thiazol-2-amine (2.00 g) in methylene chloride (74.6 mL) under cooling with ice, and the mixture was stirred under cooling with ice for 4 hours. Methylene chloride (200 mL) and water (100 mL) were added to the reaction mixture, and the mixture was extracted. The organic layer was washed with saturated brine (100 mL), dried over anhydrous sodium sulfate, and filtrated, and the filtrate was concentrated under reduced pressure. The obtained residue was purified by silica gel column chromatography (neutral spherical silica gel, ethyl acetate:hexane=1:10 and then 1:2) and washed with hexane to give the title compound as white powder crystals (1.06 g, yield: 39%).

MS (EI) m/z: 238 (M$^+$).

HRMS (EI) for C$_5$H$_7$BrN$_2$S$_2$ (M$^+$): calcd, 237.9234; found, 237.9212.

REFERENCE EXAMPLE 10

5-(3-Bromopropylthio)thiazol-2-amine

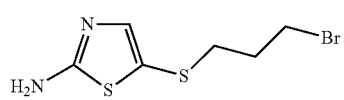

[Chemical formula 50]

According to the method described in Reference Example 9, the title compound was obtained as a yellow oil (450 mg, yield: 7%) from 5-(3-hydroxypropylthio)thiazol-2-amine (5.00 g).

MS (ESI) m/z: 253 (MH$^+$).

HRMS (ESI) for C$_6$H$_{10}$BrN$_2$S$_2$ (M$^+$): calcd, 252.94688; found, 252.94629.

REFERENCE EXAMPLE 11

5-[2-(4-Methylpiperazin-1-yl)ethylthio]thiazol-2-amine

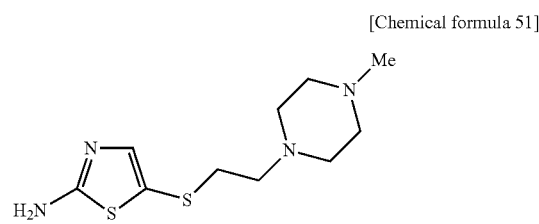 [SMILES: CN1CCN(CCSc2cnc(N)s2)CC1]

[Chemical formula 51]

1-Methylpiperazine (3.47 mL) was added to the compound obtained in Reference Example 9 (150 mg), and the mixture was heated and stirred at 60° C. for 2 hours. After cooling, the reaction mixture was concentrated under reduced pressure. Methylene chloride (10 mL) and a saturated aqueous sodium hydrogen carbonate solution (10 mL) were added to the residue, and the mixture was extracted. The extraction was repeated twice, and the combined organic layers were washed with saturated brine (7 mL), dried over anhydrous sodium sulfate, filtrated, and evaporated under reduced pressure. The obtained amorphous was washed with diisopropyl ether to give the title compound as white powder crystals (137 mg, yield: 84%).

Melting point 106-108° C.

EIMS m/z: 258 (M$^+$).

HRMS (EI) for C$_{10}$H$_{18}$N$_4$S$_2$ (M$^+$): calcd., 258.0973; found, 258.0978.

$^1$H NMR (400 MHz, CDCl$_3$) δ 2.28 (s, 3H), 2.35-2.57 (m, 8H), 2.61 (dd, J=8.0, 4.3 Hz, 2H), 2.77 (dd, J=8.0, 4.3 Hz, 2H), 4.95 (s, 2H), 7.09 (s, 1H).

IR (ATR): 1653, 1527, 1485 cm$^{-1}$.

REFERENCE EXAMPLE 12

(S)-5-[2-(3-Fluoropyrrolidin-1-yl)ethylthio]thiazol-2-amine

[Chemical formula 52]

According to the method described in Reference Example 11, the title compound was obtained as white powder crystals (82.3 mg, yield: 40%) from the compound obtained in Reference Example 9 (200 mg), (S)-3-fluoropyrrolidine hydrochloride (210 mg), and triethylamine (0.50 mL).

Melting point 144-145° C.

[α]$_D^{24}$ −4° (c0.41, DMSO)

EIMS m/z: 247 (M$^+$).

HRMS (EI) for $C_9H_{14}FN_3S_2$ (M+): calcd, 247.0613; found, 247.0646.

1H NMR (400 MHz, CDCl3) δ 1.94-2.22 (m, 2H), 2.42-2.51 (m, 1H), 2.70-2.91 (m, 7H), 4.99 (s, 2H), 5.06-5.25 (m, 1H), 7.10 (s, 1H).

IR (ATR): 1649, 1533, 1491 cm−1.

REFERENCE EXAMPLE 13

(R)-5-[2-(3-Fluoropyrrolidin-1-yl)ethylthio]thiazol-2-amine

[Chemical formula 53]

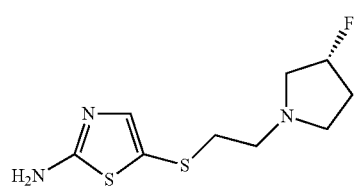

According to the method described in Reference Example 11, the title compound was obtained as white powder crystals (98.8 mg, yield: 48%) from the compound obtained in Reference Example 9 (200 mg), (R)-3-fluoropyrrolidine hydrochloride (210 mg), and triethylamine (0.50 mL).

Melting point 147° C.

$[\alpha]_D^{23}$ +3° (c0.43, DMSO)

EIMS m/z: 247 (M+).

1H NMR (400 MHz, CDCl3)

HRMS (EI) for $C_9H_{14}FN_3S_2$ (M+): calcd., 247.0613; found, 247.0622. 67 1.94-2.22 (m, 2H), 2.42-2.51 (m, 1H), 2.70-2.91 (m, 7H), 4.99 (s, 2H), 5.06-5.25 (m, 1H), 7.10 (s, 1H).

IR (ATR): 1649, 1533, 1491 cm−1.

REFERENCE EXAMPLE 14

5-[2-(4,4-Difluoropiperidin-1-yl)ethylthio]thiazol-2-amine

[Chemical formula 54]

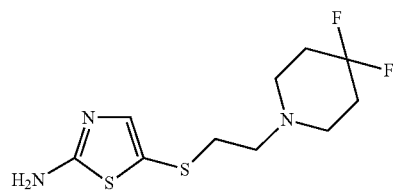

According to the method described in Reference Example 11, the title compound was obtained as white powder crystals (68.9 mg, yield: 30%) from the compound obtained in Reference Example 9 (200 mg), 4,4-difluoropiperidine hydrochloride (263 mg), and triethylamine (0.50 mL).

Melting point 127° C. (diisopropyl ether)

EIMS m/z: 279 (M+).

HRMS (EI) for $C_{10}H_{15}F_2N_3S_2$ (M+): calcd., 279.0675; found, 279.0679.

1H NMR (400 MHz, CDCl3) δ 1.93-2.06 (m, 4H), 2.56 (t, J=5.5 Hz, 4H), 2.64 (dd, J=8.9, 5.8 Hz, 2H), 2.76 (dd, J=8.9, 5.8 Hz, 2H), 5.21 (s, 2H), 7.08 (s, 1H).

IR (ATR): 1609, 1519, 1478 cm−1.

REFERENCE EXAMPLE 15

1-[2-(2-Aminothiazol-5-ylthio)ethyl]piperidine-4-carboxylic acid ethyl ester

[Chemical formula 55]

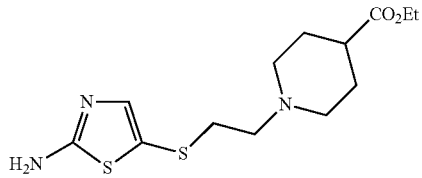

According to the method described in Reference Example 11, the title compound was obtained as white powder crystals (150 mg, yield: 76%) from the compound obtained in Reference Example 9 (150 mg) and piperidine-4-carboxylic acid ethyl ester (4.83 mL). Melting point 80-81° C.

MS (CI) m/z: 316 (MH+).

HRMS (CI) for $C_{13}H_{22}N_3O_2S_2$ (MH+): calcd., 316.1153; found, 316.1141.

1H NMR (400 MHz, CDCl3) δ 1.25 (t, J=7.1 Hz, 3H), 1.68-1.80 (m, 2H), 1.82-1.92 (m, 2H), 2.04-2.10 (m, 2H), 2.21-2.31 (m, 1H), 2.55-2.59 (m, 2H), 2.75-2.80 (m, 2H), 2.80-2.88 (m, 2H), 4.13 (q, J=7.1 Hz, 2H), 5.00 (s, 2H), 7.08 (s, 1H).

IR (ATR): 1707, 1524, 1448 cm−1.

REFERENCE EXAMPLE 16

(S)-[1-[2-(2-Aminothiazol-5-ylthio)ethyl]pyrrolidin-2-yl]methanol

[Chemical formula 56]

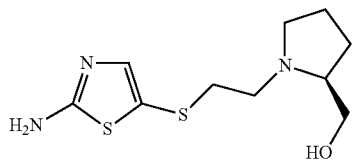

According to the method described in Reference Example 11, the title compound was obtained as white powder crystals (130 mg, yield: 80%) from the compound obtained in Reference Example 9 (150 mg) and (S)-pyrrolidin-2-ylmethanol (3.10 mL).

Melting point 98-99° C.

$[\alpha]_D^{24}$ −90° (c0.54, CHCl3).

MS (CI) m/z: 260 (MH+).

HRMS (CI) for $C_{10}H_{18}N_3OS_2$ (MH+): calcd., 260.0891; found, 260.0892.

1H NMR (400 MHz, CDCl3) δ 1.70-1.95 (m, 4H), 2.27 (q, J=8.6 Hz, 1H), 2.53-2.60 (m, 1H), 2.60-2.68 (m, 1H), 2.75-2.83 (m, 2H), 2.90-2.97 (m, 1H), 3.14-3.20 (m, 1H), 3.38 (dd, J=11.0, 2.4 Hz, 1H), 3.62 (dd, J=11.0, 3.7 Hz, 1H), 4.96 (s, 2H), 7.12 (s, 1H).

IR (ATR): 3161, 1516, 1498 cm−1.

REFERENCE EXAMPLE 17

5-[2-[cis-3,4-Difluoropyrrolidin-1-yl]ethylthio]thiazol-2-amine

[Chemical formula 57]

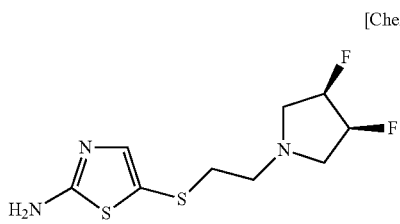

According to the method described in Reference Example 11, the title compound was obtained as white powder crystals (35.0 mg, yield: 19%). More specifically, the compound obtained in Reference Example 9 (200 mg), cis-3,4-difluoropyrrolidine hydrochloride (100 mg), and diisopropylamine (141 mg) were used for the reaction, and potassium iodide (12 mg) was added during the reaction.

MS (CI) m/z: 266 (MH$^+$).

HRMS (CI) for $C_9H_{14}F_2N_3S_2$ (MH$^+$): calcd., 266.0597; found, 266.0577.

$^1$H NMR (400 MHz, CDCl$_3$) δ 2.71-2.80 (m, 4H), 2.81-2.94 (m, 2H), 3.04-3.14 (m, 2H), 4.89-5.12 (m, 2H), 5.00 (s, 2H), 7.09 (s, 1H). IR (ATR): 1645, 1530, 1490 cm$^{-1}$.

REFERENCE EXAMPLE 18

5-[2-(cis-2,2-Dimethyltetrahydro-5H-1,3-dioxolo[4,5-C]pyrrol-5-yl)ethylthio]thiazol-2-amine

[Chemical formula 58]

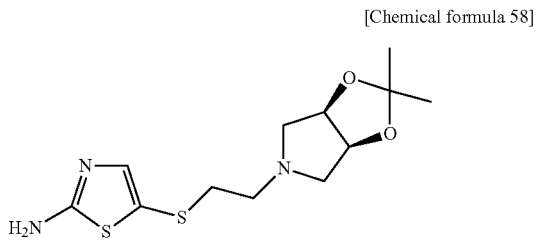 [SMILES: CC1(C)O[C@H]2CN(CCSc3cnc(N)s3)C[C@H]2O1]

According to the method described in Reference Example 11, the title compound was obtained as white powder crystals (127 mg, yield: 30%) from the compound obtained in Reference Example 9 (330 mg) and cis-2,2-dimethyltetrahydro-5H-1,3-dioxolo[4,5-c]pyrrole (280 mg).

MS (ESI) m/z: 302 (MH$^+$).

HRMS (ESI) for $C_{12}H_{20}N_3O_2S_2$ (MH$^+$): calcd., 302.09969; found, 302.09926.

$^1$H NMR (400 MHz, CDCl$_3$) δ 1.31 (s, 3H), 1.52 (s, 3H), 2.10-2.17 (m, 2H), 2.62-2.66 (m, 2H), 2.74-2.78 (m, 2H) 3.06 (d, J=11.6 Hz, 2H), 4.62-4.65 (m, 2H), 4.96 (s, 2H), 7.08 (s, 1H).

IR (ATR): 1644, 1513, 1483 cm$^{-1}$.

REFERENCE EXAMPLE 19

(S)-1-[2-(2-Aminothiazol-5-ylthio)ethyl]pyrrolidine-2-carboxylic acid methyl ester

[Chemical formula 59]

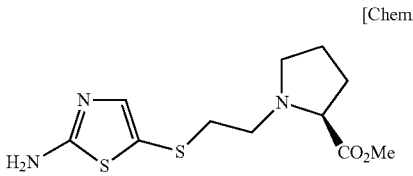

According to the method described in Reference Example 11, the title compound was obtained as a yellow oil (85.7 mg, yield: 36%) from the compound obtained in Reference Example 9 (200 mg), (S)-pyrrolidine-2-carboxylic acid methyl ester hydrochloride (277 mg), and triethylamine (0.50 mL).

$[α]_D^{25}$ −85° (c0.25, CHCl$_3$).

MS (CI) m/z: 288 (MH$^+$).

HRMS (CI) for $C_{11}H_{18}N_3O_2S_2$ (MH$^+$): calcd., 288.0840; found, 288.0837.

$^1$H NMR (400 MHz, DMSO-d$_6$) δ 1.74-1.87 (m, 1H), 1.87-2.00 (m, 2H), 2.04-2.18 (m, 1H), 2.41 (q, J=8.2 Hz, 1H), 2.66-2.72 (m, 1H), 2.77 (dd, J=7.9, 6.7 Hz, 2H), 2.90-2.96 (m, 1H), 3.15 (td, J=8.3, 3.1 Hz, 1H), 3.23 (dd, J=8.6, 5.5 Hz, 1H), 3.71 (s, 3H), 5.00 (s, 2H), 7.10 (s, 1H).

IR (ATR): 3293, 3124, 2949, 2815, 1732, 1517, 1484 cm$^{-1}$.

REFERENCE EXAMPLE 20

(S)-1-[2-(2-Aminothiazol-5-ylthio)ethyl]pyrrolidine-2-carboxylic acid ethyl ester

[Chemical formula 60]

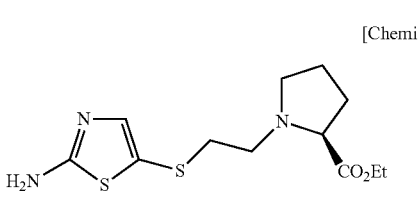

According to the method described in Reference Example 11, the title compound was obtained as a yellow oil (580 mg, yield: 58%) from the compound obtained in Reference Example 9 (800 mg), (S)-pyrrolidine-2-carboxylic acid ethyl ester hydrochloride (15 g), and isopropylamine (9.00 g).

$[α]_D^{25}$ −61° (c0.28, CHCl$_3$).

MS (CI) m/z: 302 (MH$^+$).

HRMS (CI) for $C_{12}H_{20}N_3O_2S_2$ (MH$^+$): calcd., 302.0997; found, 302.1012.

$^1$H NMR (400 MHz, DMSO-d$_6$) δ 1.27 (t, J=6.7 Hz, 3H), 1.74-1.85 (m, 1H), 1.85-2.00 (m, 2H), 2.05-2.18 (m, 1H), 2.38-2.48 (m, 1H), 2.66-2.72 (m, 1H), 2.77 (t, J=7.3 Hz, 2H), 2.90-2.97 (m, 1H), 3.13-3.22 (m, 2H), 4.17 (qd, J=7.3, 1.2 Hz, 2H), 5.35 (s, 2H), 7.07 (s, 1H).

IR (ATR): 1728, 1619, 1517 cm$^{-1}$.

REFERENCE EXAMPLE 21

5-[3-(Dimethylamino)propylthio]thiazol-2-amine

[Chemical formula 61]

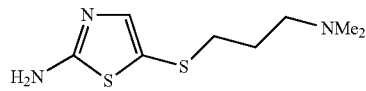

According to the method described in Reference Example 11, the title compound was obtained as colorless powder crystals (53.5 mg, yield: 62%) from the compound obtained in Reference Example 10 (100 mg) and dimethylamine (a 2M methanol solution, 9.90 mL).

MS (APCI) m/z: 216 (MH$^+$).

HRMS (APCI) for $C_8H_{14}N_3S_2$ calcd., 216.06291; found, 216.06354.

$^1$H NMR (400 MHz, CDCl$_3$) δ 1.72-1.79 (m, 2H), 2.20 (s, 6H), 2.35 (t, J=7.3 Hz, 2H), 2.68 (t, J=7.3 Hz, 2H), 5.26 (s, 2H), 7.07 (s, 1H).

IR (ATR): 1647, 1514, 1493 cm$^{-1}$.

REFERENCE EXAMPLE 22

Ethyl (Z)-3-(1α,3α,4α)-3,4-(difluorocyclopentyl)acrylate

[Chemical formula 62]

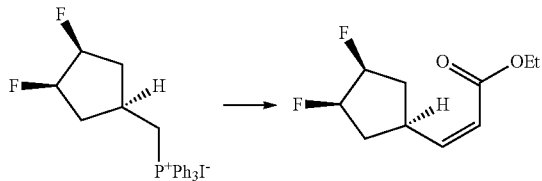

Lithium bis(trimethylsilyl)amide (a 1 mol/L tetrahydrofuran solution, 41.1 mL. 41.1 mmol) was added in an argon atmosphere at 4° C. to a solution of the [(1α,3α,4α)-(3,4-difluorocyclopentyl)methyl]triphenylphosphonium iodide (20.3 g, 40 mmol) synthesized in Reference Example 1 in anhydrous tetrahydrofuran (70 mL), and the resultant mixture was stirred for 1 hour at about the same temperature. Next, a solution of ethyl glyoxylate (4.24 g, 41.5 mmol) in anhydrous tetrahydrofuran (50 mL) was added at 4° C., and the resultant mixture was stirred at room temperature for 24 hours. Next, water (20 mL) was added at 4° C., then 1 mol/L hydrochloric acid aqueous solution was added, and the organic layer was concentrated under reduced pressure. The obtained residue was extracted with ethyl acetate. The organic layer was washed with saturated brine. The washed organic layer was dried over anhydrous sodium sulfate, and then concentrated under reduced pressure. The obtained residue was isolated and purified by silica gel column chromatography (ethyl acetate:hexane=1:4) to give 5.25 g of the title compound as a pale yellow oily substance.

MS (EI$^+$) m/z: 204 (M$^+$).

HRMS (EI$^+$) for $C_{10}H_{14}F_2O_2$ (M$^+$): calcd., 204.0962; found, 204.0942.

$^1$H NMR (400 MHz, CDCl$_3$) δ1.29 (t, J=7.1 Hz, 3H), 1.74-1.90 (m, 2H), 2.26-2.42 (m, 2H), 3.84-3.98 (m, 1H), 4.16 (q, J=7.1 Hz, 2H), 4.80-4.90 (m, 1H), 4.92-5.02 (m, 1H), 5.74 (dd, J=11.6, 1.2 Hz, 1H), 6.22 (dd, J=11.0, 9.8 Hz, 1H).

REFERENCE EXAMPLE 23

Ethyl (Z)-2-bromo-3-[(1α,3α,4α)-3,4-difluorocyclopentyl]acrylate

[Chemical formula 63]

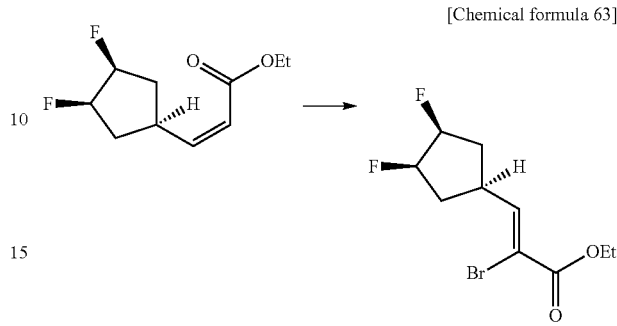

Bromine (1.19 mL, 23.2 mmol) was added in an argon atmosphere at −6° C. to a solution of the compound (5.00 g, 24.5 mmol) of Reference Example 22 in carbon tetrachloride (15 mL), and the resultant mixture was then stirred for 7 hours at room temperature. The reaction mixture was concentrated under reduced pressure, and anhydrous dichloromethane (40 mL) was added to the obtained residue. Next, in an argon atmosphere, triethylamine (4.10 mL, 29.4 mmol) was added at 4° C., and the resultant mixture was stirred for 12 hours at room temperature. Water was added to the reaction mixture, whereby separate layers formed. Then, the aqueous layer was extracted with dichloromethane, and the obtained organic layers are collected. The combined mixture was washed with 1 mol/L hydrochloric acid aqueous solution, and then washed with saturated brine. The washed mixture was dried over anhydrous sodium sulfate, and then concentrated under reduced pressure. The obtained residue was isolated and purified by silica gel column chromatography (ethyl acetate:hexane=1:5) to give 7.33 g of the title compound as a colorless oily substance.

MS (EI$^+$) m/z: 282 (M$^+$).

HRMS (EI$^+$) for $C_{10}H_{13}BrF_2O_2$ (MH$^+$): calcd., 282.0067; found, 282.0081.

$^1$H NMR (400 MHz, CDCl$_3$) δ1.34 (t, J=7.3 Hz, 3H), 1.86-2.02 (m, 2H), 2.28-2.44 (m, 2H), 3.08-3.20 (m, 1H), 4.29 (q, J=7.3 Hz, 2H), 4.84-4.94 (m, 1H), 4.96-5.06 (m, 1H), 7.29 (d, J=9.2 Hz, 1H).

REFERENCE EXAMPLE 24

Ethyl (E)-3-[(1α,3α,4α)-3,4-difluorocyclopentyl]-2-[4-(methylsulfonyl)phenyl]acrylate

[Chemical formula 64]

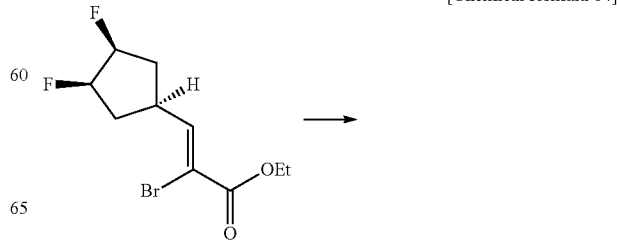

-continued

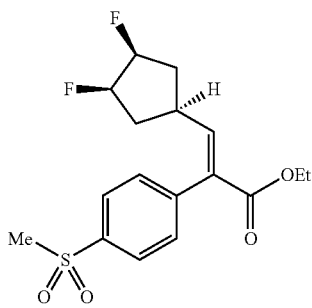

Pinacolato diboron (88.0 mg, 0.35 mmol), 1,1-bis(diphenylphosphino)ferrocene-palladium(II) dichloride (8 mg), and potassium acetate (98.0 mg, 1.00 mmol) were added to a solution of 4-bromomethylsulfonylbenzene (79.0 mg, 0.33 mmol) in dimethylformamide (1 mL), and the resultant mixture was stirred in an argon atmosphere for 80 minutes at 120° C. Next, ethyl (Z)-2-bromo-3-[(1α,3α,4α)-3,4-difluorocyclopentyl]acrylate (100.0 mg, 0.33 mmol), 1,1-bis(diphenylphosphino)ferrocene-palladium(II) dichloride (10 mg), and 2 mol/L sodium carbonate aqueous solution (1 mL) were added, and the resultant mixture was stirred in an argon atmosphere for 2 hours at 80° C. Water was added to the reaction mixture. Extraction was carried out with ethyl acetate, and the organic layer was washed with water and then saturated brine. The washed organic layer was dried over anhydrous sodium sulfate, and then concentrated under reduced pressure. The obtained residue was isolated and purified by silica gel column chromatography (ethyl acetate:hexane=1:1) to give 39.3 g of the title compound.

REFERENCE EXAMPLE 25

(E)-3-[(1β,3α,4α)-3,4-difluorocyclopentyl]-2-[4-(methylsulfonyl)phenyl]-N-(thiozol-2-yl)acrylamide (Comparative Compound 1)

[Chemical formula 65]

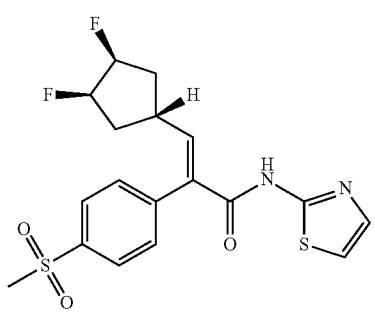

Using the [(1β,3β,4β)-3,4-dihydroxycyclopentyl]methyl benzoate obtained in the first step of Reference Example 1, the same reactions as in the second to seventh steps of Reference Example 1 were carried out to synthesize (1β,3α,4α)-(3,4-difluorocyclopentyl)methyltriphenylphosphonium iodide. Further, the conversions of from Example 1 to Example 5 were carried out to obtained the title compound.

REFERENCE EXAMPLE 26

(E)-3-[(3α,4β)-3,4-difluorocyclopentyl]-2-[4-(methylsulfonyl)phenyl]-N-(thiozol-2-yl)acrylamide (Comparative Compound 2), and (E)-3-[(3β,4α)-3,4-difluorocyclopentyl]-2-[4-(methylsulfonyl)phenyl]-N-(thiozol-2-yl)acrylamide (Comparative Compound 3)

[Chemical formula 66]

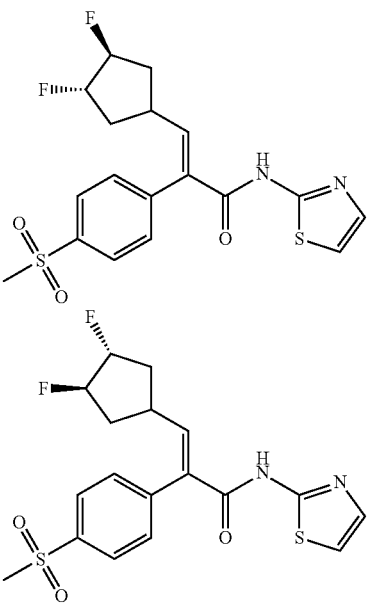

Using the [(1α,3α,4β)-3-fluoro-4-hydroxycyclopentyl] methyl benzoate obtained in the third step of Reference Example 1, stereoinversion based on a Mitsunobu reaction of a hydroxyl group was carried out, followed by the same fluorination as in the fourth step of Reference Example 1. Then, the resultant product underwent hydrolysis of the ester group, and oxidation of the hydroxymethyl group to convert the product into a carboxylic acid. This carboxylic acid was condensed with (S)-4-phenyloxazolidinone, the diastereomer was then separated, the asymmetric auxiliary group was removed, the resultant product was then reduced to methanol compound, and the reactions of from the sixth and subsequent steps of Reference Example 1 were carried out in order to obtain the title compound.

TEST EXAMPLE 1

GK Activity Measurement

The GK activity was determined not by direct measurement of the amount of glucose-6-phosphate produced by the enzyme reaction but by measurement of the amount of NADH produced by a glucose-6-dehydrogenase-coupled reaction.

(Preparation of Recombinant GK)

Cloning of Human Hepatic GK and Human Pancreas GK and Acquisition of Recombinant Proteins Based on a human hepatic GK sequence available from GeneBank (Accession Number: NM_033507) and a human pancreas GK sequence (Accession Number: NM_000162), PCR cloning was performed using Pyrobest DNA Polymerase (product of Takara Bio Inc.) with human hepatic cDNA (product of Clontech Laboratories, Inc.) and human pancreas cDNA (product of Clontech Laboratories, Inc.) used as templates. The enzymes were expressed in a soluble form in E. coli as His-tagged fusion proteins (tagged with six His residues at the C-terminus. The E. coli cells were sonicated and centrifuged, and the supernatant was collected. The collected supernatant was purified by metal chelate affinity chromatography.

After purification, the enzymes were stored in 12.5 mM HEPES (pH 7.3), 75 mM KCl, 0.5 mM $MgCl_2$, 0.5 mM DTT, 2.5 mM glucose, and 50% glycerol at −80° C.

(Measurement of GK Activity)

The assay was performed at 25° C. using a half-area flat-bottom 96-well plate (product of Costar). The incubation mixture was prepared such that the final mixture contained a 25 mM HEPES buffer solution (pH 7.1) (product of Invitrogen Corporation), 25 mM KCl (product of Wako Pure Chemical Industries, Ltd.), 2 mM $MgCl_2$ (product of Wako Pure Chemical Industries, Ltd.), 5 mM D-glucose (product of Wako Pure Chemical Industries, Ltd.), 1 mM ATP (product of Roche), 1 mM NAD (product of Sigma), 1 mM dithiothreitol (product of Wako Pure Chemical Industries, Ltd.), 5 Unit/mL G6PDH (product of Sigma), 0.1% BSA (product of Sigma), GK, and a test compound or 5% DMSO.

The test compound was dissolved in DMSO in advance, and 2 μL of the prepared solution was added to 20 μL of a solution containing the HEPES buffer solution (pH 7.1), KCl, $MgCl_2$, D-glucose, ATP, NAD, and dithiothreitol. Subsequently, 18 μL of a solution containing the G6PDH, BSA, and recombinant GK was added to the mixture to initiate the reaction. The GK was added such that an increase in absorbance per minute in the presence of 5% DMSO was between 0.002 to 0.003. After the reaction was initiated, the increase in absorbance at 340 nm was measured for 15 minutes using a SPECTRAmax 190 microplate spectrophotometer (product of Molecular Devices Corporation), and the activity was evaluated using the increase in the first 10 minutes.

When the compounds 1A, 26A, 27A, 31A, 44A, 49A, 1B, 2B, 4B, 31B, 38B, 41B, 53B, 21B, and 26B of the present invention were added in an amount of 10 μM, the effect of activating the human hepatic GK was found to be 200% or more that of a well not containing the compounds. Especially, in the compound 1A of the present invention, $EC_{50}$ was shown to be 1 μM or less. On the other hand, in the comparative compound 1-3, each $EC_{50}$ found to be more than 10 μM.

TEST EXAMPLE 2

Hypoglycemia Activity Test

The effects of the test compounds on blood glucose levels were measured using ICR mice (male, 7 to 9 weeks of age, Charles River Laboratories Japan, Inc.). Each of the compounds was dissolved in a mixture of Gelucire 44/14 (trade name, product of Gattefosse) and PEG 400 (60:40), and was orally administered to the animal after 2-hour fasting period (30 mg/kg, 10 mL/kg). Blood was collected from the caudal vein immediately before the administration (Pre value) and 0.5, 2, and 4 hours after the administration using a blood-collecting tube coated with dipotassium ethylenediaminetetraacetate and was centrifuged (4° C., 3,600×g, 3 minutes) to obtain a plasma sample.

Each sample was diluted five-fold with physiological saline, and the blood glucose level was measured using Glucose CII-Test Wako (trade name, product of Wako Pure Chemical Industries, Ltd.). More specifically, the samples and a glucose standard solution (100 mg/dL) (obtained by diluting a glucose standard solution (200 mg/dL) two-fold with physiological saline) were placed in the wells of a flat-bottom 96-well plate in an amount of 10 μL/well, and 150 μL of a color reagent was added to each well. The plate was left to stand at 37° C. for 5 minutes to allow color development. The measurement of OD at 505 nm was performed using En Vision 2103 Multilabel Reader (trade name, product of PerkinElmer Inc.). The reduction ratio of the blood glucose level at each sampling point relative to the Pre value was determined, and a glucose reduction ratio (the average of the determined reduction ratios) was computed.

In the compounds 1A, 26A, 27A, 31A, 44A, 1B, 2B, 11B, 12B, 21B, 26B, 62A, 31B, 79B, 103B, 108B, 4B, 38B, 53B, 46A, 58A, and 41B of the present invention, the glucose reduction ratio was found to be 35% or more. Especially, in the compound 1A of the present invention, the reduction ratio was shown to be 50% or more. On the other hand, in the comparative compound 1-3, the each reduction ratio found to be less than 30%.

TEST EXAMPLE 3

Dosage Dependence of Hypoglycemia and Insulin Secretion Promotion Tests

The effects of the test compounds on blood glucose levels and insulin secretion were measured using ICR mice (male, 7 to 9 weeks of age, Charles River Laboratories Japan, Inc.). Each of the compounds was dissolved in a mixture of Gelucire 44/14 (trade name, product of Gattefosse) and PEG 400 (60:40), and was orally administered to the animal after a 2-hour fasting period (30 mg/kg, 10 mL/kg). Blood was collected from the caudal vein immediately before the administration (Pre value) and 0.5, 1, 2, and 4 hours after the administration using a blood-collecting tube coated with dipotassium ethylenediaminetetraacetate and was centrifuged (4° C., 3,600×g, 3 minutes) to obtain a plasma sample.

Each sample was diluted five-fold with physiological saline, and the blood glucose level was measured using Glucose CII-Test Wako (trade name, product of Wako Pure Chemical Industries, Ltd.). More specifically, the samples, physiological saline, and a glucose standard solution (100 mg/dL) (obtained by diluting a glucose standard solution (200 mg/dL) two-fold with physiological saline) were placed in the wells of a flat-bottom 96-well plate in an amount of 10 μL/well, respectively, and 150 μL of a color reagent was added to each well. The plate was left to stand at 37° C. for 5 minutes to allow color development. The measurement of OD at 505 nm was performed using En Vision 2103 Multi label Reader (trade name, product of PerkinElmer Inc.). The glucose area under the curve$_{0.5\text{-}4\ hr}$ (Glucose AUC$_{0.5\text{-}4\ hr}$) was calculated from the blood glucose level at each blood collection point.

The insulin concentration was measured using an undiluted solution of each sample with a Morinaga insulin measurement kit (trade name, product of Morinaga Institute of Biological Science Inc.). The insulin area under the curve$_{0.5\text{-}4\ hr}$ (Insulin AUC$_{0.5\text{-}4\ hr}$) was calculated from the insulin level at each blood collection point.

TEST EXAMPLE 4

Effects on Abnormal Glucose Tolerance of Severe Diabetes db/db Mice

The effects on the abnormal glucose tolerance of severe diabetes db/db mice were tested by a method based on the Fyfe method (Diabetologia. 2007 June; 50 (6): 1277-87). The effects of the test compounds on abnormal glucose tolerance were measured using db/db mice (male, 7 weeks of age, Charles River Laboratories Japan, Inc.). Each of the compounds was dissolved in a mixture of Gelucire 44/14 (trade name, product of Gattefosse) and PEG 400 (60:40), and was orally administered to the animal after a 16 to 20-hour fasting period. A glycemic load was applied by administering a 5 g/kg glucose solution 1 hour after administration of the drug solution. Blood was collected from the caudal vein 1 hour before the drug solution administration, before the glycemic load, and 0.25, 0.5, 1, 2, and 4 hours after the glycemic load using a blood-collecting tube coated with dipotassium ethylenediaminetetraacetate and was centrifuged to obtain a plasma sample. Each sample was diluted ten-fold with physiological saline, and the blood glucose level was measured using Glucose CII Kit (trade name, product of Wako Pure Chemical Industries, Ltd.). The blood glucose level AUC 0.25 to 4 hours after glycemic load was calculated as the "Blood glucose after glycemic load".

$EC_{50}$ and $ED_{50}$ were calculated using the test compound blood concentration (Cmax) and the dosage amount on the basis of the blood glucose rate of decrease for each group as an index of drug efficacy when the data for the control group was taken as 0.

TEST EXAMPLE 5 hERG Current Suppression Test

Using a HEK 293 cell transfected with a human ether-a-go-go-related gene (hERG), the hERG current which passed through the whole cell membrane under a voltage clamp was recorded by a whole-cell patch clamp method. To confirm the hERG current of the cell, a depolarization pulse was periodically applied while maintaining the membrane potential at −80 mV. After the generated current stabilized, the cell was perfused with a perfusate (applying solution) in which the test substance was dissolved for 10 minutes. The effects of the test substance on the hERG channel were evaluated on the basis of the change in the tail current induced by a +20 mV depolarization pulse for 1.5 seconds followed by another depolarization pulse of −50 mV for 1.5 seconds. Stimulation was performed at a frequency of once every 10 seconds. The test was carried out at 34° C. The absolute value of the maximum tail current was determined on the basis of the current value at the maintained membrane potential, and the rate of change (suppression rate) 10 minutes after application in the maximum tail current from before application of the test substance was calculated.

The hERG when 30 µM of the inventive compounds 1A, 12A, 44A, 18B, 31B, 41B, 71B, 103B, 4B, 31A, 3813, and 6813 was 50% or less in all cases.

Industrial Applicability

The glucokinase activators of the present invention have an excellent GK activating or hypoglycemic effect and few side effects (such as Q-T interval prolongation (relating to hERG current suppression) and insulin-induced hypoglycemia) and are therefore useful as pharmaceuticals for the treatment or prevention of diabetes, obesity, and the like.

The invention claimed is:

1. A compound represented by the general formula (1) or a pharmaceutically acceptable salt thereof:

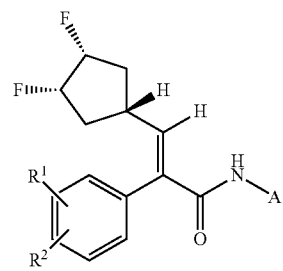

(1)

wherein:
$R^1$ and $R^2$ are each independently a hydrogen atom, a halogen atom, an amino group, a hydroxyl group, a hydroxyamino group, a nitro group, a cyano group, a sulfamoyl group, a $C_1$ to $C_6$ alkyl group, a $C_1$ to $C_6$ alkoxy group, a $C_1$ to $C_6$ alkylsulfanyl group, a $C_1$ to $C_6$ alkylsulfinyl group, a $C_1$ to $C_6$ alkylsulfonyl group, or a $C_1$ to $C_6$ alkoxy-$C_1$ to $C_6$ alkylsulfonyl group, and A is a substituted or unsubstituted heteroaryl group).

2. The compound according to claim 1 or a pharmaceutically acceptable salt thereof, wherein $R^1$ and $R^2$ are each independently a hydrogen atom, a halogen atom, or a $C_1$ to $C_6$ alkylsulfonyl group.

3. The compound according to claim 1 or a pharmaceutically acceptable salt thereof, wherein $R^1$ is a hydrogen atom or a halogen atom, and $R^2$ is a $C_1$ to $C_6$ alkylsulfonyl group.

4. The compound according to claim 1 or a pharmaceutically acceptable salt thereof, wherein $R^1$ is a hydrogen atom and $R^2$ is a $C_1$ to $C_6$ alkylsulfonyl group.

5. The compound according to claim 1 or a pharmaceutically acceptable salt thereof, wherein $R^1$ is a hydrogen atom, and $R^2$ is a cyclopropylsulfonyl group.

6. The compound according to claim 1 or a pharmaceutically acceptable salt thereof, wherein $R^1$ is a hydrogen atom, and $R^2$ is a methylsulfonyl group.

7. The compound according to claim 1 or a pharmaceutically acceptable salt thereof, wherein the compound is represented by formula (1a):

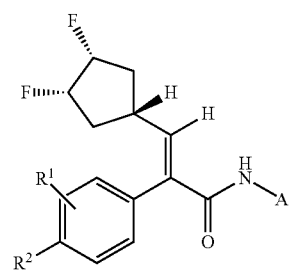

(1a)

wherein $R^1$, $R^2$, and A are as defined in formula (1) of claim 1.

8. The compound according to claim 1 or a pharmaceutically acceptable salt thereof, wherein the compound is represented by formula (1b):

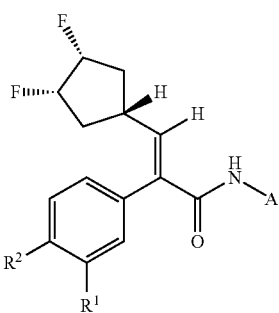

(1b)

wherein R¹, R², and A are as defined in formula (1) of claim 1.

9. The compound according to claim 1 or a pharmaceutically acceptable salt thereof, wherein A is an unsubstituted heteroaryl group or a heteroaryl group that is mono-substituted with a halogen atom, a $C_1$ to $C_6$ alkyl group optionally substituted with a halogen atom or a hydroxyl group, a $C_1$ to $C_6$ alkoxy group optionally substituted with a halogen atom or a hydroxyl group, a nitro group, a cyano group, or a group represented by the formula of $—(O)_p(CH_2)_mC(O)OR^3$, wherein $R^3$ is a hydrogen atom or a $C_1$ to $C_6$ alkyl group, m is an integer of 0 to 2, and p is 0 or 1.

10. The compound according to claim 1 or a pharmaceutically acceptable salt thereof, wherein A is a heteroaryl group that is mono-substituted with a halogen atom, a $C_1$ to $C_6$ alkyl group, or a $C_1$ to $C_6$ hydroxyalkyl group.

11. The compound according to claim 1 or a pharmaceutically acceptable salt thereof, wherein A is a heteroaryl group that is mono-substituted with a $C_1$ to $C_6$ alkoxy group optionally substituted with a halogen atom or a hydroxyl group, or a $C_1$ to $C_3$ alkoxy-$C_1$ to $C_3$ alkoxy group.

12. The compound according to claim 1 or a pharmaceutically acceptable salt thereof, wherein A is a heteroaryl group that is mono-substituted with a $C_1$ to $C_6$ alkylsulfanyl group that is optionally substituted with a halogen atom or a hydroxyl group.

13. The compound according to any of claim 9 or a pharmaceutically acceptable salt thereof, wherein A is an unsubstituted or mono-substituted five- or six-membered heteroaromatic ring, the heteroaromatic ring containing 1 to 3 heteroatoms selected from the group consisting of a sulfur atom, an oxygen atom, and a nitrogen atom, one of which is a nitrogen atom adjacent to a ring-connecting atom.

14. The compound according to any of claim 9 or a pharmaceutically acceptable salt thereof, wherein A is an unsubstituted or mono-substituted fused heterocycle having a five- or six-membered heteroaromatic ring, the heteroaromatic ring containing 1 to 3 heteroatoms selected from the group consisting of a sulfur atom, an oxygen atom, and a nitrogen atom, one of the heteroatoms being a nitrogen atom adjacent to a ring-connecting atom.

15. The compound according to any of claim 9 or a pharmaceutically acceptable salt thereof, wherein A is an unsubstituted or substituted heteroaromatic ring selected from the group consisting of:

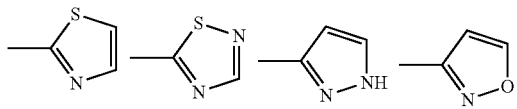

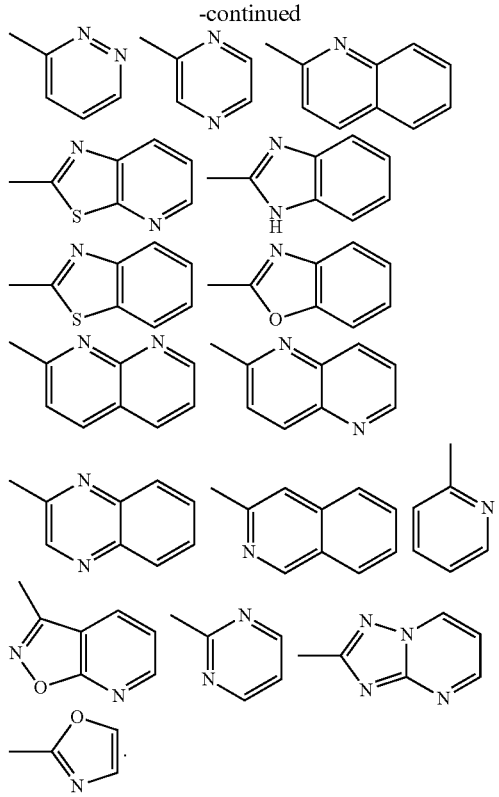

16. The compound according to claim 1 or a pharmaceutically acceptable salt thereof, selected from the group consisting of:

(E)-3-[(1α, 3α, 4α)-3,4-difluorocyclopentyl]-2-[4-(methylsulfonyl)phenyl]-N-(thiazol-2-ylacrylamide, (E)-3-[(1α, 3α, 4α)-3,4-difluorocyclopentyl]-N-(5-fluorothiazol-2-yl)-2-(4-(methylsulfonyl)phenyl)acrylamide, (E)-N-(5-chlorothiazol-2-yl)-3-[(1α, 3α, 4α)-3,4-difluorocyclopentyl]-2-(4-(methylsulfonyl)phenyl)acrylamide, (E)-3-[(1α, 3α, 4α)-3,4-difluorocyclopentyl]-2-(4-(methylsulfonyl)phenyl)-N-(4-methylthiazol-2-yl)acrylamide, (E)-3-[(1α, 3α, 4α)-3,4-difluorocyclopentyl]-2-(4-(methylsulfonyl)phenyl)-N-(5-methylthiazol-2-yl)acrylamide, (+)-(E)-3-[(1α, 3α, 4α)-3,4-difluorocyclopentyl]-N-[4-(2,2-dimethyl-1,3-dioxolan-4-yl)thiazol-2-yl]-2-(4-(methylsulfonyl)phenyl)acrylamide, (−)-(E)-3-[(1α, 3α, 4α)-3,4-difluorocyclopentyl]-N-[4-(2,2-dimethyl-1,3-dioxolan-4-yl)thiazol-2-yl]-2-(4-(methylsulfonyl)phenyl)acrylamide, (+)-(E)-3-[(1α, 3α, 4α)-3,4-difluorocyclopentyl]-N-[4-(1,2-dihydroxyethyl)thiazol-2-yl]-2-(4-(methylsulfonyl)phenyl)acrylamide, (−)-(E)-3-[(1α, 3α, 4α)-3,4-difluorocyclopentyl]-N-[4-(1,2-dihydroxyethyl)thiazol-2-yl]-2-(4-(methylsulfonyl)phenyl)acrylamide, (E)-N-[4-tert-butylthiazol-2-yl]-3-[((1α, 3α, 4α)-3,4-difluorocyclopentyl]-2-(4-(methylsulfonyl)phenyl)acrylamide, (E)-3-[(1α, 3α, 4α)-3,4-difluorocyclopentyl]-2-(4-(methylsulfonyl)phenyl)-N-{4-[2-(tetrahydro-2H-pyran-2-yloxy)ethyl]thiazol-2-yl}acrylamide, (E)-3-[(1α, 3α, 4α)-3,4-difluorocyclopentyl]-N-[4-(2-hydroxyethyl)thiazol-2-yl]-2-(4-(methylsulfonyl)phenyl)acrylamide,
(E)-3-[(1α, 3α, 4α)-3,4-difluorocyclopentyl]-N-[5-(N,N-dimethylsulfamoyl)thiazol-2-yl]-2-(4-(methylsulfonyl)phenyl)acrylamide,
(E)-3-[(1α, 3α, 4α)-3,4-difluorocyclopentyl]-N-[5-(4-methylpiperazine-1-ylsulfonyl)thiazol-2-yl]2-(4-(methylsulfonyl)phenyl)acrylamide,
(E)-3-[(1α, 3α, 4α)-3,4-difluorocyclopentyl]-2-(4-(methylsulfonyl)phenyl)-N-(1,2,4-thiadiazol-5-yl)acrylamide,
(E)-3-[(1α, 3α, 4α)-3,4-difluorocyclopentyl]-2-(4-(methylsulfonyl)phenyl)-N-(3-methyl-1,2,4-thiadiazol-5-yl)acrylamide,
(E)-3-[(1α, 3α, 4α)-3,4-difluorocyclopentyl]-N-(3-ethyl-1,2,4-thiadiazol-5-yl)-2-(4-(methylsulfonyl)phenyl)acrylamide,
(E)-3-[(1α, 3α, 4α)-3,4-difluorocyclopentyl]-N-(3-methoxy-1,2,4-thiadiazol-5-yl)-2-(4-(methylsulfonyl)phenyl)acrylamide,
(E)-3-[(1α, 3α, 4α)-3,4-difluorocyclopentyl]-2-(4-(methylsulfonyl)phenyl)-N-(pyridin-2-yl)acrylamide,
(E)-3-[(1α, 3α, 4α)-3,4-difluorocyclopentyl]-N-(5-fluoropyridin-2-yl)-2-(4-(methylsulfonyl)phenyl)acrylamide,
(E)-N-(5-chloropyridin-2-yl)-3-[(1α, 3α, 4α)-3,4-difluorocyclopentyl]-2-(4-(methylsulfonyl)phenyl)acrylamide,
(E)-3-[(1α, 3α, 4α)-3,4-difluorocyclopentyl]-2-(4-(methylsulfonyl)phenyl)-N-[5-(methylthio)pyridin-2-yl]acrylamide,
(E)-N-(5-cyclopropylpyridin-2-yl)-3-[(1α, 3α, 4α)-3,4-difluorocyclopentyl]-2-(4-(methylsulfonyl)phenyl)acrylamide,
(E)-3-[(1α, 3α, 4α)-3,4-difluorocyclopentyl]-N-[5-(hydroxymethyl)pyridin-2-yl]-2-(4-(methylsulfonyl)phenyl)acrylamide,
(E)-3-[(1α, 3α, 4α)-3,4-difluorocyclopentyl]-N-[5-(N,N-dimethylsulfamoyl)pyridin-2-yl]-2-(4-(methylsulfonyl)phenyl)acrylamide,
(E)-3-[(1α, 3α, 4α)-3,4-difluorocyclopentyl]-2-(4-(methylsulfonyl)phenyl)-N-(pyrazin-2-yl)acrylamide,
(E)-3-[(1α, 3α, 4α)-3,4-difluorocyclopentyl]-N-(5-methylpyrazin-2-yl)-2-(4-(methylsulfonyl)phenyl)acrylamide,
(E)-3-[(1α, 3α, 4α)-3,4-difluorocyclopentyl]-N-(5-ethylpyrazin-2-yl)-2-(4-(methylsulfonyl)phenyl)acrylamide,
(E)-3-[(1α, 3α, 4α)-3,4-difluorocyclopentyl]-N-(5-methoxypyrazin-2-yl)-2-(4-(methylsulfonyl)phenyl)acrylamide,
(E)-3-[(1α, 3α, 4α)-3,4-difluorocyclopentyl]-N-[5-(2-methylethoxy)pyrazin-2-yl]-2-(4-(methylsulfonyl)phenyl)acrylamide,
(E)-3-[(1α, 3α, 4α)-3,4-difluorocyclopentyl]-N-[5-(2-methoxyethoxy)pyrazin-2-yl]-2-(4-(methylsulfonyl)phenyl)acrylamide,
(E)-3-[(1α, 3α, 4α)-3,4-difluorocyclopentyl]-N-[5-(3-methoxypropoxy)pyrazin-2-yl]-2-(4-(methylsulfonyl)phenyl)acrylamide,
(E)-3-[(1α, 3α, 4α)-3,4-difluorocyclopentyl]-N-[5-(2-ethoxyethoxy)pyrazin-2-yl]-2-(4-(methylsulfonyl)phenyl)acrylamide,
(E)-3-[(1α, 3α, 4α)-3,4-difluorocyclopentyl]-2-(4-(methylsulfonyl)phenyl)-N-{5-[2-(methylthio)ethoxy]pyrazin-2-yl}acrylamide,
(E)-2-(4-(methylsulfonyl)phenyl)-3-[(1α, 3α, 4α)-3,4-difluorocyclopentyl]-N-[5-(2-hydroxyethylthio)pyrazin-2-yl]acrylamide,
(E)-3-[(1α, 3α, 4α)-3,4-difluorocyclopentyl]-2-(4-(methylsulfonyl)phenyl)-N-{5-[2-(tetrahydro-2H-pyran-2-yloxy)ethoxy]pyrazin-2-yl}acrylamide,
(E)-3-[(1α, 3α, 4α)-3,4-difluorocyclopentyl]-N-[5-(2-(hydroxyethoxy)pyrazin-2-yl)-2-(4-(methylsulfonyl)phenyl)acrylamide,
(E)-3-[(1α, 3α, 4α)-3,4-difluorocyclopentyl]-N-{5-[(4R)-2,2-dimethyl-1,3-dioxolan-4-yl]pyrazin-2-yl}-2-(4-(methylsulfonyl)phenyl)acrylamide,
(E)-3-[(1α, 3α, 4α)-3,4-difluorocyclopentyl]-N-{5-[(4S)-2,2-dimethyl-1,3-dioxolan-4-yl]pyrazin-2-yl}-2-(4-(methylsulfonyl)phenyl)acrylamide,
(E)-3-[(1α, 3α, 4α)-3,4-difluorocyclopentyl]-N-{5-[(2R)-1,2-dihydroxyethyl]pyrazin-2-yl}-2-(4-(methylsulfonyl)phenyl)acrylamide,
(E)-3-[(1α, 3α, 4α)-3,4-difluorocyclopentyl]-N-{5-[(2S)-1,2-dihydroxyethyl]pyrazin-2-yl}-2-(4-(methylsulfonyl)phenyl)acrylamide,
diethyl 5-{(E)-3-[(1α, 3α, 4α)-3,4-difluorocyclopentyl-2-(4-(methylsulfonyl)phenyl)]acrylamide}pyrazin-2-ylphosphonate,
diethyl (5-{(E)-3-[(1α, 3α, 4α)-3,4-difluorocyclopentyl-2-(4-(methylsulfonyl)phenyl)]acrylamide}pyrazin-2-yl)methylphosphonate,
(E)-3-[(1α, 3α, 4α)-3,4-difluorocyclopentyl]-N-[1-methyl-1H-pyrazol-3-yl]-2-(4-(methylsulfonyl)phenyl)acrylamide,
(E)-3-[(1α, 3α, 4α)-3,4-difluorocyclopentyl]-N-[1-ethyl-1H-pyrazol-3-yl]-2-(4-(methylsulfonyl)phenyl)acrylamide,
(E)-3-[(1α, 3α, 4α)-3,4-difluorocyclopentyl]-N-[1-(difluoromethyl)-1H-pyrazol-3-yl]-2-(4-(methylsulfonyl)phenyl)acrylamide,
(E)-3-[(1α, 3α, 4α)-3,4-difluorocyclopentyl]-N-[1-(2-fluoroethyl)-1H-pyrazol-3-yl]-2-(4-(methylsulfonyl)phenyl)acrylamide,
(E)-3-[(1α, 3α, 4α)-3,4-difluorocyclopentyl]-2-(4-(methylsulfonyl)phenyl)-N-[1-(2,2,2-trifluoroethyl)-1H-pyrazol-3-yl]acrylamide,
(E)-3-[(1α, 3α, 4α)-3,4-difluorocyclopentyl]-N-[1-(2-hydroxyethyl)-1H-pyrazol-3-yl]-2-(4-(methylsulfonyl)phenyl)acrylamide,
(E)-3-[(1α, 3α, 4α)-3,4-difluorocyclopentyl]-N-[1-(2-hydroxy-2-methylpropyl)-1H-pyrazol-3-yl]-2-(4-(methylsulfonyl)phenyl)acrylamide,
(E)-3-[(1α, 3α, 4α)-3,4-difluorocyclopentyl]-N-(1-{[(4R)-2,2-dimethyl-1,3-dioxolan-4-yl]methyl}-1H-pyrazol-3-yl)-2-(4-(methylsulfonyl)phenyl)acrylamide,
(E)-3-[(1α, 3α, 4α)-3,4-difluorocyclopentyl]-N-(1-{[(4S)-2,2-dimethyl-1,3-dioxolan-4-yl]methyl}-1H-pyrazol-3-yl)-2-(4-(methylsulfonyl)phenyl)acrylamide,
(E)-3-[(1α, 3α, 4α)-3,4-difluorocyclopentyl]-N-{1-[(2R)-2,3-dihydroxypropyl]-1H-pyrazol-3-yl}-2-(4-(methylsulfonyl)phenyl)acrylamide,
(E)-3-[(1α, 3α, 4α)-3,4-difluorocyclopentyl]-N-{1-[(2S)-2,3-dihydroxypropyl]-1H-pyrazol-3-yl}-2-(4-(methylsulfonyl)phenyl)acrylamide,
(E)-3-[(1α, 3α, 4α)-3,4-difluorocyclopentyl]-N-(isoxazol-3-yl)-2-(4-(methylsulfonyl)phenyl)acrylamide,
(E)-3-[(1α, 3α, 4α)-3,4-difluorocyclopentyl]-N-(6-methoxybenzo[d]thiazol-2-yl)-2-(4-(methylsulfonyl)phenyl)acrylamide, (E)-3-[(1α, 3α, 4α)-3,4-difluorocyclopentyl]-N-[6-(difluoromethoxy)benzo[d]thiazol-2-yl]-2-(4-(methylsulfonyl)phenyl)acrylamide, (E)-3-[(1α, 3α, 4α)-3,4-difluorocyclopentyl]-N-[5-(2-methoxyethoxy)thiazolo[5,4-b]pyridin-2-yl]-2-(4-(methylsulfonyl)phenyl)acrylamide, and ethyl (E)-2-{2-[(R)-2-(4-(methylsulfonyl)phenyl)-3-[(1α, 3α, 4α)-3,4-difluorocyclopentyl]acrylamide]thiazolo[5,4-b]pyridin-2-yloxy}acetate.

17. The compound according to claim 1 or a pharmaceutically acceptable salt thereof, which is selected from the group consisting of:

(E)-2-[4-cyclopropylsulfonyl)phenyl]-3-[(1α, 3α, 4α)-3,4-difluorocyclopentyl]-N-(thiazol-2-yl)acrylamide, (E)-2-(4-(cyclopropylsulfonyl)phenyl)-3-[(1α, 3α, 4α)-3,4-difluorocyclopentyl]-N-(5-fluorothiazol-2-yl)acrylamide, (E)-N-(5-bromothiazol-2-yl)-2-(4-(cyclopropylsulfonyl)phenyl)-3-[(1α, 3α, 4α)-3,4-difluorocyclopentyl]acrylamide, (E)-2-(4-(cyclopropylsulfonyl)phenyl)-3-[(1α, 3α, 4α)-3,4-difluorocyclopentyl]-N-(4-methylthiazol-2-yl)acrylamide, (E)-2-(4-(cyclopropylsulfonyl)phenyl)-3-[(1α, 3α, 4α)-3,4-difluorocyclopentyl]-N-(5-methylthiazol-2-yl)acrylamide, (+)-(E)-2-(4-(cyclopropylsulfonyl)phenyl)-3-[(1α, 3α, 4α)-3,4-difluorocyclopentyl]-N-[4-(2,2-dimethyl-1,3-dioxolan-4-yl)thiazol-2-yl]acrylamide, (−)-(E)-2-(4-(cyclopropylsulfonyl)phenyl)-3-[(1α, 3α, 4α)-3,4-difluorocyclopentyl]-N-[4-(2,2-dimethyl-1,3-dioxolan-4-yl)thiazol-2-yl]acrylamide, (E)-N-(4-tert-butylthiazol-2-yl)-2-(4-(cyclopropylsulfonyl)phenyl)-3-[(1α, 3α, 4α)-3,4-difluorocyclopentyl]acrylamide, (E)-2-(4-(cyclopropylsulfonyl)phenyl)-3-[(1α, 3α, 4α)-3,4-difluorocyclopentyl]-N-[5-(4-methylpiperazin-1-ylsulfonyl)thiazol-2-yl]acrylamide, methyl 3-{2-[(E)-2-(4-(cyclopropylsulfonyl)phenyl)-3-[(1α, 3α, 4α)-3,4-difluorocyclopentyl]acrylamide]thiazol-4-yl] propionate, (E)-2-(4-(cyclopropylsulfonyl)phenyl)-3-[(1α, 3α, 4α)-3,4-difluorocyclopentyl]-N-(1,2,4-thiadiazol-5-yl)acrylamide, (E)-2-(4-(cyclopropylsulfonyl)phenyl)-3-[(1α, 3α, 4α)-3,4-difluorocyclopentyl]-N-(3-methyl -1,2,4-thiadiazol-5-yl)acrylamide, (E)-2-(4-(cyclopropylsulfonyl)phenyl)-3-[(1α, 3α, 4α)-3,4-difluorocyclopentyl]-N-(3-ethyl-1,2,4-thiadiazol-5-yl)acrylamide, (E)-2-(4-(cyclopropylsulfonyl)phenyl)-3-[(1α, 3α, 4α)-3,4-difluorocyclopentyl]-N-(3-phenyl-1,2,4-thiadiazol-5-yl)acrylamide, (E)-2-(4-(cyclopropylsulfonyl)phenyl)-3-[(1α, 3α, 4α)-3,4-difluorocyclopentyl]-N-(pyridin-2-yl)acrylamide, (E)-2-(4-(cyclopropylsulfonyl)phenyl)-3-[(1α, 3α, 4α)-3,4-difluorocyclopentyl]-N-[5-(methylthio)pyridin-2-yl]acrylamide, (E)-N-(5-cyclopropylpyridin-2-yl)-2-(4-(cyclopropylsulfonyl)phenyl)-3-[(1α, 3α, 4α)-3,4-difluorocyclopentyl]acrylamide, (E)-2-(4-(cyclopropylsulfonyl)phenyl)-3-[(1α, 3α, 4α)-3,4-difluorocyclopentyl]-N-[5-(hydroxymethyl)pyridin-2-yl]acrylamide, (E)-2-(4-(cyclopropylsulfonyl)phenyl)-3-[(1α, 3α, 4α)-3,4-difluorocyclopentyl]-N-[5-(N,N -dimethylsulfamoyl)pyridin-2-yl]acrylamide, (E)-2-(4-(cyclopropylsulfonyl)phenyl)-3-[(1α, 3α, 4α)-3,4-difluorocyclopentyl]-N-(pyrazin-2-yl)acrylamide, (E)-2-(4-(cyclopropylsulfonyl)phenyl)-3-[(1α, 3α, 4α)-3,4-difluorocyclopentyl]-N-(5-methylpyrazin-2-yl)acrylamide, (E)-2-(4-(cyclopropylsulfonyl)phenyl)-3-[(1α, 3α, 4α)-3,4-difluorocyclopentyl]-N-(5-ethylpyrazin-2-yl)acrylamide, (E)-2-(4-(cyclopropylsulfonyl)phenyl)-3-[(1α, 3α, 4α)-3,4-difluorocyclopentyl]-N-(5-methoxypyrazin-2-yl)acrylamide, (E)-2-(4-(cyclopropylsulfonyl)phenyl)-3-[(1α, 3α, 4α)-3,4-difluorocyclopentyl]-N-5-(methylthio)pyrazin-2-yl]acrylamide, (E)-2-(4-(cyclopropylsulfonyl)phenyl)-3-[(1α, 3α, 4α)-3,4-difluorocyclopentyl]-N-[5-(2-methylethoxy)pyrazin-2-yl]acrylamide, (E)-2-(4-(cyclopropylsulfonyl)phenyl)-3-[(1α, 3α, 4α)-3,4-difluorocyclopentyl]-N-[5-(2-methoxyethoxy)pyrazin-2-yl]acrylamide, (E)-2-(4-(cyclopropylsulfonyl)phenyl)-3-[(1α, 3α, 4α)-3,4-difluorocyclopentyl]-N-[5-(3-methoxypropoxy)pyrazin-2-yl]acrylamide, (E)-2-(4-(cyclopropylsulfonyl)phenyl)-3-[(1α, 3α, 4α)-3,4-difluorocyclopentyl]-N-[5-(2-ethoxyethoxy)pyrazin-2-yl]acrylamide, (E)-2-(4-(cyclopropylsulfonyl)phenyl)-3-[(1α, 3α, 4α)-3,4-difluorocyclopentyl]-N-{5-[2-(methylthio)ethoxy]pyrazin-2-yl}acrylamide, (E)-2-(4-(cyclopropylsulfonyl)phenyl)-3-[(1α, 3α, 4α)-3,4-difluorocyclopentyl]-N-{5-[2-(tetrahydro-2H-pyran-2-ethoxy)ethoxy]pyrazin-2-yl}acrylamide, (E)-2-(4-(cyclopropylsulfonyl)phenyl)-3-[(1α, 3α, 4α)-3,4-difluorocyclopentyl]-N-[5-(2-(hydroxyethoxy)pyrazin-2-yl)acrylamide, (E)-2-(4-(cyclopropylsulfonyl)phenyl)-3-[(1α, 3α, 4α)-3,4-difluorocyclopentyl]-N-{5-[(4R)-2,2-dimethyl-1,3-dioxolan-4-yl]pyrazin-2-yl}acrylamide, (E)-2-(4-(cyclopropylsulfonyl)phenyl)-3-[(1α, 3α, 4α)-3,4-difluorocyclopentyl]-N-{5-[(4S)-2,2-dimethyl-1,3-dioxolan-4-yl]pyrazin-2-yl}acrylamide, (E)-2-(4-(cyclopropylsulfonyl)phenyl)-3-[(1α, 3α, 4α)-3,4-difluorocyclopentyl]-N-{5-[(2R)-1,2-dihydroxyethyl]pyrazin-2-yl}acrylamide, (E)-2-(4-(cyclopropylsulfonyl)phenyl)-3-[(1α, 3α, 4α)-3,4-difluorocyclopentyl]-N-{5-[(2S)-1,2-dihydroxyethyl]pyrazin-2-yl}acrylamide, diethyl 5-{(E)-2-(4-(cyclopropylsulfonyl)phenyl)-3-[(1α, 3α, 4α)-3,4-difluorocyclopentyl]acrylamide}pyrazin-2-yl phosphonate, diethyl (5-{(E)-2-(4-(cyclopropylsulfonyl)phenyl)-3-[(1α, 3α, 4α)-3,4-difluorocyclopentyl]acrylamide}pyrazin-2-yl methylphosphonate, (E)-2-(4-(cyclopropylsulfonyl)phenyl)-3-[(1α, 3α, 4α)-3,4-difluorocyclopentyl]-N-(1-methyl -1H-pyrazol-3-yl)acrylamide, (E)-2-(4-(cyclopropylsulfonyl)phenyl)-3-[(1α, 3α, 4α)-3,4-difluorocyclopentyl]-N-(1-ethyl-1H -pyrazol-3-yl)acrylamide, (E)-2-(4-(cyclopropylsulfonyl)phenyl)-3-[(1α, 3α, 4α)-3,4-difluorocyclopentyl]-N-(1-(2-fluoroethyl)-1H-pyrazol-3-yl)acrylamide, (E)-2-(4-(cyclopropylsulfonyl)phenyl)-3-[(1α, 3α, 4α)-3,4-difluorocyclopentyl]-N-[1-(2-hydroxyethyl)-1H-pyrazol-3-yl]acrylamide, (E)-2-(4-(cyclopropylsulfonyl)phenyl)-3-[(1α, 3α, 4α)-3,4-difluorocyclopentyl]-N-[1-(2-hydroxy-2-methylpropyl)-1H-pyrazol-3-yl]acrylamide, (E)-2-(4-(cyclopropylsulfonyl)phenyl)-3-[(1α, 3α, 4α)-3,4-difluorocyclopentyl]-N-(1-{[(4R)-2,2-dimethyl-1,3-dioxolan-4-yl]methyl}-1H-pyrazol-3 -yl}acrylamide, (E)-2-(4-(cyclopropylsulfonyl)phenyl)-3-[(1α, 3α, 4α)-3,4-difluorocyclopentyl]-N-(1-{[(4S)-2,2-dimethyl-1,3-dioxolan-4-yl]methyl}-1H-pyrazol-3 -yl}acrylamide, (E)-2-(4-(cyclopropylsulfonyl)phenyl)-3-[(1α, 3α, 4α)-3,4-difluorocyclopentyl]-N-{1-[(2R)-2,3-dihydroxypropyl]-1 H-pyrazol-3 -yl}acrylamide, (E)-2-(4-(cyclopropylsulfonyl)phenyl)-3-[(1α, 3α, 4α)-3,4-difluorocyclopentyl]-N-{1-[(2S)-2,3-dihydroxypropyl]-1 H-pyrazol-3 -yl}acrylamide, (E)-2-(4-(cyclopropylsulfonyl)phenyl)-3-[(1α, 3α, 4α)-3,4-difluorocyclopentyl]-N-(isoxazol-3-yl)acrylamide, (E)-N-(benzo[d]thiazol-2-yl)-2-(4-(cyclopropylsulfonyl)phenyl)-3-[(1α, 3α, 4α)-3,4-difluorocyclopentyl]acrylamide, (E)-2-(4-(cyclopropylsulfonyl)phenyl)-3-[(1α, 3α, 4α)-3,4-difluorocyclopentyl]-N-(6-methoxybenzo[d]thiazol-2-yl)acrylamide, (E)-2-(4-(cyclopropylsulfonyl)phenyl)-3-[(1α, 3α, 4α)-3,4-difluorocyclopentyl]-N-[6-difluoromethoxy]benzo[d]thiazol-2-yl]acrylamide, (E)-2-(4-(cyclopropylsulfonyl)phenyl)-3-[(1α, 3α, 4α)-3,4-difluorocyclopentyl]-N-(6-fluorobenzo[d]thiazol-2-yl)acrylamide, 1-methylethyl 2-{(E)-2-(4-(cyclopropylsulfonyl)phenyl)-3-[(1α, 3α, 4α)-3,4-difluorocyclopentyl]acrylamide}benzo[d]thiazol-6-carboxylate, (E)-2-(4-(cyclopropylsulfonyl)phenyl)-3-[(1α, 3α, 4α)-3,4-difluorocyclopentyl]-N-(thiazolo[5,4-b]pyridin-2-yl)acrylamide, (E)-N-(5-butoxythiazolo[5,4-b]pyridin-2-yl)-2-(4-(cyclopropylsulfonyl)phenyl)-3-[((1α, 3α, 4α)-3,4-difluorocyclopentyl]acrylamide, (E)-2-(4-(cyclopropylsulfonyl)phenyl)-3-[(1α, 3α, 4α)-3,4-difluorocyclopentyl]-N-[5-(2-methoxyethoxy)thiazolo[5,4-b]pyridin-2-yl)acrylamide, and ethyl 2-{2-[(R)-2-(4-(cyclopropylsulfonyl)phenyl)-3-[(1α, 3α, 4α)-3,4-difluorocyclopentyl]acrylamide]thiazolo[5,4-b]pyridin-5 -yloxy}acetate.

18. The compound according to claim 1 or a pharmaceutically acceptable salt thereof, which is selected from the group consisting of:

(E)-3-[((1α, 3α, 4α)-3,4-difluorocyclopentyl]-2-[4-(ethylsulfonyl)phenyl]-N-(thiazol-2-yl)acrylamide, (E)-3-[((1α, 3α, 4α)-3,4-difluorocyclopentyl]-2-[4-(ethylsulfonyl)phenyl]-N-(5-methylpyrazin-2-yl)acrylamide, and (E)-3-[((1α, 3α, 4α)-3,4-difluorocyclopentyl]-2-[4-(ethylsulfonyl)phenyl]-N-(1-methyl-1H -pyrazol-3-yl)acrylamide.

19. The compound according to claim 1 or a pharmaceutically acceptable salt thereof, which is selected from the group consisting of:

(E)-3 -[(1 α, 3α, 4α)-3,4-difluorocyclopentyl]-2-[4-(2-methoxyethylsulfonyl)phenyl]-N-(thiazol -2-yl)acrylamide, (E)-3 -[(1 α, 3α, 4α)-3,4-difluorocyclopentyl]-2-[4-(2-methoxyethylsulfonyl)phenyl]-N-(5 -methylpyrazin-2-yl)acrylamide, and (E)-3 -[(1 α, 3α, 4α)-3,4-difluorocyclopentyl]-2-[4-(2-methoxyethylsulfonyl)phenyl]-N-(1-methyl-1 H-pyrazol-3 -yl)acrylamide.

20. A method for treating diabetes, comprising administering an effective amount of the compound according to claim 1 or a pharmaceutically acceptable salt thereof to a patient in need thereof.

21. A pharmaceutical composition, comprising: the compound according to claim 1, or a pharmaceutically acceptable salt thereof; and a pharmaceutically acceptable carrier.

22. The compound according to claim 1 or pharmaceutically acceptable salt thereof, which is selected from the group consisting of:

(E)-3-((1α, 3α, 4α)-3,4-difluorocyclopentyl)-2-(4-(methylsulfonyl)phenyl)-N-(thiazol-2-yl)acrylamide, (E)-3-((1α, 3α, 4α)-3,4-difluorocyclopentyl)-2-(4-(methylsulfonyl)phenyl)-N-(pyrazin-2-yl)acrylamide, (E)-3-((1α, 3α, 4α)-3,4-difluorocyclopentyl)-N-(5-methylpyrazin-2-yl)-2-(4-(methylsulfonyl)phenyl)acrylamide, (E)-3-((1α, 3α, 4α)-3,4-difluorocyclopentyl)-N-(5-(2-methoxyethoxy)pyrazin-2-yl)-2-(4-(methylsulfonyl)phenyl)acrylamide, (E)-3-((1α, 3α, 4α)-3,4-difluorocyclopentyl)-N-(1-methyl-1H-pyrazol-3-yl)-2-(4-(methylsulfonyl)phenyl)acrylamide, (E)-3-(1α, 3α, 4α)-3,4-difluorocyclopentyl)-N-(1-(difluoromethyl)-1H-pyrazol-3-yl)-2-(4-(methylsulfonyl)phenyl)acrylamide, (E)-3-((1α, 3α, 4α)-3,4-difluorocyclopentyl)-N-(5-(2-methoxyethoxy)thiazolo[5,4-b]pyridin-2-yl)-2-(4-(methylsulfonyl)phenyl)acrylamide, (E)-3-((1α, 3α, 4α)-3,4-difluorocyclopentyl)-N-(5-(2-(dimethylamino)ethoxy)thiazolo[5,4-b]pyridin-2-yl)-2-(4-(methylsulfonyl)phenyl)acrylamide, (E)-2-(4-(cyclopropylsuifonyl)phenyl)-3-((1α, 3α, 4α)-3,4-difluorocyclopentyl)-N-(thiazol-2-yl)acrylamide, (E)-2-(4-(cyclopropylsulfonyl)phenyl)-3-((1α, 3α, 4α)-3,4-difluorocyclopentyl-N-(5-fluorothiazol-2-yl)acrylamide, (E)-2-(4-(cyclopropylsulfonyl)phenyl)-3-((1α, 3α, 4α)-3,4-difluorocyclopentyl)-N-(4-methylthiazol-2-yl)acrylamide, (E)-2-(4-(cyclopropylsulfonyl)phenyl)-3-((1α, 3α, 4α)-3,4-difluorocyclopentyl)-N-(1,2,4-thiadiazol-5-yl)acrylamide, (E)-2-(4-(cyclopropylsulfonyl)phenyl)-3-((1α, 3α, 4α)-3,4-difluorocyclopentyl)-N-(3-methyl -1,2,4-thiadiazol-5-yl)acrylamide, (E)-2-(4-(cyclopropylsulfonyl)phenyl)-3-((1α, 3α, 4α)-3,4-difluorocyclopentyl)-N-(5-methylpyrazin-2-yl)acrylamide, (E)-2-(4-(cyclopropylsulfonyl)phenyl)-3-((1α,3α,4α)-3,4-difluorocyclopentyl)-N-(5-(2-methoxyethoxy)pyrazin-2-yl)acrylamide, (E)-2-(4-(cyclopropylsulfonyl)phenyl)-3-((1α, 3α, 4α)-3,4-difluorocyclopentyl)-N-(5-(2-hydroxyethoxy)pyrazin-2-yl)acrylamide, (E)-2-(4-(cyclopropylsulfonyl)phenyl)-3-((1α, 3α, 4α)-3,4-difluorocyclopentyl)-N-(1-methyl -1H-pyrazol-3-yl)acrylamide, (E)-2-(4-(cyclopropylsulfonyl)phenyl)-3-((1α, 3α, 4α)-3,4-difluorocyclopentyl)-N-(1(2-hydroxyethyl)-1H-pyrazol-3-yl)acrylamide, (E)-2 -(4-(cyclopropylsulfonyl)phenyl)-3-((1α, 3α, 4α)-3,4-difluorocyclopentyl)-N-(thiazolo[5,4-b]pyridin-2-yl)acrylamide, (E)-2-(4-(cyclopropylsulfonyl)phenyl)-3-((1α, 3α, 4α)-3,4-difluorocyclopentyl)-N-(5-((2-(piperidin-1-yl)ethyl)thio)thiazol-2-yl)acrylamide, (E)-2-(4-(cyclopropylsulfonyl)phenyl)-3-((1α, 3α, 4α)-3, 4-difluorocyclopentyl)-N-(5-(2-hydroxy-2-methylpropoxy)pyrazin-2-yl)acrylamide, and (E)-2-(4-(cyclopropylsulfonyl)phenyl)-3-((1α, 3α, 4α) 3,4-difluorocyclopentyl)-N-(5-(2-(dimethylamino) ethoxy)thiazolo[5, 4-b]pyridin-2-yl)acrylamide.

23. A compound selected from the group consisting of:

(E)-3-((1α, 3α, 4α)-3,4-difluorocyclpentyl)-2-(4-(methylsulfonyl)phenyl)-N-(thiazol-2- yl)acrylamide, (E)-3-((1α, 3α, 4α)-3,4-difluorocyclopentyl)-2-(4-(methylsulfonyl)phenyl)-N-(pyrazin-2-yl)acrylamide, (E)-3-((1α, 3α, 4α)-3,4-difluorocyclopentyl)-N-(5-methylpyazin-2-yl)-2-(4-(methylsulfonyl)phenyl)acrylamide, (E)-3-((1α, 3α, 4α)-3,4-difluorocyclopentyl)-N-(5-(2-methoxyethoxy)pyrazin-2-yl)-2-(4-(methylsulfonyl)phenyl)acrylamide, (E)-3-((1α, 3α, 4α)-3,4-difluorocyclopentyl)-N-(1-methyl-1H-pyrazol-3-yl)-2-(4-(methylsulfonyl)phenyl)acrylamide, (E)-3-((1α, 3α, 4α)-3,4-difluorocyclopentyl)-N-(1-(difluoromethyl)- 1H-pyrazol-3-yl)-2-(4-methylsulfonyl)phenyl)acrylamide, (E)-3-((1α, 3α, 4α)-3,4-difluorocyclopentyl)-N-(5-(2-methoxyethoxy)thiazolo[5,4-b]pyridin-2-yl)-2-(4-(methylsulfonyl)phenyl)acrylamide, (E)-3-((1α, 3α, 4α)-3,4-difluorocyclopentyl)-N-(5-(2-(dimethylamino)ethoxy)thiazolo[5,4-b]pyridin-2-yl)-2-(4-(methylsulfonyl)phenyl)acrylamide, (E)-2-(4-(cyclopropylsulfonyl)phenyl)-3-((1α, 3α, 4α)-3, 4-difluorocyclopentyl)-N-(thiazol-2-yl)acrylamide, (E)-2-(4-(cyclopropylsulfonyl)phenyl)-3-((1α, 3α, 4α)-3, 4-difluorocyclopentyl)-N-(5-fluorothiazol-2-yl)acrylamide, (E)-2-(4-(cyclopropylsulfonyl)phenyl)-3-((1α, 3α, 4α)-3, 4-difluorocyclopentyl)-N-(4-methylthiazol-2-yl)acrylamide, (E)-2-(4-(cyclopropylsulfonyl)phenyl)-3-((1α, 3α, 4α)-3, 4-difluorocyclopentyl)-N-(1,2,4-thiadiazol-5-yl)acrylamide, (E)-2-(4-(cyclopropylsulfonyl)phenyl)-3-((1α, 3α, 4α)-3, 4-difluorocyclopentyl)-N-(3-methyl-1,2,4-thiadiazol-5-yl)acrylamide, (E)-2-(4-(cyclopropylsulfonyl)phenyl)-3-((1α, 3α, 4α)-3, 4-difluorocyclopentyl)-N-(5-methylpyazin-2-yl)acrylamide, (E)-2-(4-(cyclopropylsulfonyl)phenyl)-3-((1α, 3α, 4α)-3, 4-difluorocyclopentyl)-N-(5-(2-methoxyethoxy) pyrazin-2-yl)acrylamide, (E)-2-(4-(cyclopropylsulfonyl)phenyl)-3-((1α, 3α, 4α)-3, 4-difluorocyclopentyl)-N-(5-(2-hydroxyethoxy) pyrazin-2-yl)acrylamide, (E)-2-(4-(cyclopropylsulfonyl)phenyl)-3-((1α, 3α, 4α)-3, 4-difluorocyclopentyl)-N-(1-methyl -1H-pyrazol-3-yl) acrylamide, (E)-2-(4-(cyclopropylsulfonyl)phenyl)-3-((1α, 3α, 4α)-3, 4-difluorocyclopentyl)-N-(1-(2-hydroxyethyl)-1H-pyrazol-3-yl)acrylamide, (E)-2-(4-(cyclopropylsulfonyl)phenyl)-3-((1α, 3α, 4α)-3, 4-difluorocyclopentyl)-N-(thiazolo[5,4-b]pyridin-2-yl) acrylamide, (E)-2-(4-(cyclopropylsulfonyl)phenyl)-3-((1α, 3α, 4α)-3, 4-difluorocyclopentyl)-N-(5-2-(piperidin-1-yl)ethyl) thio)thiaz01-2-yl)acrylamide, (E)-2-(4-(cyclopropylsulfonyl)phenyl)-3-((1α, 3α, 4α)-3, 4-difluorocyclopentyl)-N-(5-(2-hydroxy-2-methylpropoxy)pyrazin-2 -yl)acrylamide, (E)-2-(4-(cyclopropylsulfonyl)phenyl)-3-((1α, 3α, 4α)-3, 4-difluorocyclopentyl)-N-(5-(2-(dimethylamino) ethoxy)thiazolo[5,4-]pyridin-2-yl)acrylamide, (E)-3-((1α, 3α, 4α)-3,4-difluorocyclopentyl)-2-(4-(methylsulfonyl)phenyl)-N-(4-(2-hydroxyethyl)thiazol-2-yl) acrylamide, (E)-3-((1α, 3α, 4α)-3,4-difluorocyclopentyl)-N-(1-(2-hydroxyethyl)-1H-pyrazol-3-yl)-2-(4-(methylsulfonyl) phenyl)acrylamide, (E)-2-(4-(cyclopropylsulfonyl)phenyl)-3-((1α, 3α, 4α)-3, 4-difluorocyclopentyl)-N-(5-(hydroxymethyl)pyridin-2-yl)acrylamide, Diethyl ((2-((E)-2-(4-(cyclopropylsulfonyl)phenyl)-3-(((1r,3R,4S)-3,4-difluorocyclopentyl) acrylamido)thiazol-5-yl)methyl)phosphonate, and (E)-2-(4-(cyclopropylsulfonyl)phenyl)-3-((1α, 3α, 4α)-3, 4-difluorocyclopentyl)-N-(5-((2-aminoethyl)thio)thiazol-2-yl)acrylamide, or a pharmaceutically acceptable salt thereof.

* * * * *